US008611553B2

(12) United States Patent
Bakalos et al.

(10) Patent No.: US 8,611,553 B2
(45) Date of Patent: Dec. 17, 2013

(54) ANR INSTABILITY DETECTION

(75) Inventors: Pericles Nicholas Bakalos, Maynard, MA (US); Jason Harlow, Watertown, MA (US)

(73) Assignee: Bose Corporation, Framingham, MA (US)

( * ) Notice: Subject to any disclaimer, the term of this patent is extended or adjusted under 35 U.S.C. 154(b) by 792 days.

(21) Appl. No.: 12/766,902

(22) Filed: Apr. 25, 2010

(65) Prior Publication Data

US 2011/0243344 A1 Oct. 6, 2011

Related U.S. Application Data

(63) Continuation-in-part of application No. 12/749,935, filed on Mar. 30, 2010, now Pat. No. 8,315,405.

(51) Int. Cl.
*A61F 11/06* (2006.01)
*G10K 11/16* (2006.01)
*H04R 1/10* (2006.01)

(52) U.S. Cl.
USPC ......... 381/72; 381/71.6; 381/71.1; 381/71.14

(58) Field of Classification Search
USPC ......... 381/71.1, 71.2, 71.6, 71.8, 71.9, 71.13, 381/71.14, 72, 73.1, 94.1
See application file for complete search history.

(56) References Cited

U.S. PATENT DOCUMENTS

| | | | | |
|---|---|---|---|---|
| 5,255,325 | A | 10/1993 | Ishimitsu et al. | |
| 5,337,366 | A | 8/1994 | Eguchi et al. | |
| 5,699,436 | A | 12/1997 | Claybaugh et al. | |
| 5,724,433 | A | 3/1998 | Engebretson et al. | |
| 5,815,582 | A | 9/1998 | Claybaugh et al. | |
| 5,937,070 | A | 8/1999 | Todter et al. | |
| 6,094,489 | A | 7/2000 | Ishige et al. | |
| 6,118,878 | A * | 9/2000 | Jones | 381/72 |
| 6,160,893 | A | 12/2000 | Saunders et al. | |
| 6,418,228 | B1 | 7/2002 | Terai et al. | |
| 6,522,753 | B1 | 2/2003 | Matsuzawa et al. | |
| 6,567,524 | B1 | 5/2003 | Svean et al. | |
| 6,717,537 | B1 * | 4/2004 | Fang et al. | 341/143 |
| 6,744,882 | B1 | 6/2004 | Gupta et al. | |
| 7,039,195 | B1 | 5/2006 | Svean et al. | |
| 7,103,188 | B1 * | 9/2006 | Jones | 381/71.9 |

(Continued)

FOREIGN PATENT DOCUMENTS

| | | |
|---|---|---|
| JP | 2254898 A | 10/1990 |
| JP | 5341792 A | 12/1993 |

(Continued)

OTHER PUBLICATIONS

Invitation to Pay Additional Fees dated Aug. 3, 2010 for PCT/US2010/032557.

(Continued)

*Primary Examiner* — Mohammad Islam
*Assistant Examiner* — David Ton

(57) ABSTRACT

Apparatus and method of an ANR circuit detecting instances of instability in at least the provision of feedback-based ANR, monitoring audio that includes feedback anti-noise sounds for acoustic output by an acoustic driver for a sound having characteristics indicative of instability including at least a frequency within a range of frequencies and an amplitude reaching at least a predetermined minimum amplitude, and perhaps also a sinusoidal waveform.

13 Claims, 30 Drawing Sheets

(56) References Cited

U.S. PATENT DOCUMENTS

| | | | | |
|---|---|---|---|---|
| 7,260,209 | B2 | 8/2007 | Harvey et al. | |
| 7,292,973 | B1 | 11/2007 | Johnston et al. | |
| 7,340,064 | B2 | 3/2008 | Onishi et al. | |
| 7,433,481 | B2 | 10/2008 | Armstrong et al. | |
| 7,627,127 | B2 | 12/2009 | Aida et al. | |
| 7,706,550 | B2 | 4/2010 | Amada et al. | |
| 8,340,318 | B2 | 12/2012 | Copley et al. | |
| 2003/0053636 | A1 | 3/2003 | Goldberg et al. | |
| 2004/0138769 | A1 | 7/2004 | Akiho | |
| 2004/0240677 | A1 | 12/2004 | Onishi et al. | |
| 2005/0117754 | A1 | 6/2005 | Sakawaki | |
| 2007/0003078 | A1 | 1/2007 | Escott et al. | |
| 2007/0076896 | A1 | 4/2007 | Hosaka et al. | |
| 2007/0223715 | A1 | 9/2007 | Barath et al. | |
| 2008/0025530 | A1 | 1/2008 | Romesburg | |
| 2008/0095383 | A1 | 4/2008 | Pan et al. | |
| 2008/0112569 | A1* | 5/2008 | Asada | 381/71.1 |
| 2008/0162072 | A1 | 7/2008 | Copley et al. | |
| 2008/0170725 | A1* | 7/2008 | Asada et al. | 381/107 |
| 2008/0192957 | A1 | 8/2008 | Kubo | |
| 2008/0292113 | A1 | 11/2008 | Tian | |
| 2008/0310652 | A1 | 12/2008 | Gustavsson | |
| 2009/0034748 | A1 | 2/2009 | Sibbald | |
| 2009/0161889 | A1 | 6/2009 | Magrath | |
| 2009/0245529 | A1* | 10/2009 | Asada et al. | 381/71.6 |
| 2010/0150367 | A1* | 6/2010 | Mizuno | 381/71.6 |
| 2010/0266137 | A1* | 10/2010 | Sibbald et al. | 381/71.6 |
| 2010/0272275 | A1 | 10/2010 | Carreras et al. | |
| 2010/0272276 | A1 | 10/2010 | Carreras | |
| 2010/0272277 | A1 | 10/2010 | Joho et al. | |
| 2010/0272278 | A1 | 10/2010 | Joho et al. | |
| 2010/0272279 | A1 | 10/2010 | Joho et al. | |
| 2010/0272280 | A1 | 10/2010 | Joho et al. | |
| 2010/0272281 | A1 | 10/2010 | Carreras et al. | |
| 2010/0272283 | A1 | 10/2010 | Carreras et al. | |
| 2010/0272284 | A1 | 10/2010 | Joho et al. | |
| 2011/0188665 | A1 | 8/2011 | Burge et al. | |

FOREIGN PATENT DOCUMENTS

| | | | |
|---|---|---|---|
| JP | 8006571 | A | 1/1996 |
| JP | 3402331 | B2 | 5/2003 |
| JP | 2005257720 | A | 9/2005 |
| JP | 2007536877 | A | 12/2007 |
| JP | 2008216375 | A | 9/2008 |
| WO | 92/05538 | A1 | 4/1992 |
| WO | 2008113822 | A2 | 9/2008 |
| WO | 2009041012 | A1 | 4/2009 |

OTHER PUBLICATIONS

International Search Report and Written Opinion dated Sep. 16, 2010 for PCT/US10/032557.

European Office Action dated Nov. 7, 2012 for Application No. 10715648.1-2213.

Japanese Office Action dated Mar. 19, 2013 for Appication No. 2012-508587.

Chinese Office Action dated Feb. 7, 2013 for Chinese Application No. 201080026215.0 with accompanying English translation.

European Search Report dated Jul. 26, 2013 for Application No. 13172772.9-1558.

Second Chinese Office Action dated Aug. 20, 2013 for Chinese Application No. 201080026215.0.

* cited by examiner

ANR INSTABILITY DETECTION

CROSS-REFERENCE TO RELATED APPLICATION

The present application is a continuation-in-part of application Ser. No. 12/749,935 filed Mar. 30, 2010 by Pericles N. Bakalos and Ricardo F. Carreras, now U.S. Pat. No. 8,315,405, the disclosure of which is incorporated herein by reference.

TECHNICAL FIELD

This disclosure relates to personal active noise reduction (ANR) devices to reduce acoustic noise in the vicinity of at least one of a user's ears.

BACKGROUND

Headphones and other physical configurations of personal ANR device worn about the ears of a user for purposes of isolating the user's ears from unwanted environmental sounds have become commonplace. In particular, ANR headphones in which unwanted environmental noise sounds are countered with the active generation of anti-noise sounds, have become highly prevalent, even in comparison to headphones or ear plugs employing only passive noise reduction (PNR) technology, in which a user's ears are simply physically isolated from environmental noises. Especially of interest to users are ANR headphones that also incorporate audio listening functionality, thereby enabling a user to listen to electronically provided audio (e.g., playback of recorded audio or audio received from another device) without the intrusion of unwanted environmental noise sounds.

Unfortunately, despite various improvements made over time, existing personal ANR devices continue to suffer from a variety of drawbacks. Foremost among those drawbacks are undesirably high rates of power consumption leading to short battery life, undesirably narrow ranges of audible frequencies in which unwanted environmental noise sounds are countered through ANR, instances of unpleasant ANR-originated sounds, and instances of actually creating more unwanted noise sounds than whatever unwanted environmental sounds may be reduced.

SUMMARY

An ANR circuit employs first, second and third buffers to buffer ANR settings in preparation for configuring one or more components of the ANR circuit during operation and in synchronization with the transfer of at least one piece of digital data within the ANR circuit. The first and second buffers are alternately used to carry out such configuring, while the third buffer stores a "failsafe" ANR settings to be automatically used in configuring the one or more components of the ANR circuit in response to an indication of instability in the provision feedback-based ANR, feedforward-based ANR and/or pass-through audio being detected.

In one aspect, an ANR circuit includes a first ADC; a DAC; a first digital filter; a first pathway within the ANR circuit through which digital data representing sounds flows from the first ADC to the DAC through at least the first digital filter at a first data transfer rate through at least part of the first pathway; a first ANR settings buffer and a second ANR settings buffer to be alternately employed in configuring at least one ANR setting in synchronization with a transfer of a piece of digital data transferred through at least part of the first pathway at the first data transfer rate; and a third ANR settings buffer to store at least one failsafe ANR setting to configure the at least one ANR setting in response to an instance of instability being detected in the ANR circuit.

Implementations may include, and are not limited to, one or more of the following features. The at least one ANR setting may include at least one of a coefficient setting of the first digital filter, a selection of a type of digital filter from among a plurality of available types of digital filters for the first digital filter, an interconnection of the first pathway, and the first data transfer rate. The ANR circuit may further include a processing device and a storage in which is stored a sequence of instructions that when executed by the processing device, causes the processing device to maintain the first, second and third ANR settings buffers within the storage and monitor digital data representing sounds flowing through the first pathway for an indication of instability in the ANR circuit. The ANR circuit may further include a VGA incorporated into the first pathway, wherein the at least one ANR setting comprises a gain setting of the VGA. The ANR circuit may further include an interface by which the ANR circuit is able to be coupled to an external processing device from which the at least one ANR setting is received. The ANR circuit may further include a first filter block incorporated into the first pathway, wherein the first filter block comprises a plurality of digital filters including the first digital filter; the first filter block is configurable to cause the first digital filter and other digital filters of the first filter block to cooperate to implement a transfer function; and the at least one ANR setting comprises a specification of the transfer function. The ANR circuit may further include a second ADC, a second digital filter, and a second pathway within the ANR circuit through which digital data representing sounds flows from the second ADC to the DAC through at least the second digital filter at a second data transfer rate through at least part of the second pathway; wherein the first and second pathways are combined at a first location along the first pathway and at a second location along the second pathway; and wherein the at least one ANR setting comprises at least one of a specification of where the first location is along the first pathway and a specification of where the second location is along the second pathway.

In one aspect, a method of configuring at least one ANR setting of an ANR circuit having a first pathway through which digital data representing sounds flows from a first ADC to a DAC through at least a first digital filter and at a first data transfer rate through at least part of the first pathway includes: alternately employing a first ANR settings buffer and a second ANR settings buffer to configure the at least one ANR setting in synchronization with a transfer of a piece of digital data transferred through at least part of the first pathway at the first data transfer rate; storing at least one failsafe ANR setting in a third ANR settings buffer; and employing the third ANR settings buffer to configure the at least one ANR setting in response to an instance of instability being detected in the ANR circuit.

Implementations may include, and are not limited to, one or more of the following features. The method may further include storing the at least one ANR setting in one of the first and second ANR settings buffers to configure at least one of a coefficient setting of the first digital filter, a selection of a type of digital filter from among a plurality of available types of digital filters for the first digital filter, an interconnection of the first pathway, the first data transfer rate, a gain setting of a VGA incorporated into the first pathway, and a transfer function implemented by a filter block comprising a plurality of digital filters including the first digital filter. The method may further include awaiting receipt of the at least one ANR setting from an external processing device coupled to an interface of the ANR circuit and storing the at least one ANR setting in one of the first and second ANR settings buffers. The method may further include storing a failsafe gain setting for a VGA incorporated into a pathway in the third ANR settings buffer; monitoring a signal output by the DAC; and employing the third ANR settings buffer to configure the VGA with the failsafe gain setting in response to detecting an indication of impending clipping in the signal output by the DAC as an indication of an instance of instability in the ANR circuit. The method may further include storing at least one ANR setting in one of the first and second ANR settings buffers; awaiting receipt of a signal by the ANR circuit; and employing the one of the first and second ANR settings buffers to configure the at least one ANR setting in response to receiving the ANR circuit receiving the signal.

Apparatus and method of an ANR circuit providing both feedforward-based and feedback-based ANR, possibly of a personal ANR device, compressing both feedforward and feedback reference sounds detected by feedforward and feedback microphones, respectively, in response to the acoustic energy of the feedforward reference noise sound reaching a predetermined level.

In another aspect, an ANR circuit includes a first VGA to compress a feedforward reference sound represented by a signal output by a feedforward microphone detecting an external noise sound in an environment external to a casing as the feedforward reference sound, a second VGA to compress a feedback reference sound represented by a signal output by a feedback microphone detecting a cavity noise sound within a cavity defined by the casing as the feedback reference sound, at least one filter to generate a feedforward anti-noise sound from the feedforward reference sound, at least another filter to generate a feedback anti-noise sound from the feedback reference sound, and a compression controller coupled to the first and second VGAs to operate the first and second VGAs to coordinate compression of the feedforward and feedback reference sounds in response to the acoustic energy of the external noise sound reaching a first threshold.

Implementations may include, and are not limited to, one or more of the following features. The first VGA may be an analog VGA interposed between the feedforward microphone and the at least one filter, and the compression controller monitors the acoustic energy of the external noise sound by monitoring the signal output by the feedforward microphone. The ANR may further include a first ADC to convert the signal output by the feedforward microphone from analog to digital form, wherein the first VGA may be a digital VGA interposed between first ADC and the at least one filter, and wherein the compression controller receives the signal from the feedforward microphone in digital form through the first ADC to monitor the acoustic energy of the external noise sound. The ANR may further include a DAC to convert a combination of the feedforward and feedback anti-noise sounds from being represented with digital data to being represented by an analog signal to be conveyed to an audio amplifier to drive an acoustic driver to acoustically output the combination of feedforward and feedback anti-noise sounds into the cavity, wherein the compression controller receives the digital data representing the combination of the feedforward and feedback anti-noise sounds, and the compression controller is structured to determine that the acoustic energy of the external noise sound reaches the first threshold in response to the amplitude of the combination of the feedforward and feedback anti-noise sounds reaching another threshold. The ANR circuit may further include an audio amplifier outputting an analog signal representing a combination of the feedforward and feedback anti-noise sounds to an acoustic driver to cause the acoustic driver to acoustically output the combination of the feedforward and feedback anti-noise sounds into the cavity, wherein the compression controller monitors the analog signal output by the audio amplifier and representing the combination of the feedforward and feedback anti-noise sounds, and the compression controller is structured to determine that the acoustic energy of the external noise sound reaches the first threshold in response to the amplitude of the analog signal representing the combination of the feedforward and feedback anti-noise sounds reaching another threshold. The ANR may further include a DAC to convert a combination of the feedforward and feedback anti-noise sounds from being represented with digital data to being represented by an analog signal to be conveyed to an audio amplifier to drive an acoustic driver to acoustically output the combination of feedforward and feedback anti-noise sounds into the cavity, wherein the compression controller monitors the analog signal output by the DAC, and the compression controller is structured to determine that the acoustic energy of the external noise sound reaches the first threshold in response to detecting an occurrence of an audio artifact in the analog signal. The ANR circuit may further include an audio amplifier outputting an analog signal representing a combination of the feedforward and feedback anti-noise sounds to an acoustic driver to cause the acoustic driver to acoustically output the combination of the feedforward and feedback anti-noise sounds into the cavity, wherein the compression controller monitors the analog signal output by the audio amplifier, and the compression controller is structured to determine that the acoustic energy of the external noise sound reaches the first threshold in response to detecting an occurrence of an audio artifact in the analog signal. The compression controller may operate the first VGA to compress the feedforward reference sound to an increasingly greater degree than the compression controller operates the second VGA to compress the feedback reference sound as the acoustic energy of the external noise sound rises further above the first threshold.

The compression controller may be structured to change the first threshold in response to a change in what audible frequency is predominant in the external noise sound. Further, the compression controller may be structured to lower the first threshold in response to what audible frequency is predominant in the external noise sound changing from a higher audible frequency to a lower audible frequency, and wherein the controller raises the first threshold in response to what audible frequency is predominant in the external noise sound changing from a lower audible frequency to a higher audible frequency.

The compression controller may be structured to operate the first VGA and the second VGA to compress both the feedforward and feedback reference sounds in response to the acoustic energy of the external noise sound reaching the first threshold, and to operate the first VGA to compress the feedforward reference sound and operates the second VGA to refrain from compressing the feedback reference sound in response to the acoustic energy of the external noise sound remaining below the first threshold while rising above a second threshold, where the second threshold is lower than the first threshold. Further, the compression controller may be structured to operate the first VGA to compress the feedforward reference sound to an increasingly greater degree as the acoustic energy of the external noise sound rises further above the first threshold until the firsts VGA is operated to have a gain close to zero, and to operate the second VGA to compress the feedback reference sound to an increasingly greater degree as the acoustic energy of the external noise sound rises further above the first threshold and without regard to whether or not the first VGA has been operated to have a gain close to zero. Further, the compression controller may be structured to operate the first VGA to compress the feedforward reference sound to an increasingly greater degree as the acoustic energy of the external noise sound rises further above the first threshold until the acoustic energy reaches a third threshold, and to operate the second VGA to compress the feedback reference sound to an increasingly greater degree as the acoustic energy of the external noise sound rises further above the first threshold and without regard to whether or not the acoustic energy of the external noise sound rises above the third threshold, where the third threshold is higher than the first threshold.

In another aspect, a personal ANR device includes a first casing defining a first cavity structured to be acoustically coupled to a first ear canal of a first ear of a user of the personal ANR device; a first feedforward microphone carried by the first casing in a manner that acoustically couples the first feedforward microphone to an environment external to the first casing to detect a first external noise sound in the environment external to the first casing, and structured to output a signal representing the first external noise sound as a first feedforward reference sound; a first feedback microphone disposed within the first cavity to detect a cavity noise sound within the first cavity, and structured to output a signal representing the cavity noise sound as a first feedback reference sound; a first acoustic driver disposed within the first casing to acoustically output a first feedforward anti-noise sound and first feedback anti-noise sound into the first cavity; and a first ANR circuit coupled to the first feedforward microphone to receive the signal representing the first feedforward reference sound, coupled to the first feedback microphone to receive the signal the representing first feedback reference sound, and coupled to the first acoustic driver to drive the first acoustic driver to acoustically output the first feedforward and first feedback anti-noise sounds; wherein the first ANR circuit is structured to generate the first feedforward anti-noise sound from the first feedforward reference sound, structured to generate the first feedback anti-noise sound from the first feedback reference sound, and structured to coordinate compression of the first feedforward and first feedback reference sounds in response to the acoustic energy of the first external noise sound reaching a first threshold.

Implementations may include, and are not limited to, one or more of the following features. The ANR circuit may be structured to compress the first feedforward reference sound to an increasingly greater degree than the ANR circuit compresses the first feedback reference sound as the acoustic energy of the first external noise sound rises further above the first threshold.

The ANR circuit may be structured to change the first threshold in response to a change in what audible frequency is predominant in the first external noise sound. Further, the ANR circuit may be structured to lower the first threshold in response to what audible frequency is predominant in the external noise sound changing from a higher audible frequency to a lower audible frequency, and to raise the first threshold in response to what audible frequency is predominant in the external noise sound changing from a lower audible frequency to a higher audible frequency.

The ANR circuit may be structured to compress both the first feedforward and first feedback reference sounds in response to the acoustic energy of the first external noise sound reaching the first threshold, and to compress the feedforward reference sound and refrains from compressing the first feedback reference sound in response to the acoustic energy of the first external noise sound remaining below the first threshold while rising above a second threshold, where the second threshold is lower than the first threshold. Further, the ANR circuit may be structured to compress the feedforward reference sound to an increasingly greater degree as the acoustic energy of the first external noise sound rises further above the first threshold until the feedforward reference has been compressed to a degree where the feedforward reference sound has been reduced in amplitude to close to zero, and to compress the feedback reference sound to an increasingly greater degree as the acoustic energy of the first external noise sound rises further above the first threshold and without regard to whether or not the feedforward reference sound has been reduced in amplitude to close to zero.

The personal ANR device may further include a second casing defining a second cavity structured to be acoustically coupled to a second ear canal of a second ear of the user; a second feedforward microphone carried by the second casing in a manner that acoustically couples the second feedforward microphone to an environment external to the second casing to detect a second external noise sound in the environment external to the second casing, and structured to output a signal representing the second external noise sound as a second feedforward reference sound; a second feedback microphone disposed within the second cavity to detect a cavity noise sound within the second cavity, and structured to output a signal representing the cavity noise sound as a second feedback reference sound; and a second acoustic driver disposed within the second casing to acoustically output a second feedforward anti-noise sound and second feedback anti-noise sound into the second cavity. Further, the personal ANR device may further include a second ANR circuit coupled to the second feedforward microphone to receive the signal representing the second feedforward reference sound, coupled to the second feedback microphone to receive the signal the representing second feedback reference sound, and coupled to the second acoustic driver to drive the second acoustic driver to acoustically output the second feedforward and second feedback anti-noise sounds; wherein the second ANR circuit is structured to generate the second feedforward anti-noise sound from the second feedforward reference sound, structured to generate the second feedback anti-noise sound from the second feedback reference sound, and structured to coordinate compression of the second feedforward and second feedback reference sounds in response to the acoustic energy of the second external noise sound reaching the first threshold. Further, the first ANR circuit may be coupled to the second feedforward microphone to receive the signal representing the second feedforward reference sound, coupled to the second feedback microphone to receive the signal the representing second feedback reference sound, and coupled to the second acoustic driver to drive the second acoustic driver to acoustically output the second feedforward and second feedback anti-noise sounds; and the first ANR circuit may be structured to generate the second feedforward anti-noise sound from the second feedforward reference sound, and structured to generate the second feedback anti-noise sound from the second feedback reference sound. Still further, the first ANR circuit may be structured to coordinate compression of the second feedforward and second feedback reference sounds in response to the acoustic energy of the second external noise sound reaching the first threshold. Still further, the first ANR circuit may be structured to coordinate compression of the first feedforward, the first feedback, the second feedforward and the second feedback reference sounds in response to the acoustic energy of the first external noise sound reaching the first threshold.

Apparatus and method of an ANR circuit detecting instances of instability in at least the provision of feedback-based ANR, monitoring audio that includes feedback anti-noise sounds for acoustic output by an acoustic driver for a sound having characteristics indicative of instability including at least a frequency within a range of frequencies and an amplitude reaching at least a predetermined minimum amplitude, and perhaps also a sinusoidal waveform.

In one aspect, a method of detecting instability in providing feedback-based ANR includes monitoring audio that comprises feedback anti-noise sounds employed in providing the feedback-based ANR for a sound having a frequency within a predetermined range of frequencies and having an amplitude that at least meets a predetermined minimum amplitude, wherein the combination of the range of predetermined frequencies and the predetermined amplitude is associated with sounds indicative of instability.

Implementations may include, and are not limited to, one or more of the following features. The method may further include monitoring the audio that comprises feedback anti-noise sounds employed in providing the feedback-based ANR for a sound having a sinusoidal waveform in addition to having a frequency within the predetermined range of frequencies and having an amplitude that at least meets the predetermined minimum amplitude. Monitoring audio that comprises feedback anti-noise sounds may include monitoring audio to be acoustically output by an acoustic driver to employ the feedback anti-noise sounds in providing the feedback-based ANR. The method may further include monitoring an amount of electric power drawn by an audio amplifier employed in amplifying the audio that comprises feedback anti-noise sounds for an instance of the amount of electric power drawn by the audio amplifier at least meeting a predetermined minimum level of electric power; wherein the combination of the range of predetermined frequencies, the predetermined amplitude is associated with sounds indicative of instability, and the predetermined minimum level of electric power is associated with sounds indicative of instability. The method may further include deriving the predetermined range of frequencies from an electrical characteristic of at least one component employed in providing the feedback-based ANR and from an acoustic characteristic of at least one other component employed in providing the feedback-based ANR.

Monitoring audio that comprises feedback anti-noise sounds may include configuring a phase-locked loop to lock onto a sound having a frequency within the predetermined range of frequencies and an amplitude at least meeting the predetermined minimum amplitude; monitoring audio to be acoustically output by an acoustic driver that comprises the feedback anti-noise sounds with the PLL; and awaiting an instance of the PLL locking onto a sound. The method may further include routing the audio monitored by the PLL through a first high-pass filter. The method may further include routing the audio from the first high-pass filter through a summing node configured to subtract pass-through audio that has been routed through a second high-pass filter before providing the audio to the PLL.

Monitoring audio that comprises feedback anti-noise sounds may include configuring a first band-pass filter to pass sounds of the audio that comprises feedback anti-noise sounds having a frequency within the predetermined range of frequencies; calculating a root mean square of the sounds that pass through the first band-pass filter, and comparing the root mean square of the sounds that pass through the first band-pass filter to the predetermined minimum amplitude. Monitoring audio that comprises feedback anti-noise sounds may further include configuring a PLL to lock onto a sound having a frequency within the predetermined range of frequencies and an amplitude at least meeting the predetermined minimum amplitude; monitoring the sounds that pass through the first band-pass filter with the PLL; and awaiting an instance of the PLL locking onto a sound. Monitoring audio that comprises feedback anti-noise sounds may further include configuring a second band-pass filter to pass sounds of audio comprising at least one of pass-through audio and feedforward anti-noise sounds having a frequency within the predetermined range of frequencies; calculating a root mean square of the sounds that pass through the second band-pass filter; and comparing the root mean square of the sounds that pass through the second band-pass filter to results of comparing the root mean square of the sounds that pass through the first band-pass filter to the predetermined minimum amplitude.

In one aspect, a personal ANR device providing at least feedback-based ANR to attenuate environmental noise sounds at a location adjacent and ear of a user of the personal ANR device includes an ANR circuit to derive at least feedback anti-noise sounds in providing the feedback-based ANR, an acoustic driver coupled to the ANR circuit to acoustically output audio that comprises the feedback anti-noise sounds, and a compression controller incorporated into the ANR circuit to monitor the audio acoustically output by the acoustic driver for a sound having a frequency within a predetermined range of frequencies and having an amplitude that at least meets a predetermined minimum amplitude, wherein the combination of the range of predetermined frequencies and the predetermined amplitude is associated with sounds indicative of instability.

Implementations may include, and are not limited to, one or more of the following features. The compression controller may further monitor the audio acoustically output by the acoustic driver for a sound having a sinusoidal waveform in addition to having a frequency within the predetermined range of frequencies and having an amplitude that at least meets the predetermined minimum amplitude.

The compression controller may include a PLL configurable to monitor the audio acoustically output by the acoustic driver and to lock onto a sound within the audio acoustically output by the acoustic driver having a frequency within the predetermined range of frequencies and an amplitude at least meeting the predetermined minimum amplitude. The compression controller may further include a first high-pass filter through which the audio to be acoustically output by the acoustic driver is routed before being monitored by the PLL. The compression controller may further include a second high-pass filter through which pass-through audio received by the ANR circuit is routed, and a summing node through which the audio to be acoustically output by the acoustic driver is routed after being routed through the first high-pass filter, and from which the pass-through audio routed through the second high-pass filter is subtracted before being monitored by the PLL.

The compression controller may include a first band-pass filter configurable to pass sounds of the audio acoustically output by the acoustic driver having a frequency within the predetermined range of frequencies, a first RMS block to calculate a root mean square of the sounds that pass through the first band-pass filter, and a first comparator to compare the root mean square calculated by the RMS block to the predetermined minimum amplitude. The compression controller may further include a PLL to monitor the sounds that pass through the first band-pass filter and to lock onto a sound having a frequency within the predetermined range of frequencies and an amplitude at least meeting the predetermined minimum amplitude. The compression controller may further include a second band-pass filter configurable to pass sounds of audio comprising at least one of pass-through audio and feedforward anti-noise sounds having a frequency within the predetermined range of frequencies, a second RMS block to calculate a root mean square of the sounds that pass through the second band-pass filter, and a second comparator to compare the root mean square calculated by the second RMS block to results of comparing the root mean square calculated by the first RMS block to the predetermined minimum amplitude.

Other features and advantages of the invention will be apparent from the description and claims that follow.

DETAILED DESCRIPTION

What is disclosed and what is claimed herein is intended to be applicable to a wide variety of personal ANR devices, i.e., devices that are structured to be at least partly worn by a user in the vicinity of at least one of the user's ears to provide ANR functionality for at least that one ear. It should be noted that although various specific implementations of personal ANR devices, such as headphones, two-way communications headsets, earphones, earbuds, wireless headsets (also known as "earsets") and ear protectors are presented with some degree of detail, such presentations of specific implementations are intended to facilitate understanding through the use of examples, and should not be taken as limiting either the scope of disclosure or the scope of claim coverage.

It is intended that what is disclosed and what is claimed herein is applicable to personal ANR devices that provide two-way audio communications, one-way audio communications (i.e., acoustic output of audio electronically provided by another device), or no communications, at all. It is intended that what is disclosed and what is claimed herein is applicable to personal ANR devices that are wirelessly connected to other devices, that are connected to other devices through electrically and/or optically conductive cabling, or that are not connected to any other device, at all. It is intended that what is disclosed and what is claimed herein is applicable to personal ANR devices having physical configurations structured to be worn in the vicinity of either one or both ears of a user, including and not limited to, headphones with either one or two earpieces, over-the-head headphones, behind-the-neck headphones, headsets with communications microphones (e.g., boom microphones), wireless headsets (i.e., earsets), single earphones or pairs of earphones, as well as hats or helmets incorporating one or two earpieces to enable audio communications and/or ear protection. Still other physical configurations of personal ANR devices to which what is disclosed and what is claimed herein are applicable will be apparent to those skilled in the art.

Beyond personal ANR devices, what is disclosed and claimed herein is also meant to be applicable to the provision of ANR in relatively small spaces in which a person may sit or stand, including and not limited to, phone booths, car passenger cabins, etc.

Figure 1:
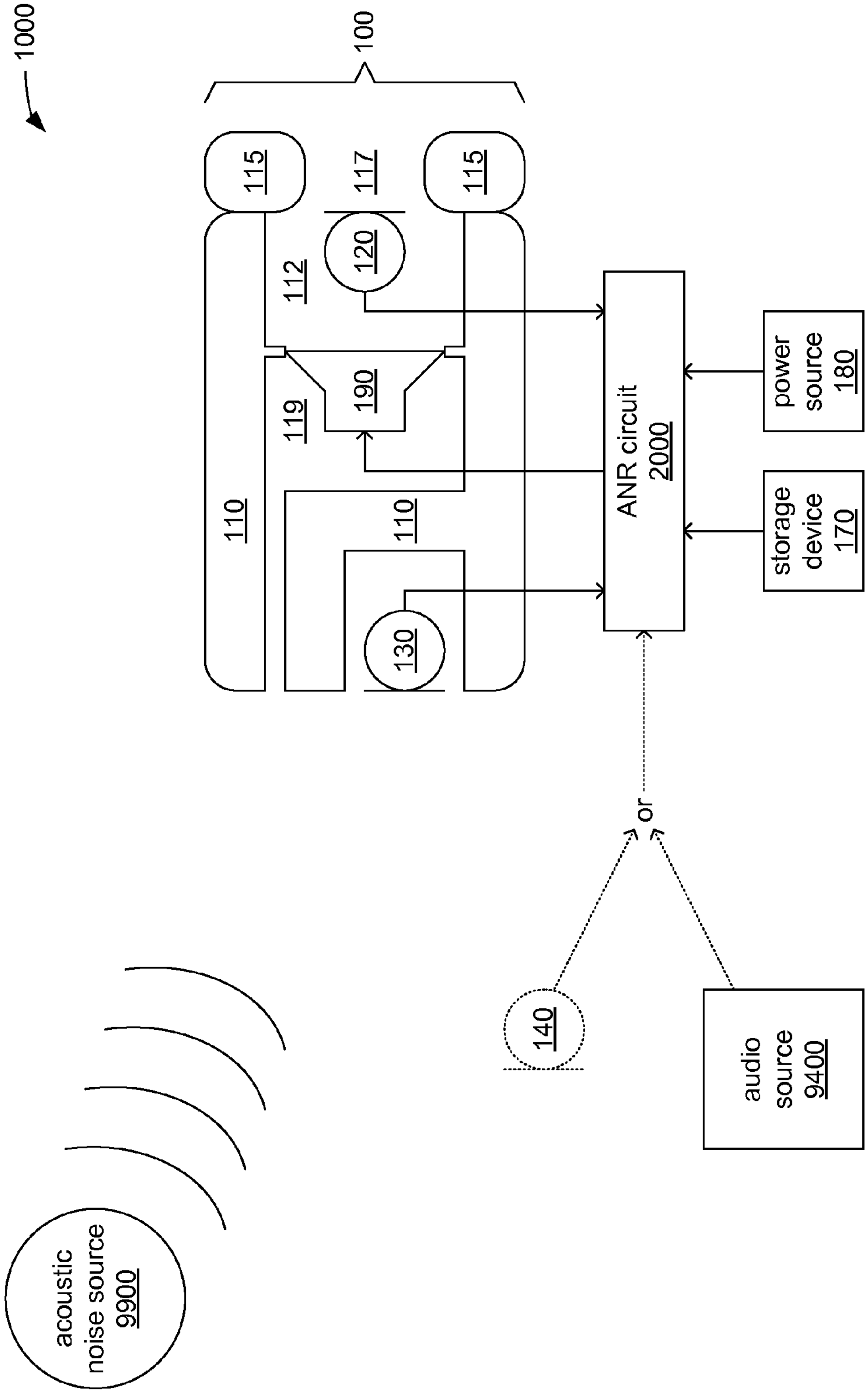
FIG. 1 is a block diagram of portions of an implementation of a personal ANR device.
Figure 2B:
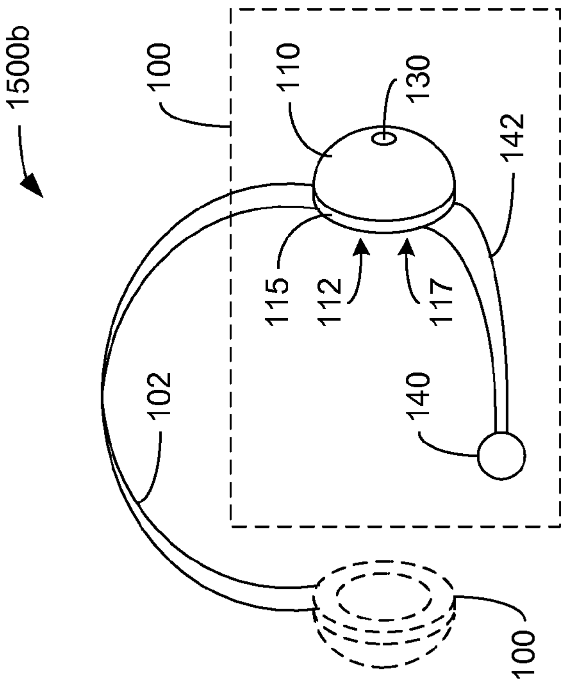
FIGS. 2*a* through 2*f* depict possible physical configurations of the personal ANR device of FIG. 1.

FIG. 1 provides a block diagram of a personal ANR device 1000 structured to be worn by a user to provide active noise reduction (ANR) in the vicinity of at least one of the user's ears. As will also be explained in greater detail, the personal ANR device 1000 may have any of a number of physical configurations, some possible ones of which are depicted in FIGS. 2*a* through 2*f*. Some of these depicted physical configurations incorporate a single earpiece 100 to provide ANR to only one of the user's ears, and others incorporate a pair of earpieces 100 to provide ANR to both of the user's ears. However, it should be noted that for the sake of simplicity of discussion, only a single earpiece 100 is depicted and described in relation to FIG. 1. As will also be explained in greater detail, the personal ANR device 1000 incorporates at least one ANR circuit 2000 that may provide either or both of feedback-based ANR and feedforward-based ANR, in addition to possibly further providing pass-through audio. FIGS. 3*a* and 3*b* depict a couple of possible internal architectures of the ANR circuit 2000 that are at least partly dynamically configurable. Further, FIGS. 4*a* through 4*e* depict some possible signal processing topologies and FIGS. 5*a* through 5*e* depict some possible filter block topologies that may the ANR circuit 2000 maybe dynamically configured to adopt. Further, the provision of either or both of feedback-based ANR and feedforward-based ANR is in addition to at least some degree of passive noise reduction (PNR) provided by the structure of each earpiece 100. Still further, FIGS. 6*a* through 6*c* depict various forms of triple-buffering that may be employed in dynamically configuring signal processing topologies, filter block topologies and/or still other ANR settings.

Each earpiece 100 incorporates a casing 110 having a cavity 112 at least partly defined by the casing 110 and by at least a portion of an acoustic driver 190 disposed within the casing to acoustically output sounds to a user's ear. This manner of positioning the acoustic driver 190 also partly defines another cavity 119 within the casing 110 that is separated from the cavity 112 by the acoustic driver 190. The casing 110 carries an ear coupling 115 surrounding an opening to the cavity 112 and having a passage 117 that is formed through the ear coupling 115 and that communicates with the opening to the cavity 112. In some implementations, an acoustically transparent screen, grill or other form of perforated panel (not shown) may be positioned in or near the passage 117 in a manner that obscures the cavity and/or the passage 117 from view for aesthetic reasons and/or to protect components within the casing 110 from damage. At times when the earpiece 100 is worn by a user in the vicinity of one of the user's ears, the passage 117 acoustically couples the cavity 112 to the ear canal of that ear, while the ear coupling 115 engages portions of the ear to form at least some degree of acoustic seal therebetween. This acoustic seal enables the casing 110, the ear coupling 115 and portions of the user's head surrounding the ear canal (including portions of the ear) to cooperate to acoustically isolate the cavity 112, the passage 117 and the ear canal from the environment external to the casing 110 and the user's head to at least some degree, thereby providing some degree of PNR.

In some variations, the cavity 119 may be coupled to the environment external to the casing 110 via one or more acoustic ports (only one of which is shown), each tuned by their dimensions to a selected range of audible frequencies to enhance characteristics of the acoustic output of sounds by the acoustic driver 190 in a manner readily recognizable to those skilled in the art. Also, in some variations, one or more tuned ports (not shown) may couple the cavities 112 and 119, and/or may couple the cavity 112 to the environment external to the casing 110. Although not specifically depicted, screens, grills or other forms of perforated or fibrous structures may be positioned within one or more of such ports to prevent passage of debris or other contaminants therethrough and/or to provide a selected degree of acoustic resistance therethrough.

In implementations providing feedforward-based ANR, a feedforward microphone 130 is disposed on the exterior of the casing 110 (or on some other portion of the personal ANR device 1000) in a manner that is acoustically accessible to the environment external to the casing 110. This external positioning of the feedforward microphone 130 enables the feedforward microphone 130 to detect environmental noise sounds, such as those emitted by an acoustic noise source 9900, in the environment external to the casing 110 without the effects of any form of PNR or ANR provided by the personal ANR device 1000. As those familiar with feedforward-based ANR will readily recognize, these sounds detected by the feedforward microphone 130 are used as a reference from which feedforward anti-noise sounds are derived and then acoustically output into the cavity 112 by the acoustic driver 190. The derivation of the feedforward anti-noise sounds takes into account the characteristics of the PNR provided by the personal ANR device 1000, characteristics and position of the acoustic driver 190 relative to the feedforward microphone 130, and/or acoustic characteristics of the cavity 112 and/or the passage 117. The feedforward anti-noise sounds are acoustically output by the acoustic driver 190 with amplitudes and time shifts calculated to acoustically interact with the noise sounds of the acoustic noise source 9900 that are able to enter into the cavity 112, the passage 117 and/or an ear canal in a subtractive manner that at least attenuates them.

In implementations providing feedback-based ANR, a feedback microphone 120 is disposed within the cavity 112. The feedback microphone 120 is positioned in close proximity to the opening of the cavity 112 and/or the passage 117 so as to be positioned close to the entrance of an ear canal when the earpiece 100 is worn by a user. The sounds detected by the feedback microphone 120 are used as a reference from which feedback anti-noise sounds are derived and then acoustically output into the cavity 112 by the acoustic driver 190. The derivation of the feedback anti-noise sounds takes into account the characteristics and position of the acoustic driver 190 relative to the feedback microphone 120, and/or the acoustic characteristics of the cavity 112 and/or the passage 117, as well as considerations that enhance stability in the provision of feedback-based ANR. The feedback anti-noise sounds are acoustically output by the acoustic driver 190 with amplitudes and time shifts calculated to acoustically interact with noise sounds of the acoustic noise source 9900 that are able to enter into the cavity 112, the passage 117 and/or the ear canal (and that have not been attenuated by whatever PNR) in a subtractive manner that at least attenuates them.

The personal ANR device 1000 further incorporates one of the ANR circuit 2000 associated with each earpiece 100 of the personal ANR device 1000 such that there is a one-to-one correspondence of ANR circuits 2000 to earpieces 100. Either a portion of or substantially all of each ANR circuit 2000 may be disposed within the casing 110 of its associated earpiece 100. Alternatively and/or additionally, a portion of or substantially all of each ANR circuit 2000 may be disposed within another portion of the personal ANR device 1000. Depending on whether one or both of feedback-based ANR and feedforward-based ANR are provided in an earpiece 100 associated with the ANR circuit 2000, the ANR circuit 2000 is coupled to one or both of the feedback microphone 120 and the feedforward microphone 130, respectively. The ANR circuit 2000 is further coupled to the acoustic driver 190 to cause the acoustic output of anti-noise sounds.

In some implementations providing pass-through audio, the ANR circuit 2000 is also coupled to an audio source 9400 to receive pass-through audio from the audio source 9400 to be acoustically output by the acoustic driver 190. The pass-through audio, unlike the noise sounds emitted by the acoustic noise source 9900, is audio that a user of the personal ANR device 1000 desires to hear. Indeed, the user may wear the personal ANR device 1000 to be able to hear the pass-through audio without the intrusion of the acoustic noise sounds. The pass-through audio may be a playback of recorded audio, transmitted audio, or any of a variety of other forms of audio that the user desires to hear. In some implementations, the audio source 9400 may be incorporated into the personal ANR device 1000, including and not limited to, an integrated audio playback component or an integrated audio receiver component. In other implementations, the personal ANR device 1000 incorporates a capability to be coupled either wirelessly or via an electrically or optically conductive cable to the audio source 9400 where the audio source 9400 is an entirely separate device from the personal ANR device 1000 (e.g., a CD player, a digital audio file player, a cell phone, etc.).

In other implementations pass-through audio is received from a communications microphone 140 integrated into variants of the personal ANR device 1000 employed in two-way communications in which the communications microphone 140 is positioned to detect speech sounds produced by the user of the personal ANR device 1000. In such implementations, an attenuated or otherwise modified form of the speech sounds produced by the user may be acoustically output to one or both ears of the user as a communications sidetone to enable the user to hear their own voice in a manner substantially similar to how they normally would hear their own voice when not wearing the personal ANR device 1000.

In support of the operation of at least the ANR circuit 2000, the personal ANR device 1000 may further incorporate one or both of a storage device 170, a power source 180 and/or a processing device (not shown). As will be explained in greater detail, the ANR circuit 2000 may access the storage device 170 (perhaps through a digital serial interface) to obtain ANR settings with which to configure feedback-based and/or feed-forward-based ANR. As will also be explained in greater detail, the power source 180 may be a power storage device of limited capacity (e.g., a battery).

FIGS. 2*a* through 2*f* depict various possible physical configurations that may be adopted by the personal ANR device 1000 of FIG. 1. As previously discussed, different implementations of the personal ANR device 1000 may have either one or two earpieces 100, and are structured to be worn on or near a user's head in a manner that enables each earpiece 100 to be positioned in the vicinity of a user's ear.

Figure 2A:
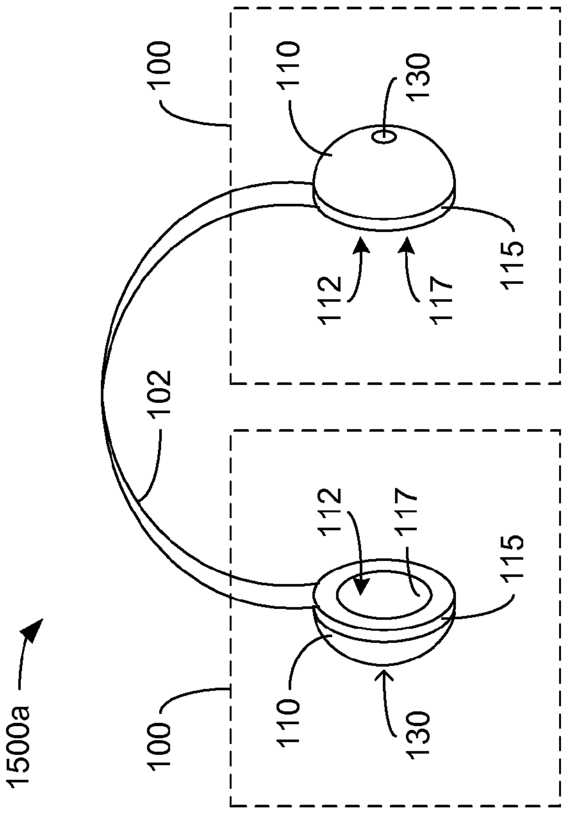
Figure 3A:
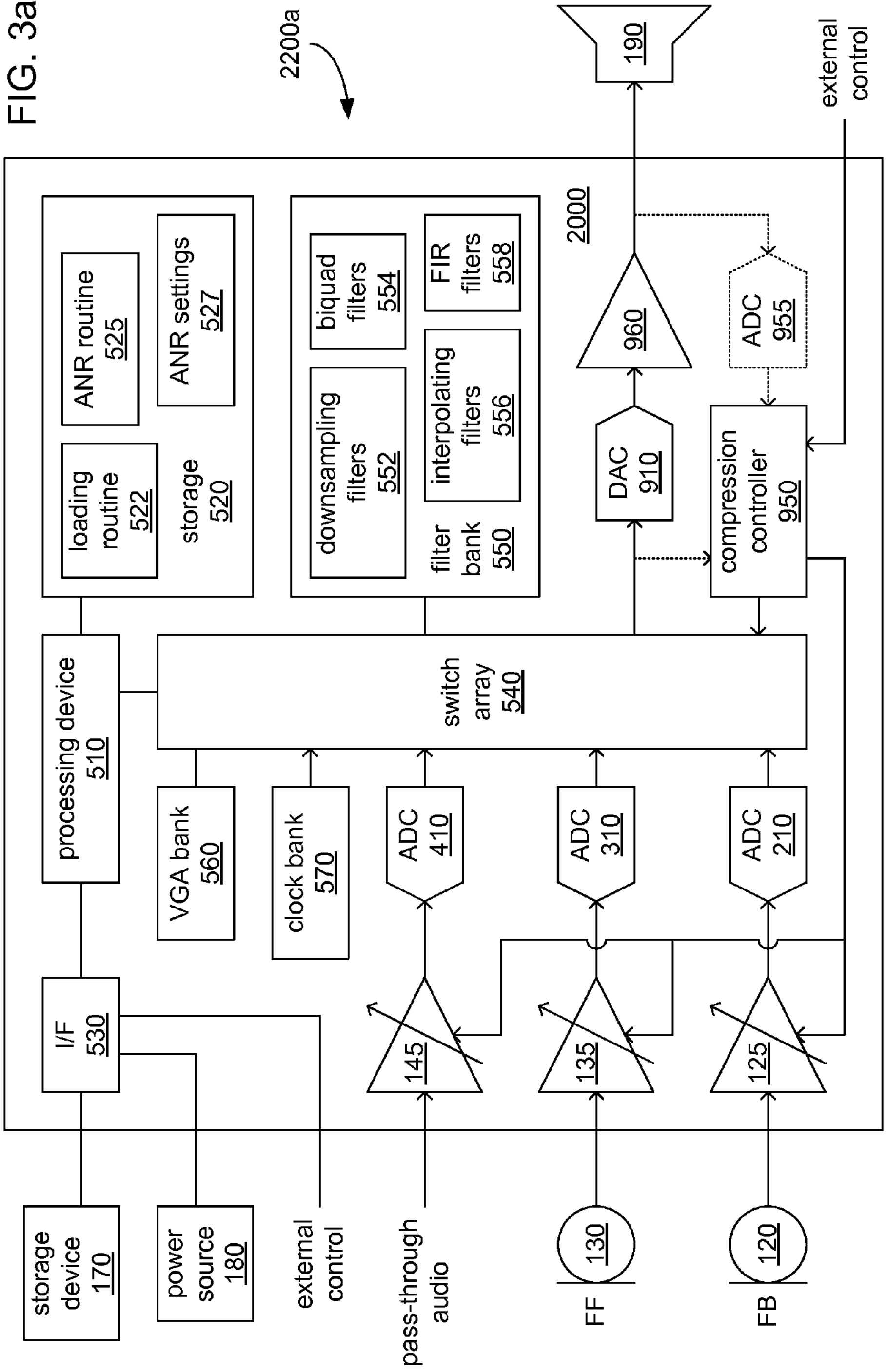
FIGS. 3*a* and 3*b* depict possible internal architectures of an ANR circuit of the personal ANR device of FIG. 1.
Figure 3B:
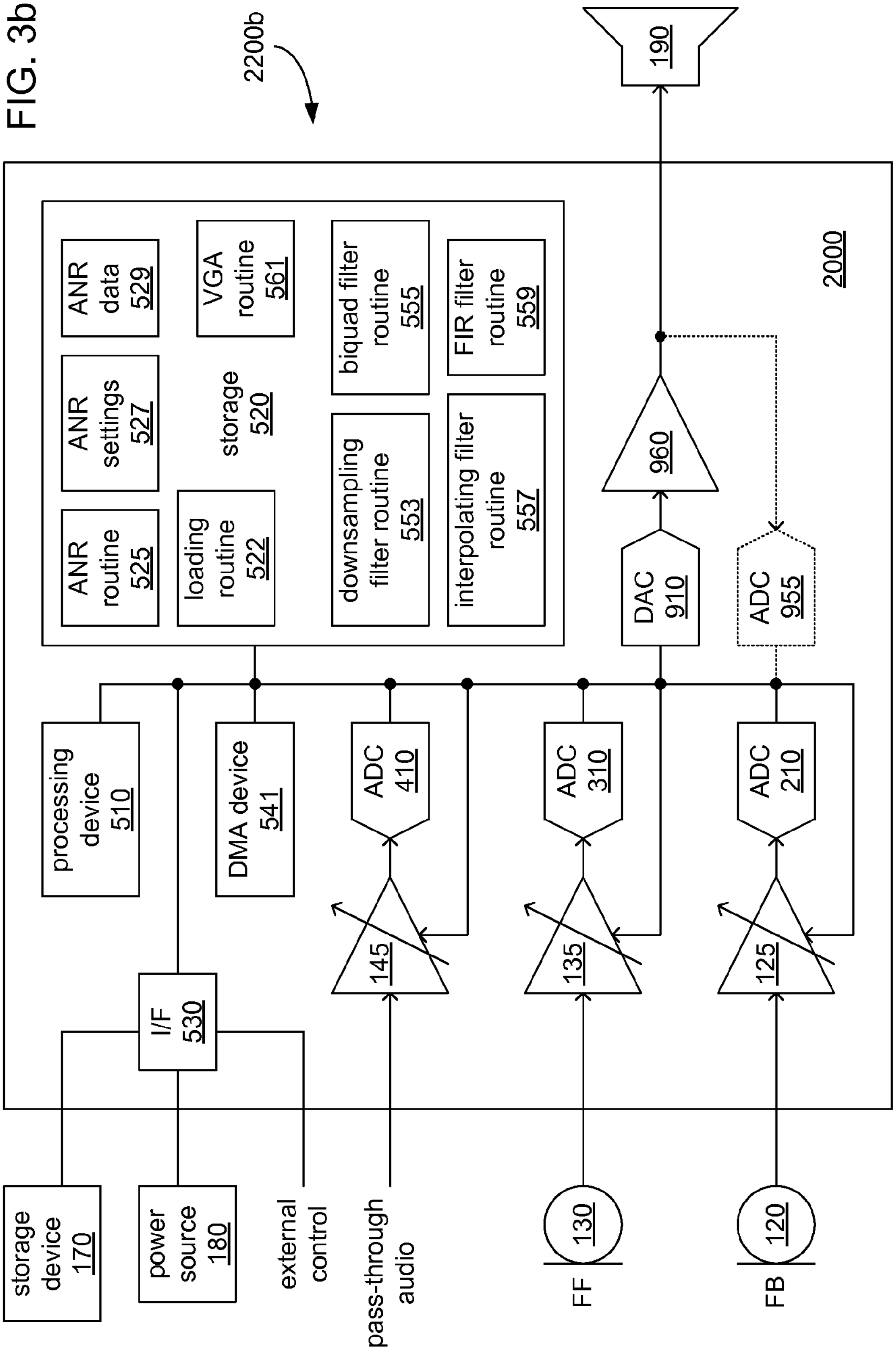

FIG. 2*a* depicts an "over-the-head" physical configuration 1500*a* of the personal ANR device 1000 that incorporates a pair of earpieces 100 that are each in the form of an earcup, and that are connected by a headband 102. However, and although not specifically depicted, an alternate variant of the physical configuration 1500*a* may incorporate only one of the earpieces 100 connected to the headband 102. Another alternate variant of the physical configuration 1500*a* may replace the headband 102 with a different band structured to be worn around the back of the head and/or the back of the neck of a user.

In the physical configuration 1500*a*, each of the earpieces 100 may be either an "on-ear" (also commonly called "supra-aural") or an "around-ear" (also commonly called "circum-aural") form of earcup, depending on their size relative to the pinna of a typical human ear. As previously discussed, each earpiece 100 has the casing 110 in which the cavity 112 is formed, and that 110 carries the ear coupling 115. In this physical configuration, the ear coupling 115 is in the form of a flexible cushion (possibly ring-shaped) that surrounds the periphery of the opening into the cavity 112 and that has the passage 117 formed therethrough that communicates with the cavity 112.

Where the earpieces 100 are structured to be worn as over-the-ear earcups, the casing 110 and the ear coupling 115 cooperate to substantially surround the pinna of an ear of a user. Thus, when such a variant of the personal ANR device 1000 is correctly worn, the headband 102 and the casing 110 cooperate to press the ear coupling 115 against portions of a side of the user's head surrounding the pinna of an ear such that the pinna is substantially hidden from view. Where the earpieces 100 are structured to be worn as on-ear earcups, the casing 110 and ear coupling 115 cooperate to overlie peripheral portions of a pinna that surround the entrance of an associated ear canal. Thus, when correctly worn, the headband 102 and the casing 110 cooperate to press the ear coupling 115 against portions of the pinna in a manner that likely leaves portions of the periphery of the pinna visible. The pressing of the flexible material of the ear coupling 115 against either portions of a pinna or portions of a side of a head surrounding a pinna serves both to acoustically couple the ear canal with the cavity 112 through the passage 117, and to form the previously discussed acoustic seal to enable the provision of PNR.

FIG. 2*b* depicts another over-the-head physical configuration 1500*b* that is substantially similar to the physical configuration 1500*a*, but in which one of the earpieces 100 additionally incorporates a communications microphone 140 connected to the casing 110 via a microphone boom 142. When this particular one of the earpieces 100 is correctly worn, the microphone boom 142 extends from the casing 110 and generally alongside a portion of a cheek of a user to position the communications microphone 140 closer to the mouth of the user to detect speech sounds acoustically output from the user's mouth. However, and although not specifically depicted, an alternative variant of the physical configuration 1500*b* is possible in which the communications microphone 140 is more directly disposed on the casing 110, and the microphone boom 142 is a hollow tube that opens on one end in the vicinity of the user's mouth and on the other end in the vicinity of the communications microphone 140 to convey sounds from the vicinity of the user's mouth to the vicinity of the communications microphone 140.

FIG. 2*b* also depicts the other of the earpieces 100 with broken lines to make clear that still another variant of the physical configuration 1500*b* of the personal ANR device 1000 is possible that incorporates only the one of the earpieces 100 that incorporates the microphone boom 142 and the communications microphone 140. In such another variant, the headband 102 would still be present and would continue to be worn over the head of the user.

Figure 2D:
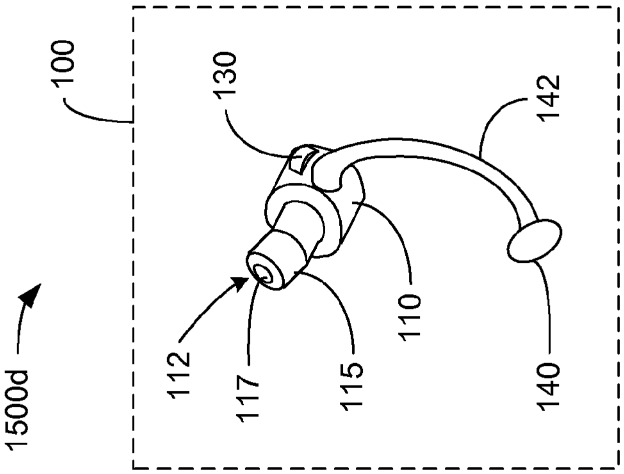
Figure 2C:
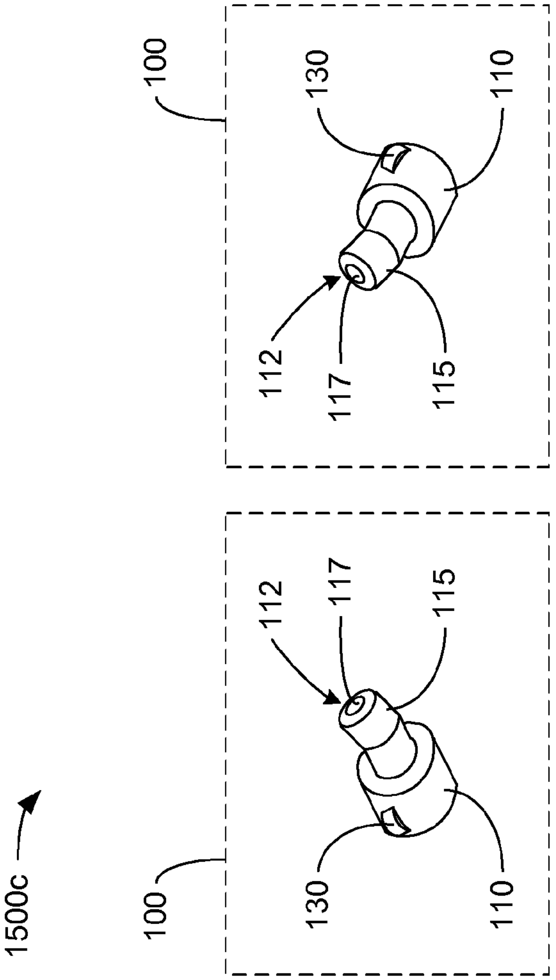

FIG. 2*c* depicts an "in-ear" (also commonly called "intra-aural") physical configuration 1500*c* of the personal ANR device 1000 that incorporates a pair of earpieces 100 that are each in the form of an in-ear earphone, and that may or may not be connected by a cord and/or by electrically or optically conductive cabling (not shown). However, and although not specifically depicted, an alternate variant of the physical configuration 1500*c* may incorporate only one of the earpieces 100.

As previously discussed, each of the earpieces 100 has the casing 110 in which the open cavity 112 is formed, and that carries the ear coupling 115. In this physical configuration, the ear coupling 115 is in the form of a substantially hollow tube-like shape defining the passage 117 that communicates with the cavity 112. In some implementations, the ear coupling 115 is formed of a material distinct from the casing 110 (possibly a material that is more flexible than that from which the casing 110 is formed), and in other implementations, the ear coupling 115 is formed integrally with the casing 110.

Portions of the casing 110 and/or of the ear coupling 115 cooperate to engage portions of the concha and/or the ear canal of a user's ear to enable the casing 110 to rest in the vicinity of the entrance of the ear canal in an orientation that acoustically couples the cavity 112 with the ear canal through the ear coupling 115. Thus, when the earpiece 100 is properly positioned, the entrance to the ear canal is substantially "plugged" to create the previously discussed acoustic seal to enable the provision of PNR.

FIG. 2*d* depicts another in-ear physical configuration 1500*d* of the personal ANR device 1000 that is substantially similar to the physical configuration 1500*c*, but in which one of the earpieces 100 is in the form of a single-ear headset (sometimes also called an "earset") that additionally incorporates a communications microphone 140 disposed on the casing 110. When this earpiece 100 is correctly worn, the communications microphone 140 is generally oriented towards the vicinity of the mouth of the user in a manner chosen to detect speech sounds produced by the user. However, and although not specifically depicted, an alternative variant of the physical configuration 1500*d* is possible in which sounds from the vicinity of the user's mouth are conveyed to the communications microphone 140 through a tube (not shown), or in which the communications microphone 140 is disposed on a boom (not shown) connected to the casing 110 and positioning the communications microphone 140 in the vicinity of the user's mouth.

Although not specifically depicted in FIG. 2*d*, the depicted earpiece 100 of the physical configuration 1500*d* having the communications microphone 140 may or may not be accompanied by another earpiece having the form of an in-ear earphone (such as one of the earpieces 100 depicted in FIG. 2*c*) that may or may not be connected to the earpiece 100 depicted in FIG. 2*d* via a cord or conductive cabling (also not shown).

Figure 2F:
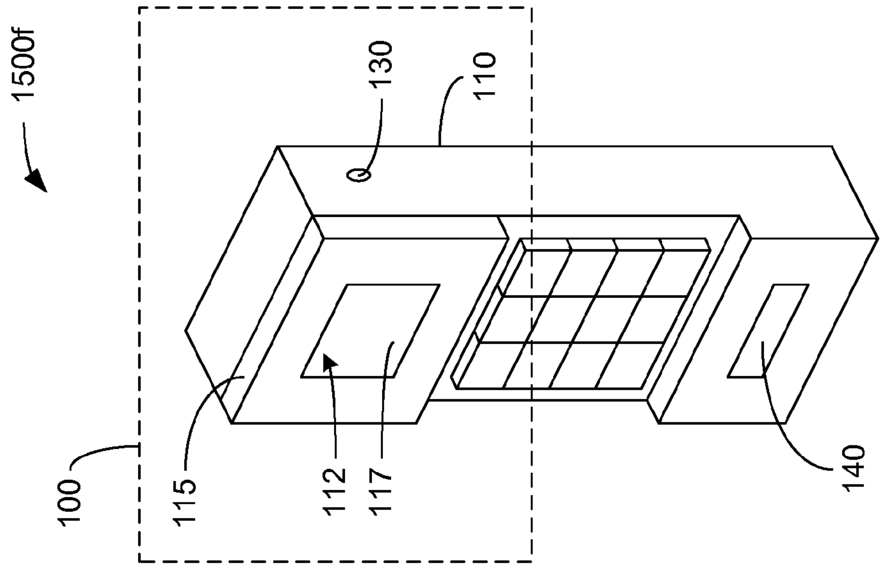
Figure 2E:
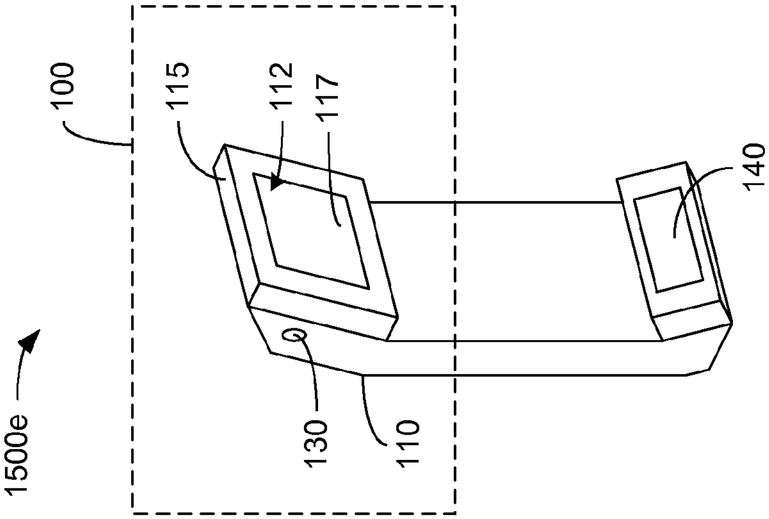

FIG. 2*e* depicts a two-way communications handset physical configuration 1500*e* of the personal ANR device 1000 that incorporates a single earpiece 100 that is integrally formed with the rest of the handset such that the casing 110 is the casing of the handset, and that may or may not be connected by conductive cabling (not shown) to a cradle base with which it may be paired. In a manner not unlike one of the earpieces 100 of an on-the-ear variant of either of the physical configurations 1500*a* and 1500*b*, the earpiece 100 of the physical configuration 1500*e* carries a form of the ear coupling 115 that is configured to be pressed against portions of the pinna of an ear to enable the passage 117 to acoustically couple the cavity 112 to an ear canal. In various possible implementations, ear coupling 115 may be formed of a material distinct from the casing 110, or may be formed integrally with the casing 110.

FIG. 2*f* depicts another two-way communications handset physical configuration 1500*f* of the personal ANR device 1000 that is substantially similar to the physical configuration 1500*e*, but in which the casing 110 is shaped somewhat more appropriately for portable wireless communications use, possibly incorporating user interface controls and/or display(s) to enable the dialing of phone numbers and/or the selection of radio frequency channels without the use of a cradle base.

FIGS. 3*a* and 3*b* depict possible internal architectures, either of which may be employed by the ANR circuit 2000 in implementations of the personal ANR device 1000 in which the ANR circuit 2000 is at least partially made up of dynamically configurable digital circuitry. In other words, the internal architectures of FIGS. 3*a* and 3*b* are dynamically configurable to adopt any of a wide variety of signal processing topologies and filter block topologies during operation of the ANR circuit 2000. FIGS. 4*a-g* depict various examples of signal processing topologies that may be adopted by the ANR circuit 2000 in this manner, and FIGS. 5*a-e* depict various examples of filter block topologies that may also be adopted by the ANR circuit 2000 for use within an adopted signal processing topology in this manner. However, and as those skilled in the art will readily recognize, other implementations of the personal ANR device 1000 are possible in which the ANR circuit 2000 is largely or entirely implemented with analog circuitry and/or digital circuitry lacking such dynamic configurability.

In implementations in which the circuitry of the ANR circuit 2000 is at least partially digital, analog signals representing sounds that are received or output by the ANR circuit 2000 may require conversion into or creation from digital data that also represents those sounds. More specifically, in both of the internal architectures 2200*a* and 2200*b*, analog signals received from the feedback microphone 120 and the feedforward microphone 130, as well as whatever analog signal representing pass-through audio may be received from either the audio source 9400 or the communications microphone 140, are digitized by analog-to-digital converters (ADCs) of the ANR circuit 2000. Also, whatever analog signal is provided to the acoustic driver 190 to cause the acoustic driver 190 to acoustically output anti-noise sounds and/or pass-through audio is created from digital data by a digital-to-analog converter (DAC) of the ANR circuit 2000. Further, either analog signals or digital data representing sounds may be manipulated to alter the amplitudes of those represented sounds by either analog or digital forms, respectively, of variable gain amplifiers (VGAs).

FIG. 3*a* depicts a possible internal architecture 2200*a* of the ANR circuit 2000 in which digital circuits that manipulate digital data representing sounds are selectively interconnected through one or more arrays of switching devices that enable those interconnections to be dynamically configured during operation of the ANR circuit 2000. Such a use of switching devices enables pathways for movement of digital data among various digital circuits to be defined through programming. More specifically, blocks of digital filters of varying quantities and/or types are able to be defined through which digital data associated with feedback-based ANR, feedforward-based ANR and pass-through audio are routed to perform these functions. In employing the internal architecture 2200*a*, the ANR circuit 2000 incorporates ADCs 210, 310 and 410; a processing device 510; a storage 520; an interface (I/F) 530; a switch array 540; a filter bank 550; and a DAC 910. Various possible variations may further incorporate one or more of analog VGAs 125, 135 and 145; a VGA bank 560; a clock bank 570; a compression controller 950; a further ADC 955; and/or an audio amplifier 960.

The ADC 210 receives an analog signal from the feedback microphone 120, the ADC 310 receives an analog signal from the feedforward microphone 130, and the ADC 410 receives an analog signal from either the audio source 9400 or the communications microphone 140. As will be explained in greater detail, one or more of the ADCs 210, 310 and 410 may receive their associated analog signals through one or more of the analog VGAs 125, 135 and 145, respectively. The digital outputs of each of the ADCs 210, 310 and 410 are coupled to the switch array 540. Each of the ADCs 210, 310 and 410 may be designed to employ a variant of the widely known sigma-delta analog-to-digital conversion algorithm for reasons of power conservation and inherent ability to reduce digital data representing audible noise sounds that might otherwise be introduced as a result of the conversion process. However, as those skilled in the art will readily recognize, any of a variety of other analog-to-digital conversion algorithms may be employed. Further, in some implementations, at least the ADC 410 may be bypassed and/or entirely dispensed with where at least the pass-through audio is provided to the ANR circuit 2000 as digital data, rather than as an analog signal.

The filter bank 550 incorporates multiple digital filters, each of which has its inputs and outputs coupled to the switch array 540. In some implementations, all of the digital filters within the filter bank 550 are of the same type, while in other implementations, the filter bank 550 incorporates a mixture of different types of digital filters. As depicted, the filter bank 550 incorporates a mixture of multiple downsampling filters 552, multiple biquadratic (biquad) filters 554, multiple interpolating filters 556, and multiple finite impulse response (FIR) filters 558, although other varieties of filters may be incorporated, as those skilled in the art will readily recognize. Further, among each of the different types of digital filters may be digital filters optimized to support different data transfer rates. By way of example, differing ones of the biquad filters 554 may employ coefficient values of differing bit-widths, or differing ones of the FIR filters 558 may have differing quantities of taps. The VGA bank 560 (if present) incorporates multiple digital VGAs, each of which has its inputs and outputs coupled to the switch array 540. Also, the DAC 910 has its digital input coupled to the switch array 540. The clock bank 570 (if present) provides multiple clock signal outputs coupled to the switch array 540 that simultaneously provide multiple clock signals for clocking data between components at selected data transfer rates and/or other purposes. In some implementations, at least a subset of the multiple clock signals are synchronized multiples of one another to simultaneously support different data transfer rates in different pathways in which the movement of data at those different data transfer rates in those different pathways is synchronized.

The switching devices of the switch array 540 are operable to selectively couple different ones of the digital outputs of the ADCs 210, 310 and 410; the inputs and outputs of the digital filters of the filter bank 550; the inputs and outputs of the digital VGAs of the VGA bank 560; and the digital input of the DAC 910 to form a set of interconnections therebetween that define a topology of pathways for the movement of digital data representing various sounds. The switching devices of the switch array 540 may also be operable to selectively couple different ones of the clock signal outputs of the clock bank 570 to different ones of the digital filters of the filter bank 550 and/or different ones of the digital VGAs of the VGA bank 560. It is largely in this way that the digital circuitry of the internal architecture 2200*a* is made dynamically configurable. In this way, varying quantities and types of digital filters and/or digital VGAs may be positioned at various points along different pathways defined for flows of digital data associated with feedback-based ANR, feedforward-based ANR and pass-through audio to modify sounds represented by the digital data and/or to derive new digital data representing new sounds in each of those pathways. Also, in this way, different data transfer rates may be selected by which digital data is clocked at different rates in each of the pathways.

In support of feedback-based ANR, feedforward-based ANR and/or pass-through audio, the coupling of the inputs and outputs of the digital filters within the filter bank 550 to the switch array 540 enables inputs and outputs of multiple digital filters to be coupled through the switch array 540 to create blocks of filters. As those skilled in the art will readily recognize, by combining multiple lower-order digital filters into a block of filters, multiple lower-order digital filters may be caused to cooperate to implement higher order functions without the use of a higher-order filter. Further, in implementations having a variety of types of digital filters, blocks of filters may be created that employ a mix of filters to perform a still greater variety of functions. By way of example, with the depicted variety of filters within the filter bank 550, a filter block (i.e., a block of filters) may be created having at least one of the downsampling filters 552, multiple ones of the biquad filters 554, at least one of the interpolating filters 556, and at least one of the FIR filters 558.

In some implementations, at least some of the switching devices of the switch array 540 may be implemented with binary logic devices enabling the switch array 540, itself, to be used to implement basic binary math operations to create summing nodes where pathways along which different pieces of digital data flow are brought together in a manner in which those different pieces of digital data are arithmetically summed, averaged, and/or otherwise combined. In such implementations, the switch array 540 may be based on a variant of dynamically programmable array of logic devices. Alternatively and/or additionally, a bank of binary logic devices or other form of arithmetic logic circuitry (not shown) may also be incorporated into the ANR circuit 2000 with the inputs and outputs of those binary logic devices and/or other form of arithmetic logic circuitry also being coupled to the switch array 540.

In the operation of switching devices of the switch array 540 to adopt a topology by creating pathways for the flow of data representing sounds, priority may be given to creating a pathway for the flow of digital data associated with feedback-based ANR that has as low a latency as possible through the switching devices. Also, priority may be given in selecting digital filters and VGAs that have as low a latency as possible from among those available in the filter bank 550 and the VGA bank 560, respectively. Further, coefficients and/or other settings provided to digital filters of the filter bank 550 that are employed in the pathway for digital data associated with feedback-based ANR may be adjusted in response to whatever latencies are incurred from the switching devices of the switch array 540 employed in defining the pathway. Such measures may be taken in recognition of the higher sensitivity of feedback-based ANR to the latencies of components employed in performing the function of deriving and/or acoustically outputting feedback anti-noise sounds. Although such latencies are also of concern in feedforward-based ANR, feedforward-based ANR is generally less sensitive to such latencies than feedback-based ANR. As a result, a degree of priority less than that given to feedback-based ANR, but greater than that given to pass-through audio, may be given to selecting digital filters and VGAs, and to creating a pathway for the flow of digital data associated with feedforward-based ANR.

The processing device 510 is coupled to the switch array 540, as well as to both the storage 520 and the interface 530. The processing device 510 may be any of a variety of types of processing device, including and not limited to, a general purpose central processing unit (CPU), a digital signal processor (DSP), a reduced instruction set computer (RISC) processor, a microcontroller, or a sequencer. The storage 520 may be based on any of a variety of data storage technologies, including and not limited to, dynamic random access memory (DRAM), static random access memory (SRAM), ferromagnetic disc storage, optical disc storage, or any of a variety of nonvolatile solid state storage technologies. Indeed, the storage 520 may incorporate both volatile and nonvolatile portions. Further, it will be recognized by those skilled in the art that although the storage 520 is depicted and discussed as if it were a single component, the storage 520 may be made up of multiple components, possibly including a combination of volatile and nonvolatile components. The interface 530 may support the coupling of the ANR circuit 2000 to one or more digital communications buses, including digital serial buses by which the storage device 170 (not to be confused with the storage 520) and/or other devices external to the ANR circuit 2000 (e.g., other processing devices, or other ANR circuits) may be coupled. Further, the interface 530 may provide one or more general purpose input/output (GPIO) electrical connections and/or analog electrical connections to support the coupling of manually-operable controls, indicator lights or other devices, such as a portion of the power source 180 providing an indication of available power.

In some implementations, the processing device 510 accesses the storage 520 to read a sequence of instructions of a loading routine 522, that when executed by the processing device 510, causes the processing device 510 to operate the interface 530 to access the storage device 170 to retrieve one or both of the ANR routine 525 and the ANR settings 527, and to store them in the storage 520. In other implementations, one or both of the ANR routine 525 and the ANR settings 527 are stored in a nonvolatile portion of the storage 520 such that they need not be retrieved from the storage device 170, even if power to the ANR circuit 2000 is lost.

Regardless of whether one or both of the ANR routine 525 and the ANR settings 527 are retrieved from the storage device 170, or not, the processing device 510 accesses the storage 520 to read a sequence of instructions of the ANR routine 525. The processing device 510 then executes that sequence of instructions, causing the processing device 510 to configure the switching devices of the switch array 540 to adopt a topology defining pathways for flows of digital data representing sounds and/or to provide differing clock signals to one or more digital filters and/or VGAs, as previously detailed. In some implementations, the processing device 510 is caused to configure the switching devices in a manner specified by a portion of the ANR settings 527, which the processing device 510 is also caused to read from the storage 520. Further, the processing device 510 is caused to set filter coefficients of various digital filters of the filter bank 550, gain settings of various VGAs of the VGA bank 560, and/or clock frequencies of the clock signal outputs of the clock bank 570 in a manner specified by a portion of the ANR settings 527.

In some implementations, the ANR settings 527 specify multiple sets of filter coefficients, gain settings, clock frequencies and/or configurations of the switching devices of the switch array 540, of which different sets are used in response to different situations. In other implementations, execution of sequences of instructions of the ANR routine 525 causes the processing device 510 to derive different sets of filter coefficients, gain settings, clock frequencies and/or switching device configurations in response to different situations. By way of example, the processing device 510 may be caused to operate the interface 530 to monitor a signal from the power source 180 that is indicative of the power available from the power source 180, and to dynamically switch between different sets of filter coefficients, gain settings, clock frequencies and/or switching device configurations in response to changes in the amount of available power.

By way of another example, the processing device 510 may be caused to monitor characteristics of sounds represented by digital data involved in feedback-based ANR, feedforward-based ANR and/or pass-through audio to determine whether or not it is desirable to alter the degree feedback-based and/or feedforward-based ANR provided. As will be familiar to those skilled in the art, while providing a high degree of ANR can be very desirable where there is considerable environmental noise to be attenuated, there can be other situations where the provision of a high degree of ANR can actually create a noisier or otherwise more unpleasant acoustic environment for a user of a personal ANR device than would the provision of less ANR. Therefore, the processing device 510 may be caused to alter the provision of ANR to adjust the degree of attenuation and/or the range of frequencies of environmental noise attenuated by the ANR provided in response to observed characteristics of one or more sounds. Further, as will also be familiar to those skilled in the art, where a reduction in the degree of attenuation and/or the range of frequencies is desired, it may be possible to simplify the quantity and/or type of filters used in implementing feedback-based and/or feedforward-based ANR, and the processing device 510 may be caused to dynamically switch between different sets of filter coefficients, gain settings, clock frequencies and/or switching device configurations to perform such simplifying, with the added benefit of a reduction in power consumption.

The DAC 910 is provided with digital data from the switch array 540 representing sounds to be acoustically output to an ear of a user of the personal ANR device 1000, and converts it to an analog signal representing those sounds. The audio amplifier 960 receives this analog signal from the DAC 910, and amplifies it sufficiently to drive the acoustic driver 190 to effect the acoustic output of those sounds.

The compression controller 950 (if present) monitors the sounds to be acoustically output for an indication of their amplitude being too high, indications of impending instances of clipping, actual instances of clipping, and/or other impending or actual instances of other audio artifacts. The compression controller 150 may either directly monitor digital data provided to the DAC 910 or the analog signal output by the audio amplifier 960 (through the ADC 955, if present). In response to such an indication, the compression controller 950 may alter gain settings of one or more of the analog VGAs 125, 135 and 145 (if present); and/or one or more of the VGAs of the VGA bank 560 placed in a pathway associated with one or more of the feedback-based ANR, feedforward-based ANR and pass-through audio functions to adjust amplitude, as will be explained in greater detail. Further, in some implementations, the compression controller 950 may also make such an adjustment in response to receiving an external control signal. Such an external signal may be provided by another component coupled to the ANR circuit 2000 to provide such an external control signal in response to detecting a condition such as an exceptionally loud environmental noise sound that may cause one or both of the feedback-based and feedforward-based ANR functions to react unpredictably.

FIG. 3*b* depicts another possible internal architecture 2200*b* of the ANR circuit 2000 in which a processing device accesses and executes stored machine-readable sequences of instructions that cause the processing device to manipulate digital data representing sounds in a manner that can be dynamically configured during operation of the ANR circuit 2000. Such a use of a processing device enables pathways for movement of digital data of a topology to be defined through programming. More specifically, digital filters of varying quantities and/or types are able to be defined and instantiated in which each type of digital filter is based on a sequence of instructions. In employing the internal architecture 2200*b*, the ANR circuit 2000 incorporates the ADCs 210, 310 and 410; the processing device 510; the storage 520; the interface 530; a direct memory access (DMA) device 540; and the DAC 910. Various possible variations may further incorporate one or more of the analog VGAs 125, 135 and 145; the ADC 955; and/or the audio amplifier 960. The processing device 510 is coupled directly or indirectly via one or more buses to the storage 520; the interface 530; the DMA device 540; the ADCs 210, 310 and 410; and the DAC 910 to at least enable the processing device 510 to control their operation. The processing device 510 may also be similarly coupled to one or more of the analog VGAs 125, 135 and 145 (if present); and to the ADC 955 (if present).

As in the internal architecture 2200*a*, the processing device 510 may be any of a variety of types of processing device, and once again, the storage 520 may be based on any of a variety of data storage technologies and may be made up of multiple components. Further, the interface 530 may support the coupling of the ANR circuit 2000 to one or more digital communications buses, and may provide one or more general purpose input/output (GPIO) electrical connections and/or analog electrical connections. The DMA device 540 may be based on a secondary processing device, discrete digital logic, a bus mastering sequencer, or any of a variety of other technologies.

Stored within the storage 520 are one or more of a loading routine 522, an ANR routine 525, ANR settings 527, ANR data 529, a downsampling filter routine 553, a biquad filter routine 555, an interpolating filter routine 557, a FIR filter routine 559, and a VGA routine 561. In some implementations, the processing device 510 accesses the storage 520 to read a sequence of instructions of the loading routine 522, that when executed by the processing device 510, causes the processing device 510 to operate the interface 530 to access the storage device 170 to retrieve one or more of the ANR routine 525, the ANR settings 527, the downsampling filter routine 553, the biquad filter routine 555, the interpolating filter routine 557, the FIR routine 559 and the VGA routine 561, and to store them in the storage 520. In other implementations, one or more of these are stored in a nonvolatile portion of the storage 520 such that they need not be retrieved from the storage device 170.

As was the case in the internal architecture 2200*a*, the ADC 210 receives an analog signal from the feedback microphone 120, the ADC 310 receives an analog signal from the feedforward microphone 130, and the ADC 410 receives an analog signal from either the audio source 9400 or the communications microphone 140 (unless the use of one or more of the ADCs 210, 310 and 410 is obviated through the direct receipt of digital data). Again, one or more of the ADCs 210, 310 and 410 may receive their associated analog signals through one or more of the analog VGAs 125, 135 and 145, respectively. As was also the case in the internal architecture 2200*a*, the DAC 910 converts digital data representing sounds to be acoustically output to an ear of a user of the personal ANR device 1000 into an analog signal, and the audio amplifier 960 amplifies this signal sufficiently to drive the acoustic driver 190 to effect the acoustic output of those sounds.

However, unlike the internal architecture 2200*a* where digital data representing sounds were routed via an array of switching devices, such digital data is stored in and retrieved from the storage 520. In some implementations, the processing device 510 repeatedly accesses the ADCs 210, 310 and 410 to retrieve digital data associated with the analog signals they receive for storage in the storage 520, and repeatedly retrieves the digital data associated with the analog signal output by the DAC 910 from the storage 520 and provides that digital data to the DAC 910 to enable the creation of that analog signal. In other implementations, the DMA device 540 (if present) transfers digital data among the ADCs 210, 310 and 410; the storage 520 and the DAC 910 independently of the processing device 510. In still other implementations, the ADCs 210, 310 and 410 and/or the DAC 910 incorporate "bus mastering" capabilities enabling each to write digital data to and/or read digital data from the storage 520 independently of the processing device 510. The ANR data 529 is made up of the digital data retrieved from the ADCs 210, 310 and 410, and the digital data provided to the DAC 910 by the processing device 510, the DMA device 540 and/or bus mastering functionality.

The downsampling filter routine 553, the biquad filter routine 555, the interpolating filter routine 557 and the FIR filter routine 559 are each made up of a sequence of instructions that cause the processing device 510 to perform a combination of calculations that define a downsampling filter, a biquad filter, an interpolating filter and a FIR filter, respectively. Further, among each of the different types of digital filters may be variants of those digital filters that are optimized for different data transfer rates, including and not limited to, differing bit widths of coefficients or differing quantities of taps. Similarly, the VGA routine 561 is made up of a sequence of instructions that cause the processing device 510 to perform a combination of calculations that define a VGA. Although not specifically depicted, a summing node routine may also be stored in the storage 520 made up of a sequence of instructions that similarly defines a summing node.

The ANR routine 525 is made up of a sequence of instructions that cause the processing device 510 to create a signal processing topology having pathways incorporating varying quantities of the digital filters and VGAs defined by the downsampling filter routine 553, the biquad filter routine 555, the interpolating filter routine 557, the FIR filter routine 559 and the VGA routine 561 to support feedback-based ANR, feedforward-based ANR and/or pass-through audio. The ANR routine 525 also causes the processing device 510 to perform the calculations defining each of the various filters and VGAs incorporated into that topology. Further, the ANR routine 525 either causes the processing device 510 to perform the moving of data among ADCs 210, 310 and 410, the storage 520 and the DAC 910, or causes the processing device 510 to coordinate the performance of such moving of data either by the DMA device 540 (if present) or by bus mastering operations performed by the ADCs 210, 310 and 410, and/or the DAC 910.

The ANR settings 527 is made up of data defining topology characteristics (including selections of digital filters), filter coefficients, gain settings, clock frequencies, data transfer rates and/or data sizes. In some implementations, the topology characteristics may also define the characteristics of any summing nodes to be incorporated into the topology. The processing device 510 is caused by the ANR routine 525 to employ such data taken from the ANR settings 527 in creating a signal processing topology (including selecting digital filters), setting the filter coefficients for each digital filter incorporated into the topology, and setting the gains for each VGA incorporated into the topology. The processing device 510 may be further caused by the ANR routine 525 to employ such data from the ANR settings 527 in setting clock frequencies and/or data transfer rates for the ADCs 210, 310 and 410; for the digital filters incorporated into the topology; for the VGAs incorporated into the topology; and for the DAC 910.

In some implementations, the ANR settings 527 specify multiple sets of topology characteristics, filter coefficients, gain settings, clock frequencies and/or data transfer rates, of which different sets are used in response to different situations. In other implementations, execution of sequences of instructions of the ANR routine 525 causes the processing device 510 to derive different sets of filter coefficients, gain settings, clock frequencies and/or data transfer rates for a given signal processing topology in different situations. By way of example, the processing device 510 may be caused to operate the interface 530 to monitor a signal from the power source 180 that is indicative of the power available from the power source 180, and to employ different sets of filter coefficients, gain settings, clock frequencies and/or data transfer rates in response to changes in the amount of available power.

By way of another example, the processing device 510 may be caused to alter the provision of ANR to adjust the degree of ANR required in response to observed characteristics of one or more sounds. Where a reduction in the degree of attenuation and/or the range of frequencies of noise sounds attenuated is possible and/or desired, it may be possible to simplify the quantity and/or type of filters used in implementing feedback-based and/or feedforward-based ANR, and the processing device 510 may be caused to dynamically switch between different sets of filter coefficients, gain settings, clock frequencies and/or data transfer rates to perform such simplifying, with the added benefit of a reduction in power consumption.

Therefore, in executing sequences of instructions of the ANR routine 525, the processing device 510 is caused to retrieve data from the ANR settings 527 in preparation for adopting a signal processing topology defining the pathways to be employed by the processing device 510 in providing feedback-based ANR, feedforward-based ANR and pass-through audio. The processing device 510 is caused to instantiate multiple instances of digital filters, VGAs and/or summing nodes, employing filter coefficients, gain settings and/or other data from the ANR settings 527. The processing device 510 is then further caused to perform the calculations defining each of those instances of digital filters, VGAs and summing nodes; to move digital data among those instances of digital filters, VGAs and summing nodes; and to at least coordinate the moving of digital data among the ADCs 210, 310 and 410, the storage 520 and the DAC 910 in a manner that conforms to the data retrieved from the ANR settings 527. At a subsequent time, the ANR routine 525 may cause the processing device 510 to change the signal processing topology, a digital filter, filter coefficients, gain settings, clock frequencies and/or data transfer rates during operation of the personal ANR device 1000. It is largely in this way that the digital circuitry of the internal architecture 2200*b* is made dynamically configurable. Also, in this way, varying quantities and types of digital filters and/or digital VGAs may be positioned at various points along a pathway of a topology defined for a flow of digital data to modify sounds represented by that digital data and/or to derive new digital data representing new sounds, as will be explained in greater detail.

In some implementations, the ANR routine 525 may cause the processing device 510 to give priority to operating the ADC 210 and performing the calculations of the digital filters, VGAs and/or summing nodes positioned along the pathway defined for the flow of digital data associated with feedback-based ANR. Such a measure may be taken in recognition of the higher sensitivity of feedback-based ANR to the latency between the detection of feedback reference sounds and the acoustic output of feedback anti-noise sounds.

The processing device 510 may be further caused by the ANR routine 525 to monitor the sounds to be acoustically output for indications of the amplitude being too high, clipping, indications of clipping about to occur, and/or other audio artifacts actually occurring or indications of being about to occur. The processing device 510 may be caused to either directly monitor digital data provided to the DAC 910 or the analog signal output by the audio amplifier 960 (through the ADC 955) for such indications. In response to such an indication, the processing device 510 may be caused to operate one or more of the analog VGAs 125, 135 and 145 to adjust at least one amplitude of an analog signal, and/or may be caused to operate one or more of the VGAs based on the VGA routine 561 and positioned within a pathway of a topology to adjust the amplitude of at least one sound represented by digital data, as will be explained in greater detail.

FIGS. 4*a* through 4*g* depict some possible signal processing topologies that may be adopted by the ANR circuit 2000 of the personal ANR device 1000 of FIG. 1. As previously discussed, some implementations of the personal ANR device 1000 may employ a variant of the ANR circuit 2000 that is at least partially programmable such that the ANR circuit 2000 is able to be dynamically configured to adopt different signal processing topologies during operation of the ANR circuit 2000. Alternatively, other implementations of the personal ANR device 1000 may incorporate a variant of the ANR circuit 2000 that is substantially inalterably structured to adopt one unchanging signal processing topology.

As previously discussed, separate ones of the ANR circuit 2000 are associated with each earpiece 100, and therefore, implementations of the personal ANR device 1000 having a pair of the earpieces 100 also incorporate a pair of the ANR circuits 2000. However, as those skilled in the art will readily recognize, other electronic components incorporated into the personal ANR device 1000 in support of a pair of the ANR circuits 2000, such as the power source 180, may not be duplicated. For the sake of simplicity of discussion and understanding, signal processing topologies for only a single ANR circuit 2000 are presented and discussed in relation to FIGS. 4*a*-*g*.

As also previously discussed, different implementations of the personal ANR device 1000 may provide only one of either feedback-based ANR or feedforward-based ANR, or may provide both. Further, different implementations may or may not additionally provide pass-through audio. Therefore, although signal processing topologies implementing all three of feedback-based ANR, feedforward-based ANR and pass-through audio are depicted in FIGS. 4*a*-*g*, it is to be understood that variants of each of these signal processing topologies are possible in which only one or the other of these two forms of ANR is provided, and/or in which pass-through audio is not provided. In implementations in which the ANR circuit 2000 is at least partially programmable, which of these two forms of ANR are provided and/or whether or not both forms of ANR are provided may be dynamically selectable during operation of the ANR circuit 2000.

Figure 4A:
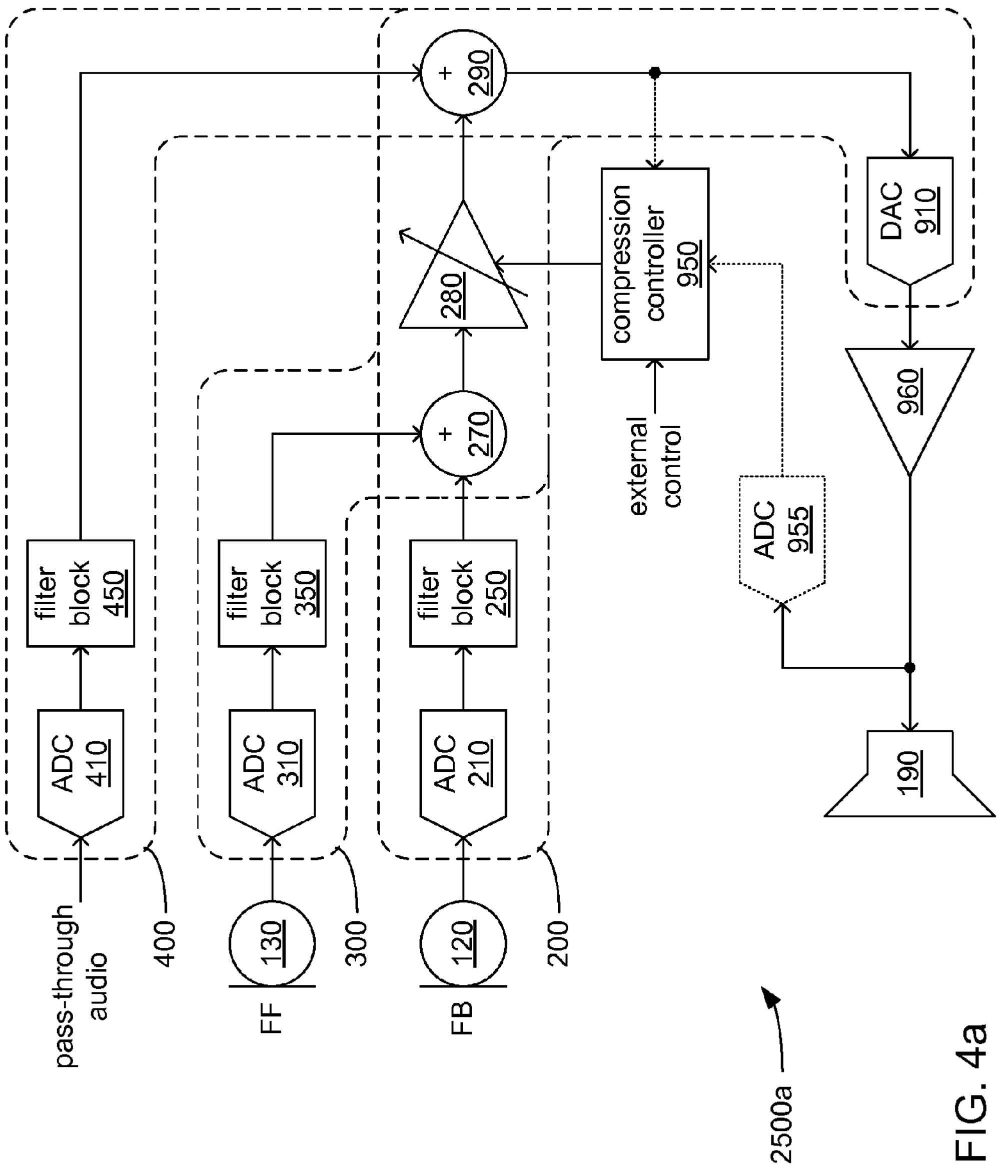
FIGS. 4*a* through 4*g* depict possible signal processing topologies that may be adopted by the ANR circuit of the personal ANR device of FIG. 1.

FIG. 4*a* depicts a possible signal processing topology 2500*a* for which the ANR circuit 2000 may be structured and/or programmed. Where the ANR circuit 2000 adopts the signal processing topology 2500*a*, the ANR circuit 2000 incorporates at least the DAC 910, the compression controller 950, and the audio amplifier 960. Depending, in part on whether one or both of feedback-based and feedforward-based ANR are supported, the ANR circuit 2000 further incorporates one or more of the ADCs 210, 310, 410 and/or 955; filter blocks 250, 350 and/or 450; and/or summing nodes 270 and/or 290.

Where the provision of feedback-based ANR is supported, the ADC 210 receives an analog signal from the feedback microphone 120 representing feedback reference sounds detected by the feedback microphone 120. The ADC 210 digitizes the analog signal from the feedback microphone 120, and provides feedback reference data corresponding to the analog signal output by the feedback microphone 120 to the filter block 250. One or more digital filters within the filter block 250 are employed to modify the data from the ADC 210 to derive feedback anti-noise data representing feedback anti-noise sounds. The filter block 250 provides the feedback anti-noise data to the VGA 280, possibly through the summing node 270 where feedforward-based ANR is also supported.

Where the provision of feedforward-based ANR is also supported, the ADC 310 receives an analog signal from the feedforward microphone 130, digitizes it, and provides feedforward reference data corresponding to the analog signal output by the feedforward microphone 130 to the filter block 350. One or more digital filters within the filter block 350 are employed to modify the feedforward reference data received from the ADC 310 to derive feedforward anti-noise data representing feedforward anti-noise sounds. The filter block 350 provides the feedforward anti-noise data to the VGA 280, possibly through the summing node 270 where feedback-based ANR is also supported.

At the VGA 280, the amplitude of one or both of the feedback and feedforward anti-noise sounds represented by the data received by the VGA 280 (either through the summing node 270, or not) may be altered under the control of the compression controller 950. The VGA 280 outputs its data (with or without amplitude alteration) to the DAC 910, possibly through the summing nodes 290 where talk-through audio is also supported.

In some implementations where pass-through audio is supported, the ADC 410 digitizes an analog signal representing pass-through audio received from the audio source 9400, the communications microphone 140 or another source and provides the digitized result to the filter block 450. In other implementations where pass-through audio is supported, the audio source 9400, the communications microphone 140 or another source provides digital data representing pass-through audio to the filter block 450 without need of analog-to-digital conversion. One or more digital filters within the filter block 450 are employed to modify the digital data representing the pass-through audio to derive a modified variant of the pass-through audio data in which the pass-through audio may be re-equalized and/or enhanced in other ways. The filter block 450 provides the pass-through audio data to the summing node 290 where the pass-through audio data is combined with the data being provided by the VGA 280 to the DAC 910.

The analog signal output by the DAC 910 is provided to the audio amplifier 960 to be amplified sufficiently to drive the acoustic driver 190 to acoustically output one or more of feedback anti-noise sounds, feedforward anti-noise sounds and pass-through audio. The compression controller 950 controls the gain of the VGA 280 to enable the amplitude of sound represented by data output by one or both of the filter blocks 250 and 350 to be reduced in response to indications of impending instances of clipping, actual occurrences of clipping and/or other undesirable audio artifacts being detected by the compression controller 950. The compression controller 950 may either monitor the data being provided to the DAC 910 by the summing node 290, or may monitor the analog signal output of the audio amplifier 960 through the ADC 955.

As further depicted in FIG. 4*a*, the signal processing topology 2500*a* defines multiple pathways along which digital data associated with feedback-based ANR, feedforward-based ANR and pass-through audio flow. Where feedback-based ANR is supported, the flow of feedback reference data and feedback anti-noise data among at least the ADC 210, the filter block 250, the VGA 280 and the DAC 910 defines a feedback-based ANR pathway 200. Similarly, where feedforward-based ANR is supported, the flow of feedforward reference data and feedforward anti-noise data among at least the ADC 310, the filter block 350, the VGA 280 and the DAC 910 defines a feedforward-based ANR pathway 300. Further, where pass-through audio is supported, the flow of pass-through audio data and modified pass-through audio data among at least the ADC 410, the filter block 450, the summing node 290 and the DAC 910 defines a pass-through audio pathway 400. Where both feedback-based and feedforward-based ANR are supported, the pathways 200 and 300 both further incorporate the summing node 270. Further, where pass-through audio is also supported, the pathways 200 and/or 300 incorporate the summing node 290.

In some implementations, digital data representing sounds may be clocked through all of the pathways 200, 300 and 400 that are present at the same data transfer rate. Thus, where the pathways 200 and 300 are combined at the summing node 270, and/or where the pathway 400 is combined with one or both of the pathways 200 and 300 at the summing node 400, all digital data is clocked through at a common data transfer rate, and that common data transfer rate may be set by a common synchronous data transfer clock. However, as is known to those skilled in the art and as previously discussed, the feedforward-based ANR and pass-through audio functions are less sensitive to latencies than the feedback-based ANR function. Further, the feedforward-based ANR and pass-through audio functions are more easily implemented with sufficiently high quality of sound with lower data sampling rates than the feedback-based ANR function. Therefore, in other implementations, portions of the pathways 300 and/or 400 may be operated at slower data transfer rates than the pathway 200. Preferably, the data transfer rates of each of the pathways 200, 300 and 400 are selected such that the pathway 200 operates with a data transfer rate that is an integer multiple of the data transfer rates selected for the portions of the pathways 300 and/or 400 that are operated at slower data transfer rates.

By way of example in an implementation in which all three of the pathways 200, 300 and 400 are present, the pathway 200 is operated at a data transfer rate selected to provide sufficiently low latency to enable sufficiently high quality of feedback-based ANR that the provision of ANR is not unduly compromised (e.g., by having anti-noise sounds out-of-phase with the noise sounds they are meant to attenuate, or instances of negative noise reduction such that more noise is actually being generated than attenuated, etc.), and/or sufficiently high quality of sound in the provision of at least the feedback anti-noise sounds. Meanwhile, the portion of the pathway 300 from the ADC 310 to the summing node 270 and the portion of the pathway 400 from the ADC 410 to the summing node 290 are both operated at lower data transfer rates (either the same lower data transfer rates or different ones) that still also enable sufficiently high quality of feedforward-based ANR in the pathway 300, and sufficiently high quality of sound in the provision of the feedforward anti-noise through the pathway 300 and/or pass-through audio through the pathway 400.

In recognition of the likelihood that the pass-through audio function may be even more tolerant of a greater latency and a lower sampling rate than the feedforward-based ANR function, the data transfer rate employed in that portion of the pathway 400 may be still lower than the data transfer rate of that portion of the pathway 300. To support such differences in transfer rates in one variation, one or both of the summing nodes 270 and 290 may incorporate sample-and-hold, buffering or other appropriate functionality to enable the combining of digital data received by the summing nodes 270 and 290 at different data transfer rates. This may entail the provision of two different data transfer clocks to each of the summing nodes 270 and 290. Alternatively, to support such differences in transfer rates in another variation, one or both of the filter blocks 350 and 450 may incorporate an upsampling capability (perhaps through the inclusion of an interpolating filter or other variety of filter incorporating an upsampling capability) to increase the data transfer rate at which the filter blocks 350 and 450 provide digital data to the summing nodes 270 and 290, respectively, to match the data transfer rate at which the filter block 250 provides digital data to the summing node 270, and subsequently, to the summing node 290.

It may be that in some implementations, multiple power modes may be supported in which the data transfer rates of the pathways 300 and 400 are dynamically altered in response to the availability of power from the power source 180 and/or in response to changing ANR requirements. More specifically, the data transfer rates of one or both of the pathway 300 and 400 up to the points where they are combined with the pathway 200 may be reduced in response to an indication of diminishing power being available from the power supply 180 and/or in response to the processing device 510 detecting characteristics in sounds represented by digital data indicating that the degree of attenuation and/or range of frequencies of noise sounds attenuated by the ANR provided can be reduced. In making determinations of whether or not such reductions in data transfer rates are possible, the processing device 510 may be caused to evaluate the effects of such reductions in data transfer rates on quality of sound through one or more of the pathways 200, 300 and 400, and/or the quality of feedback-based and/or feed-forward based ANR provided.

Figure 4B:
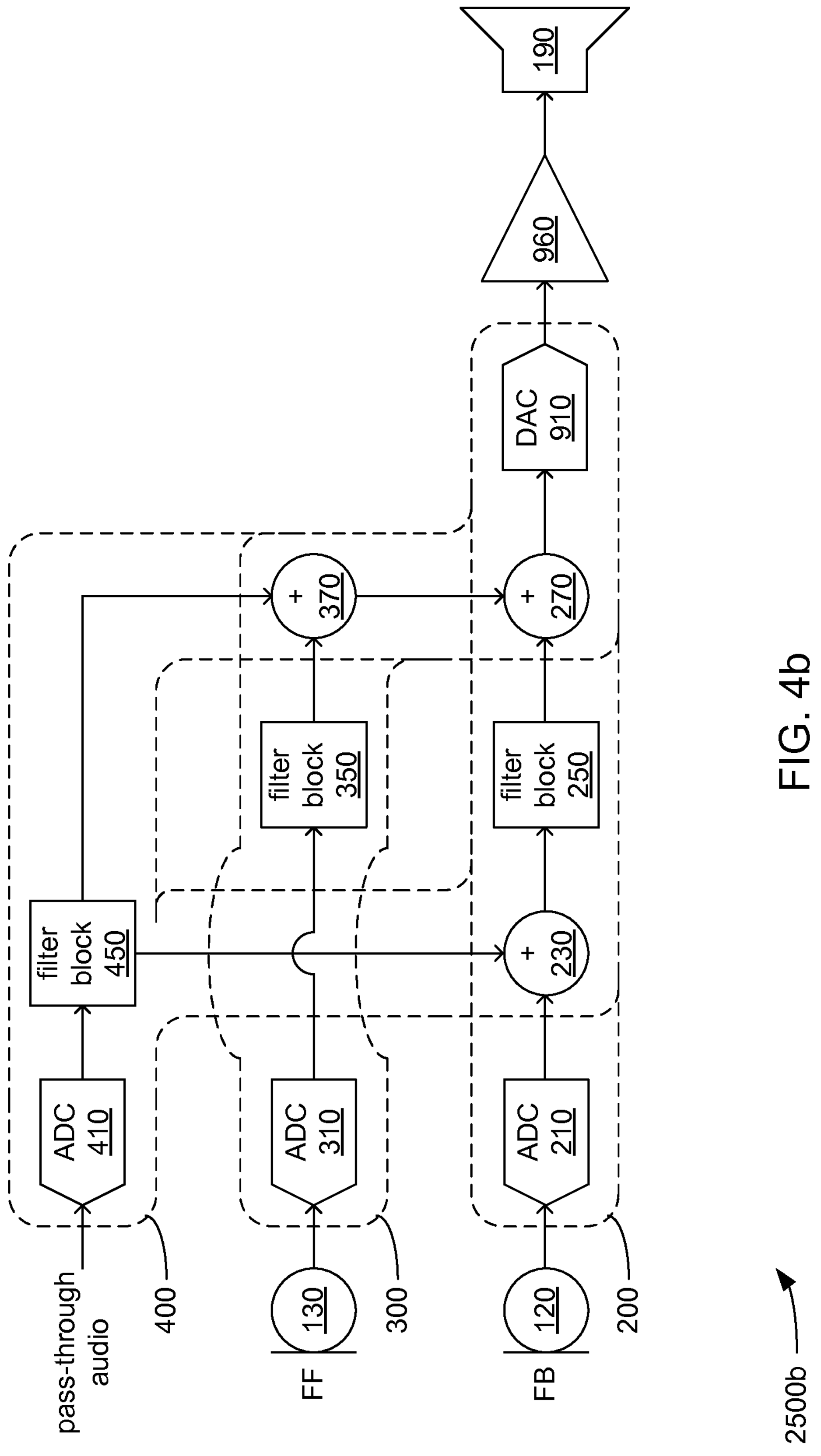

FIG. 4*b* depicts a possible signal processing topology 2500*b* for which the ANR circuit 2000 may be structured and/or programmed. Where the ANR circuit 2000 adopts the signal processing topology 2500*b*, the ANR circuit 2000 incorporates at least the DAC 910, the audio amplifier 960, the ADC 210, a pair of summing nodes 230 and 270, and a pair of filter blocks 250 and 450. The ANR circuit 2000 may further incorporate one or more of the ADC 410, the ADC 310, a filter block 350 and a summing node 370.

The ADC 210 receives and digitizes an analog signal from the feedback microphone 120 representing feedback reference sounds detected by the feedback microphone 120, and provides corresponding feedback reference data to the summing node 230. In some implementations, the ADC 410 digitizes an analog signal representing pass-through audio received from the audio source 9400, the communications microphone 140 or another source and provides the digitized result to the filter block 450. In other implementations, the audio source 9400, the communications microphone 140 or another source provides digital data representing pass-through audio to the filter block 450 without need of analog-to-digital conversion. One or more digital filters within the filter block 450 are employed to modify the digital data representing the pass-through audio to derive a modified variant of the pass-through audio data in which the pass-through audio may be re-equalized and/or enhanced in other ways. One or more digital filters within the filter block 450 also function as a crossover that divides the modified pass-through audio data into higher and lower frequency sounds, with data representing the higher frequency sounds being output to the summing node 270, and data representing the lower frequency sounds being output to the summing node 230. In various implementations, the crossover frequency employed in the filter block 450 is dynamically selectable during operation of the ANR circuit 2000, and may be selected to effectively disable the crossover function to cause data representing all frequencies of the modified pass-through audio to be output to either of the summing nodes 230 or 270. In this way, the point at which the modified pass-through audio data is combined with data for the feedback ANR function within the signal processing topology 2500*a* can be made selectable.

As just discussed, feedback reference data from the ADC 210 may be combined with data from the filter block 450 for the pass-through audio function (either the lower frequency sounds, or all of the modified pass-through audio) at the summing node 230. The summing node 230 outputs the possibly combined data to the filter block 250. One or more digital filters within the filter block 250 are employed to modify the data from summing node 230 to derive modified data representing at least feedback anti-noise sounds and possibly further-modified pass-through audio sounds. The filter block 250 provides the modified data to the summing node 270. The summing node 270 combines the data from the filter block 450 that possibly represents higher frequency sounds of the modified pass-through audio with the modified data from the filter block 250, and provides the result to the DAC 910 to create an analog signal. The provision of data by the filter block 450 to the summing node 270 may be through the summing node 370 where the provision of feedforward-based ANR is also supported.

Where the crossover frequency employed in the filter block 450 is dynamically selectable, various characteristics of the filters making up the filter block 450 may also be dynamically configurable. By way of example, the number and/or type of digital filters making up the filter block 450 may be dynamically alterable, as well as the coefficients for each of those digital filters. Such dynamic configurability may be deemed desirable to correctly accommodate changes among having no data from the filter block 450 being combined with feedback reference data from the ADC 210, having data from the filter block 450 representing lower frequency sounds being combined with feedback reference data from the ADC 210, and having data representing all of the modified pass-through audio from the filter block 450 being combined with feedback reference data from the ADC 210.

Where the provision of feedforward-based ANR is also supported, the ADC 310 receives an analog signal from the feedforward microphone 130, digitizes it, and provides feedforward reference data corresponding to the analog signal output by the feedforward microphone 130 to the filter block 350. One or more digital filters within the filter block 350 are employed to modify the feedforward reference data received from the ADC 310 to derive feedforward anti-noise data representing feedforward anti-noise sounds. The filter block 350 provides the feedforward anti-noise data to the summing node 370 where the feedforward anti-noise data is possibly combined with data that may be provided by the filter block 450 (either the higher frequency sounds, or all of the modified pass-through audio).

The analog signal output by the DAC 910 is provided to the audio amplifier 960 to be amplified sufficiently to drive the acoustic driver 190 to acoustically output one or more of feedback anti-noise sounds, feedforward anti-noise sounds and pass-through audio.

As further depicted in FIG. 4*b*, the signal processing topology 2500*b* defines its own variations of the pathways 200, 300 and 400 along which digital data associated with feedback-based ANR, feedforward-based ANR and pass-through audio, respectively, flow. In a manner not unlike the pathway 200 of the signal processing topology 2500*a*, the flow of feedback reference data and feedback anti-noise data among the ADC 210, the summing nodes 230 and 270, the filter block 250 and the DAC 910 defines the feedback-based ANR pathway 200 of the signal processing topology 2500*b*. Where feedforward-based ANR is supported, in a manner not unlike the pathway 300 of the signal processing topology 2500*a*, the flow of feedforward reference data and feedforward anti-noise data among the ADC 310, the filter block 350, the summing nodes 270 and 370, and the DAC 910 defines the feedforward-based ANR pathway 300 of the signal processing topology 2500*b*. However, in a manner very much unlike the pathway 400 of the signal processing topology 2500*a*, the ability of the filter block 450 of the signal processing topology 2500*b* to split the modified pass-through audio data into higher frequency and lower frequency sounds results in the pathway 400 of the signal processing topology 2500*b* being partially split. More specifically, the flow of digital data from the ADC 410 to the filter block 450 is split at the filter block 450. One split portion of the pathway 400 continues to the summing node 230, where it is combined with the pathway 200, before continuing through the filter block 250 and the summing node 270, and ending at the DAC 910. The other split portion of the pathway 400 continues to the summing node 370 (if present), where it is combined with the pathway 300 (if present), before continuing through the summing node 270 and ending at the DAC 910.

Also not unlike the pathways 200, 300 and 400 of the signal processing topology 2500*a*, the pathways 200, 300 and 400 of the signal processing topology 2500*b* may be operated with different data transfer rates. However, differences in data transfer rates between the pathway 400 and both of the pathways 200 and 300 would have to be addressed. Sample-and-hold, buffering or other functionality may be incorporated into each of the summing nodes 230, 270 and/or 370. Alternatively and/or additionally, the filter block 350 may incorporate interpolation or other upsampling capability in providing digital data to the summing node 370, and/or the filter block 450 may incorporate a similar capability in providing digital data to each of the summing nodes 230 and 370 (or 270, if the pathway 300 is not present).

Figure 4C:
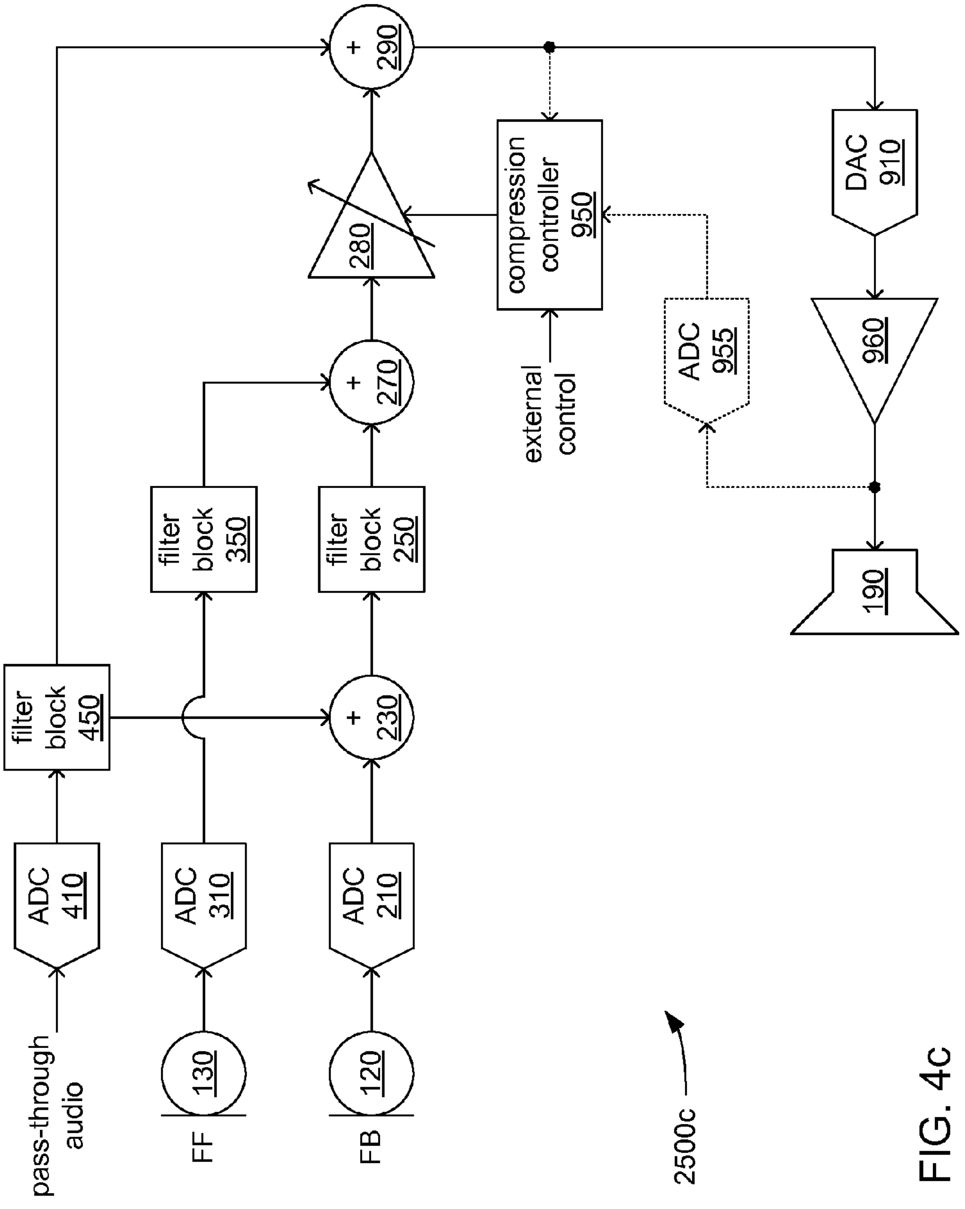

FIG. 4*c* depicts another possible signal processing topology 2500*c* for which the ANR circuit 2000 may be structured and/or programmed. Where the ANR circuit 2000 adopts the signal processing topology 2500*c*, the ANR circuit 2000 incorporates at least the DAC 910, the audio amplifier 960, the ADC 210, the summing node 230, the filter blocks 250 and 450, the VGA 280, another summing node 290, and the compressor 950. The ANR circuit 2000 may further incorporate one or more of the ADC 410, the ADC 310, the filter block 350, the summing node 270, and the ADC 955. The signal processing topologies 2500*b* and 2500*c* are similar in numerous ways. However, a substantial difference between the signal processing topologies 2500*b* and 2500*c* is the addition of the compressor 950 in the signal processing topology 2500*c* to enable the amplitudes of the sounds represented by data output by both of the filter blocks 250 and 350 to be reduced in response to the compressor 950 detecting actual instances or indications of impending instances of clipping and/or other undesirable audio artifacts.

The filter block 250 provides its modified data to the VGA 280 where the amplitude of the sounds represented by the data provided to the VGA 280 may be altered under the control of the compression controller 950. The VGA 280 outputs its data (with or without amplitude alteration) to the summing node 290, where it may be combined with data that may be output by the filter block 450 (perhaps the higher frequency sounds of the modified pass-through audio, or perhaps the entirety of the modified pass-through audio). In turn, the summing node 290 provides its output data to the DAC 910. Where the provision of feedforward-based ANR is also supported, the data output by the filter block 250 to the VGA 280 is routed through the summing node 270, where it is combined with the data output by the filter block 350 representing feedforward anti-noise sounds, and this combined data is provided to the VGA 280.

Figure 4D:
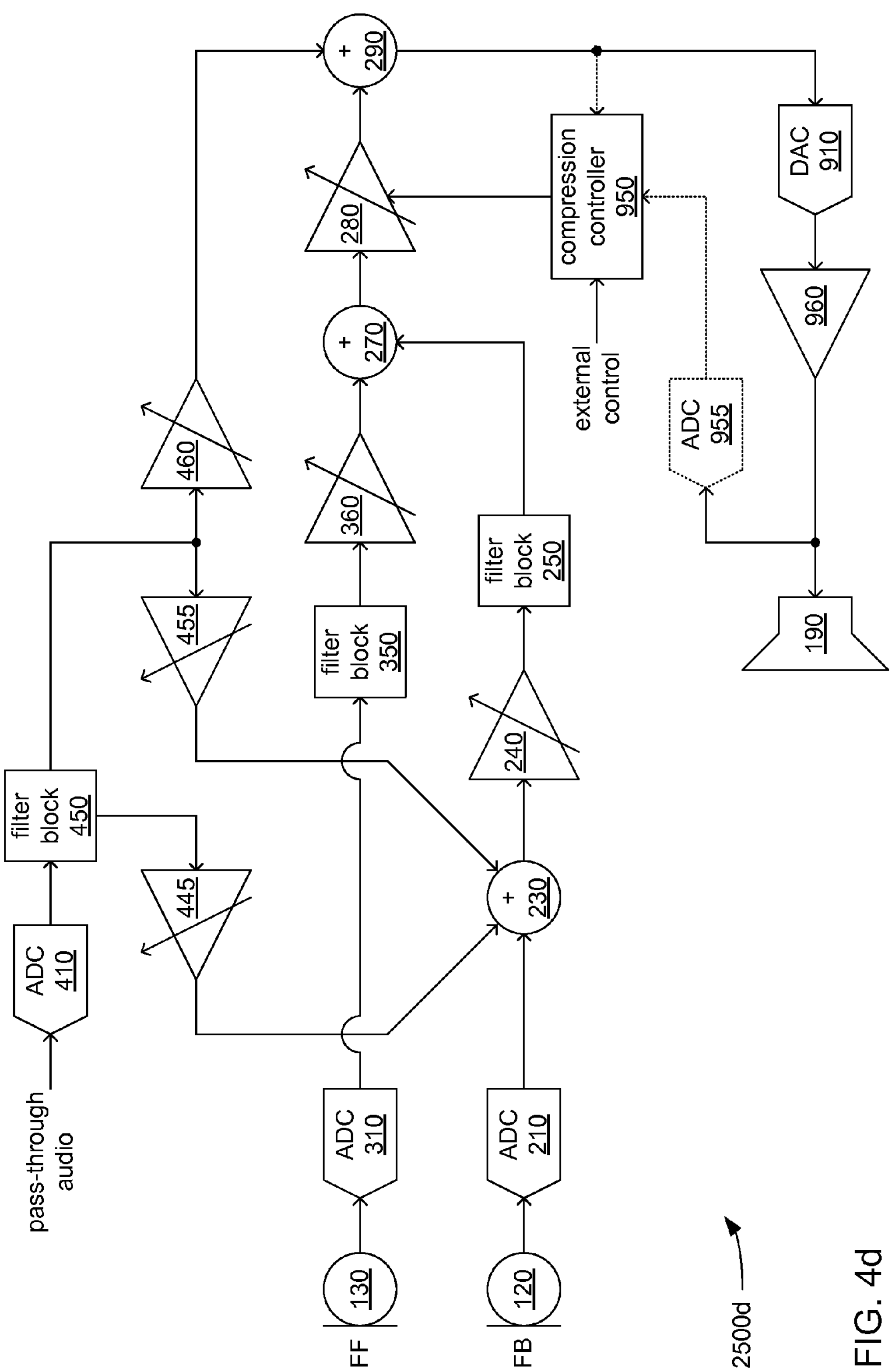

FIG. 4*d* depicts another possible signal processing topology 2500*d* for which the ANR circuit 2000 may be structured and/or programmed. Where the ANR circuit 2000 adopts the signal processing topology 2500*d*, the ANR circuit 2000 incorporates at least the DAC 910, the compression controller 950, the audio amplifier 960, the ADC 210, the summing nodes 230 and 290, the filter blocks 250 and 450, the VGA 280, and still other VGAs 445, 455 and 460. The ANR circuit 2000 may further incorporate one or more of the ADCs 310 and/or 410, the filter block 350, the summing node 270, the ADC 955, and still another VGA 360. The signal processing topologies 2500*c* and 2500*d* are similar in numerous ways. However, a substantial difference between the signal processing topologies 2500*c* and 2500*d* is the addition of the ability to direct the provision of the higher frequency sounds of the modified pass-through audio to be combined with other audio at either or both of two different locations within the signal processing topology 2500*d*.

One or more digital filters within the filter block 450 are employed to modify the digital data representing the pass-through audio to derive a modified variant of the pass-through audio data and to function as a crossover that divides the modified pass-through audio data into higher and lower frequency sounds. Data representing the lower frequency sounds are output to the summing node 230 through the VGA 445. Data representing the higher frequency sounds are output both to the summing node 230 through the VGA 455 and to the DAC 910 through the VGA 460. The VGAs 445, 455 and 460 are operable both to control the amplitudes of the lower frequency and higher frequency sounds represented by the data output by the filter block 450, and to selectively direct the flow of the data representing the higher frequency sounds. However, as has been previously discussed, the crossover functionality of the filter block 450 may be employed to selectively route the entirety of the modified pass-through audio to one or the other of the summing node 230 and the DAC 910.

Where the provision of feedforward-based ANR is also supported, the possible provision of higher frequency sounds (or perhaps the entirety of the modified pass-through audio) by the filter block 450 through the VGA 460 and to the DAC 910 may be through the summing node 290. The filter block 350 provides the feedforward anti-noise data to the summing node 270 through the VGA 360.

Figure 4E:
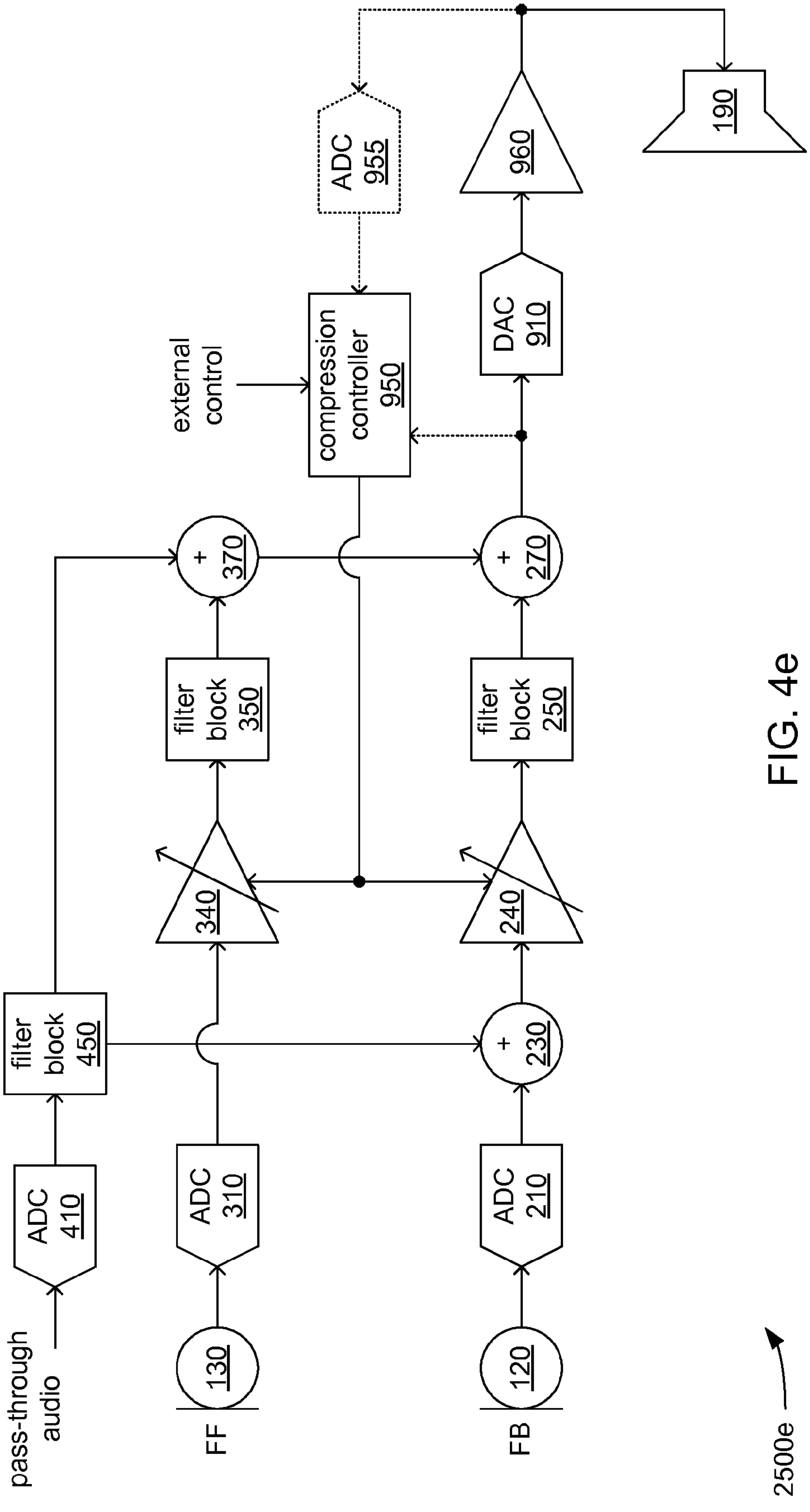

FIG. 4*e* depicts another possible signal processing topology 2500*e* for which the ANR circuit 2000 may be structured and/or programmed. Where the ANR circuit 2000 adopts the signal processing topology 2500*e*, the ANR circuit 2000 incorporates at least the DAC 910; the audio amplifier 960; the ADCs 210 and 310; the summing nodes 230, 270 and 370; the filter blocks 250, 350 and 450; the compressor 950; and a pair of VGAs 240 and 340. The ANR circuit 2000 may further incorporate one or both of the ADCs 410 and 955. The signal processing topologies 2500*b*, 2500*c* and 2500*e* are similar in numerous ways. The manner in which the data output by each of the filter blocks 250, 350 and 450 are combined in the signal processing topology 2500*e* is substantially similar to that of the signal processing topology 2500*b*. Also, like the signal processing topology 2500*c*, the signal processing topology 2500*e* incorporates the compression controller 950. However, a substantial difference between the signal processing topologies 2500*c* and 2500*e* is the replacement of the single VGA 280 in the signal processing topology 2500*c* for the separately controllable VGAs 240 and 340 in the signal processing topology 2500*e*.

The summing node 230 provides data representing feedback reference sounds possibly combined with data that may be output by the filter block 450 (perhaps the lower frequency sounds of the modified pass-through audio, or perhaps the entirety of the modified pass-through audio) to the filter block 250 through the VGA 240, and the ADC 310 provides data representing feedforward reference sounds to the filter block 350 through the VGA 340. The data output by the filter block 350 is combined with data that may be output by the filter block 450 (perhaps the higher frequency sounds of the modified pass-through audio, or perhaps the entirety of the modified pass-through audio) at the summing node 370. In turn, the summing node 370 provides its data to the summing node 270 to be combined with data output by the filter block 250. The summing node 270, in turn, provides its combined data to the DAC 910.

The compression controller 950 controls the gains of the VGAs 240 and 340, to enable the amplitude of the sounds represented by data output by the summing node 230 and the ADC 310, respectively, to be reduced in response to actual instances or indications of upcoming instances of clipping and/or other undesirable audio artifacts being detected by the compression controller 950. The gains of the VGAs 240 and 340 may be controlled in a coordinated manner, or may be controlled entirely independently of each other.

FIG. **4*f* depicts another possible signal processing topology 2500*f* for which the ANR circuit 2000 may be structured and/or programmed. Where the ANR circuit 2000 adopts the signal processing topology 2500*f*, the ANR circuit 2000 incorporates at least the DAC 910; the audio amplifier 960; the ADCs 210 and 310; the summing nodes 230, 270 and 370; the filter blocks 250, 350 and 450; the compressor 950; and the VGAs 125 and 135. The ANR circuit 2000 may further incorporate one or both of the ADCs 410 and 955. The signal processing topologies 2500*e* and 2500*f* are similar in numerous ways. However, a substantial difference between the signal processing topologies 2500*e* and 2500*f* is the replacement of the pair of VGAs 240 and 340 in the signal processing topology 2500*e* for the VGAs 125 and 135 in the signal processing topology 2500*f***.

The VGAs 125 and 135 positioned at the analog inputs to the ADCs 210 and 310, respectively, are analog VGAs, unlike the VGAs 240 and 340 of the signal processing topology **2500*e*. This enables the compression controller 950 to respond to actual occurrences and/or indications of soon-to-occur instances of clipping and/or other audio artifacts in driving the acoustic driver 190 by reducing the amplitude of one or both of the analog signals representing feedback and feedforward reference sounds. This may be deemed desirable where it is possible for the analog signals provided to the ADCs 210 and 310 to be at too great an amplitude such that clipping at the point of driving the acoustic driver 190 might be more readily caused to occur. The provision of the ability to reduce the amplitude of these analog signals (and perhaps also including the analog signal provided to the ADC 410 via the VGA 145 depicted elsewhere) may be deemed desirable to enable balancing of amplitudes between these analog signals, and/or to limit the numeric values of the digital data produced by one or more of the ADCs 210, 310 and 410** to lesser magnitudes to reduce storage and/or transmission bandwidth requirements.

FIG. **4*g* depicts another possible signal processing topology 2500*g* for which the ANR circuit 2000 may be programmed or otherwise structured. Where the ANR circuit 2000 adopts the signal processing topology 2500*g*, the ANR circuit 2000 incorporates at least the compression controller 950, the DAC 910, the audio amplifier 960, the ADCs 210 and 310, a pair of VGAs 220 and 320, the summing nodes 230 and 270, the filter blocks 250 and 350, another pair of VGAs 355 and 360, and the VGA 280. The ANR circuit 2000 may further incorporate one or more of the ADC 410, the filter block 450, still another VGA 460, the summing node 290, and the ADC 955**.

The ADC 210 receives an analog signal from the feedback microphone 120 and digitizes it, before providing corresponding feedback reference data to the VGA 220. The VGA 220 outputs the feedback reference data, possibly after modifying its amplitude, to the summing node 230. Similarly, the ADC 310 receives an analog signal from the feedforward microphone 130 and digitizes it, before providing corresponding feedforward reference data to the VGA 320. The VGA 320 outputs the feedforward reference data, possibly after modifying its amplitude, to the filter block 350. One or more digital filters within the filter block 350 are employed to modify the feedforward reference data to derive feedforward anti-noise data representing feedforward anti-noise sounds, and the filter block 350 provides the feedforward anti-noise data to both of the VGAs 355 and 360. In various implementations, the gains of the VGAs 355 and 360 are dynamically selectable and can be operated in a coordinated manner like a three-way switch to enable the feedforward anti-noise data to be selectively provided to either of the summing nodes 230 and 270. Thus, where the feedforward anti-noise data is combined with data related to feedback ANR within the signal processing topology **2500*g*** is made selectable.

Therefore, depending on the gains selected for the VGAs 355 and 360, the feedforward anti-noise data from the filter block 350 may be combined with the feedback reference data from the ADC 210 at the summing node 230, or may be combined with feedback anti-noise data derived by the filter block 250 from the feedback reference data at the summing node 270. If the feedforward anti-noise data is combined with the feedback reference data at the summing node 230, then the filter block 250 derives data representing a combination of feedback anti-noise sounds and further-modified feedforward anti-noise sounds, and this data is provided to the VGA 280 through the summing node 270 at which no combining of data occurs. Alternatively, if the feedforward anti-noise data is combined with the feedback anti-noise data at the summing node 270, then the feedback anti-noise data will have been derived by the filter block 250 from the feedback reference data received through the summing node 230 at which no combining of data occurs, and the data resulting from the combining at the summing node 270 is provided to the VGA 280. With or without an alteration in amplitude, the VGA 280 provides whichever form of combined data is received from the summing node 270 to the DAC 910 to create an analog signal. This provision of this combined data by the VGA 280 may be through the summing node 290 where the provision of pass-through audio is also supported.

Where the provision of pass-through audio is supported, the audio source 9400 may provide an analog signal representing pass-through audio to be acoustically output to a user, and the ADC 410 digitizes the analog signal and provides pass-through audio data corresponding to the analog signal to the filter block 450. Alternatively, where the audio source 9400 provides digital data representing pass-through audio, such digital data may be provided directly to the filter block 450. One or more digital filters within the filter block 450 may be employed to modify the digital data representing the pass-through audio to derive a modified variant of the pass-through audio data that may be re-equalized and/or enhanced in other ways. The filter block 450 provides the modified pass-through audio data to the VGA 460, and either with or without altering the amplitude of the pass-through audio sounds represented by the modified pass-through audio data, the VGA 460 provides the modified pass-through audio data to the DAC 910 through the summing node 290.

The compression controller 950 controls the gain of the VGA 280 to enable the amplitude of whatever combined form of feedback and feedforward anti-noise sounds are received by the VGA 280 to be reduced under the control of the compression controller 950 in response to actual occurrences and/or indications of impending instances of clipping and/or other audio artifacts.

FIGS. **5*a* through 5*e* depict some possible filter block topologies that may be employed in creating one or more blocks of filters (such as filter blocks 250, 350 and 450) within signal processing topologies adopted by the ANR circuit 2000 (such as the signal processing topologies 2500***a-g*). It should be noted that the designation of a multitude of digital filters as a "filter block" is an arbitrary construct meant to simplify the earlier presentation of signal processing topologies. In truth, the selection and positioning of one or more digital filters at any point along any of the pathways (such as the pathways 200, 300 and 400) of any signal processing topology may be accomplished in a manner identical to the selection and positioning of VGAs and summing nodes. Therefore, it is entirely possible for various digital filters to be positioned along a pathway for the movement of data in a manner in which those digital filters are interspersed among VGAs and/or summing nodes such that no distinguishable block of filters is created. Or, as will be illustrated, it is entirely possible for a filter block to incorporate a summing node or other component as part of the manner in which the filters of a filter block are coupled as part of the filter topology of a filter block.

However, as previously discussed, multiple lower-order digital filters may be combined in various ways to perform the equivalent function of one or more higher-order digital filters. Thus, although the creation of distinct filter blocks is not necessary in defining a pathway having multiple digital filters, it can be desirable in numerous situations. Further, the creation of a block of filters at a single point along a pathway can more easily enable alterations in the characteristics of filtering performed in that pathway. By way of example, multiple lower-order digital filters connected with no other components interposed between them can be dynamically configured to cooperate to perform any of a variety of higher-order filter functions by simply changing their coefficients and/or changing the manner in which they are interconnected. Also, in some implementations, such close interconnection of digital filters may ease the task of dynamically configuring a pathway to add or remove digital filters with a minimum of changes to the interconnections that define that pathway.

It should be noted that the selections of types of filters, quantities of filters, interconnections of filters and filter topologies depicted in each of FIGS. 5*a* through 5*e* are meant to serve as examples to facilitate understanding, and should not be taken as limiting the scope of what is described or the scope of what is claimed herein.

Figure 5A:
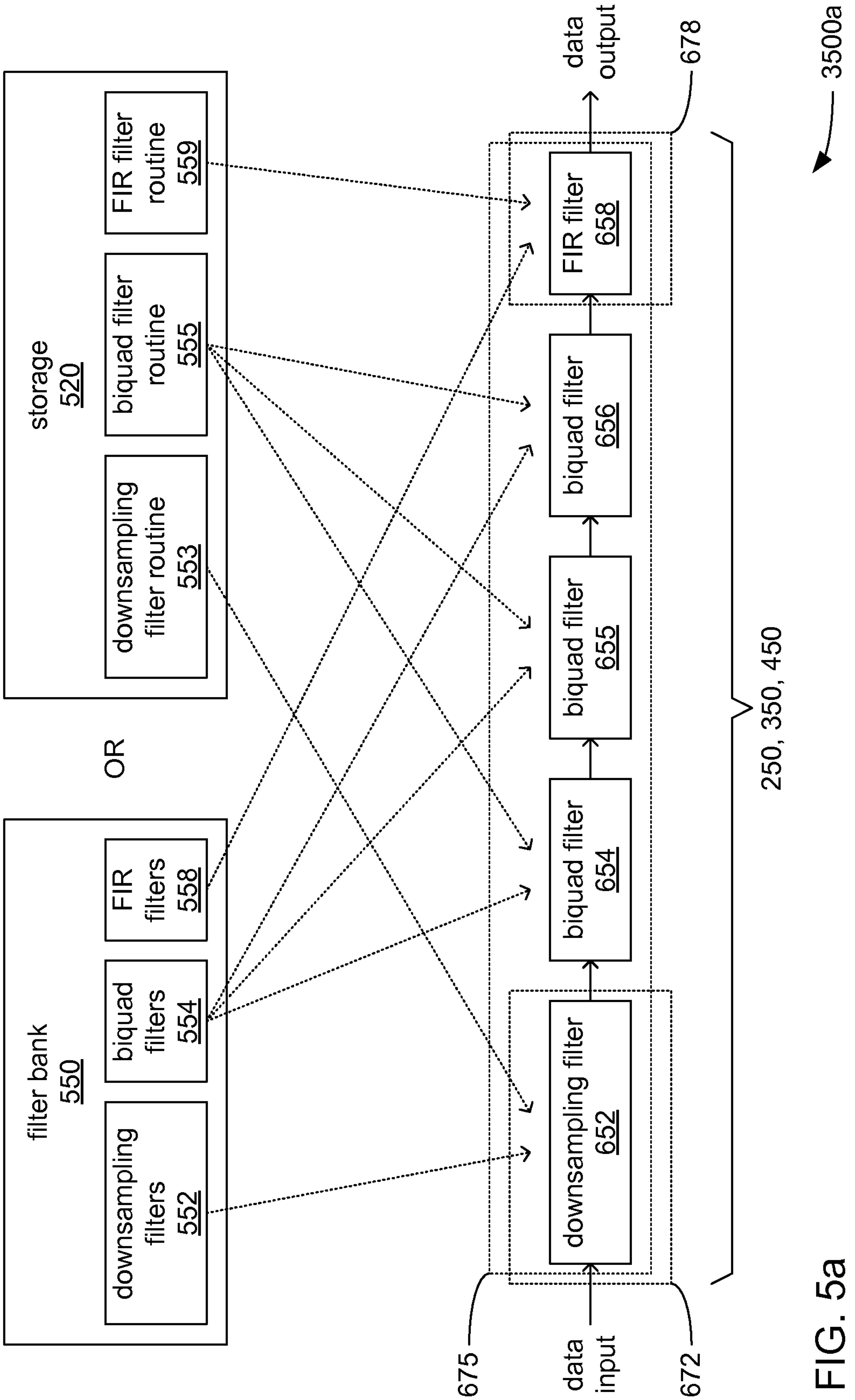
FIGS. 5*a* through 5*e* depict possible filter block topologies that may be adopted by the ANR circuit of the personal ANR device of FIG. 1.
Figure 6B:
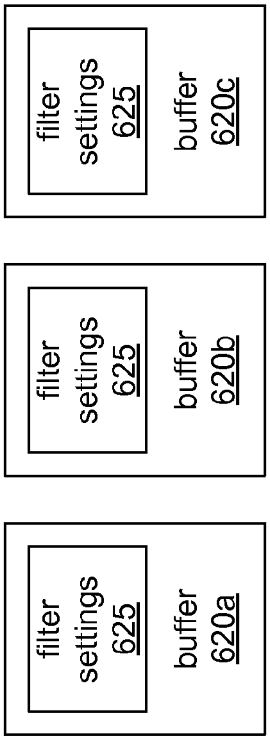
FIGS. 6*a* through 6*c* depict possible variants of triple-buffering that may be adopted by the ANR circuit of the personal ANR device of FIG. 1.
Figure 6A:
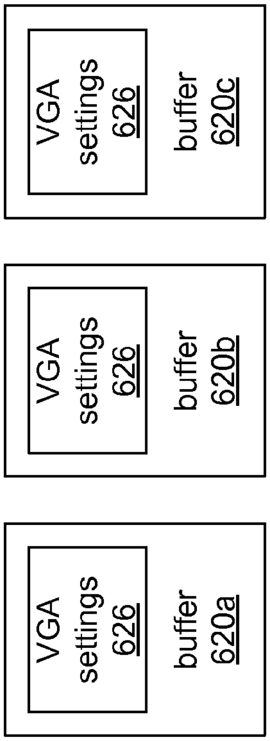
Figure 6C:
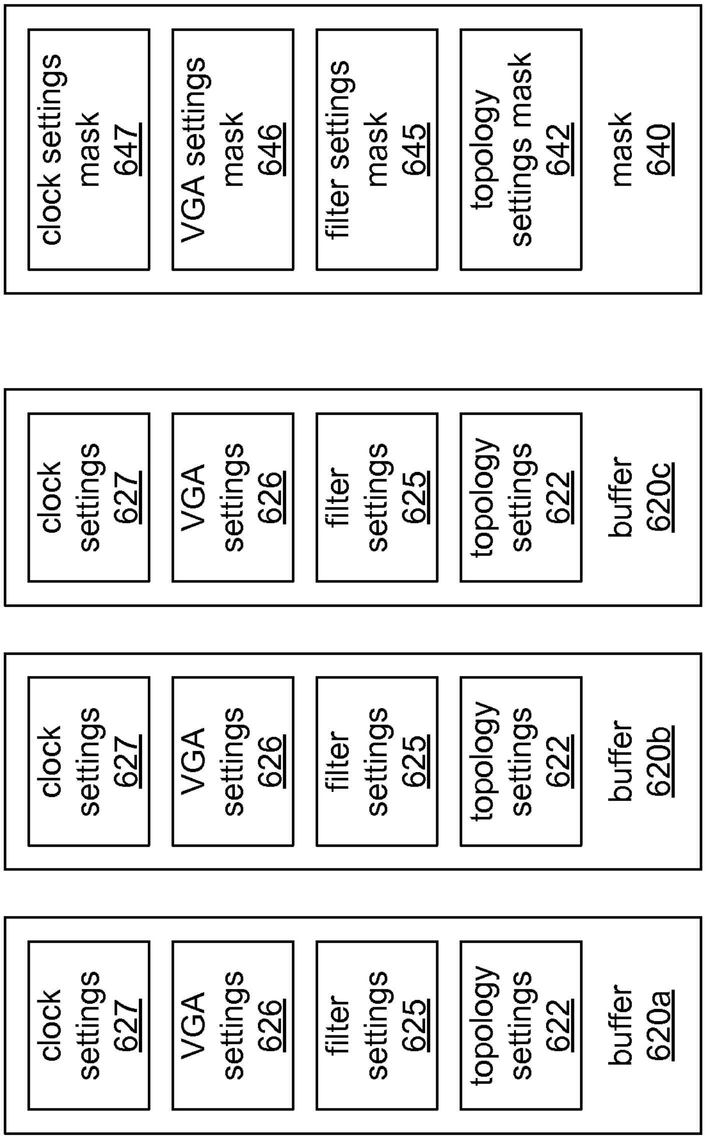

FIG. 5*a* depicts a possible filter block topology 3500*a* for which the ANR circuit 2000 may be structured and/or programmed to define a filter block, such as one of the filter blocks 250, 350 and 450. The filter block topology 3500*a* is made up of a serial chain of digital filters with a downsampling filter 652 at its input; biquad filters 654, 655 and 656; and a FIR filter 658 at its output.

As more explicitly depicted in FIG. 5*a*, in some implementations, the ANR circuit 2000 employs the internal architecture 2200*a* such that the ANR circuit 2000 incorporates the filter bank 550 incorporating multitudes of the downsampling filters 552, the biquad filters 554, and the FIR filters 558. One or more of each of the downsampling filters 552, biquad filters 554 and FIR filters 558 may be interconnected in any of a number of ways via the switch array 540, including in a way that defines the filter block topology 3500*a*. More specifically, the downsampling filter 652 is one of the downsampling filters 552; the biquad filters 654, 655 and 656 are each one of the biquad filters 554; and the FIR filter 658 is one of the FIR filters 558.

Alternatively, and as also more explicitly depicted in FIG. 5*a*, in other implementations, the ANR circuit 2000 employs the internal architecture 2200*b* such that the ANR circuit 2000 incorporates a storage 520 in which is stored the downsampling filter routine 553, the biquad filter routine 555 and the FIR filter routine 559. Varying quantities of downsampling, biquad and/or FIR filters may be instantiated within available storage locations of the storage 520 with any of a variety of interconnections defined between them, including quantities of filters and interconnections that define the filter block topology 3500*a*. More specifically, the downsampling filter 652 is an instance of the downsampling filter routine 553; the biquad filters 654, 655 and 656 are each instances of the biquad filter routine 555; and the FIR filter 658 is an instance of the FIR filter routine 559.

As previously discussed, power conservation and/or other benefits may be realized by employing different data transfer rates along different pathways of digital data representing sounds in a signal processing topology. In support of converting between different data transfer rates, including where one pathway operating at one data transfer rate is coupled to another pathway operating at another data transfer rate, different data transfer clocks may be provided to different ones of the digital filters within a filter block, and/or one or more digital filters within a filter block may be provided with multiple data transfer clocks.

By way of example, FIG. 5*a* depicts a possible combination of different data transfer rates that may be employed within the filter block topology 3500*a* to support digital data being received at one data transfer rate, digital data being transferred among these digital filters at another data transfer rate, and digital data being output at still another data transfer rate. More specifically, the downsampling filter 652 receives digital data representing a sound at a data transfer rate 672, and at least downsamples that digital data to a lower data transfer rate 675. The lower data transfer rate 675 is employed in transferring digital data among the downsampling filter 652, the biquad filters 654-656, and the FIR filter 658. The FIR filter 658 at least upsamples the digital data that it receives from the lower data transfer rate 675 to a higher data transfer rate 678 as that digital data is output by the filter block to which the digital filters in the filter block topology 3500*a* belong. Many other possible examples of the use of more than one data transfer rate within a filter block and the possible corresponding need to employ multiple data transfer clocks within a filter block will be clear to those skilled in the art.

Figure 5B:
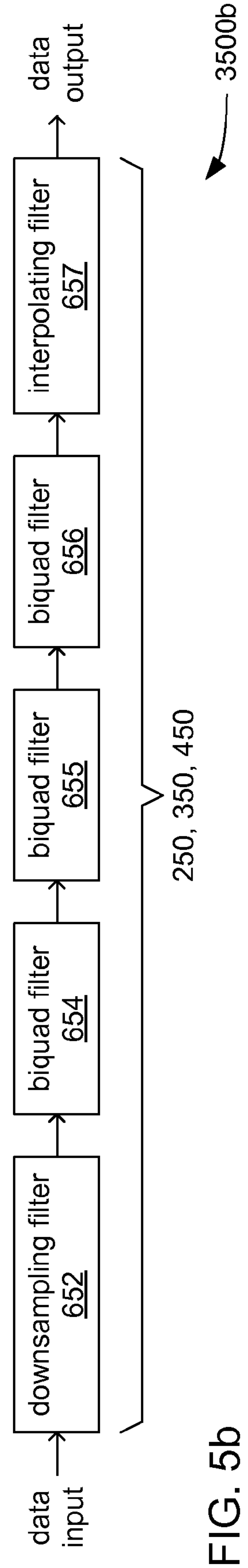

FIG. 5*b* depicts a possible filter block topology 3500*b* that is substantially similar to the filter block topology 3500*a*, but in which the FIR filter 658 of the filter block topology 3500*a* has been replaced with an interpolating filter 657. Where the internal architecture 2200*a* is employed, such a change from the filter block topology 3500*a* to the filter block topology 3500*b* entails at least altering the configuration of the switch array 540 to exchange one of the FIR filters 558 with one of the interpolating filters 556. Where the internal architecture 2200*b* is employed, such a change entails at least replacing the instantiation of the FIR filter routine 559 that provides the FIR filter 658 with an instantiation of the interpolating filter routine 557 to provide the interpolating filter 657

Figure 5C:
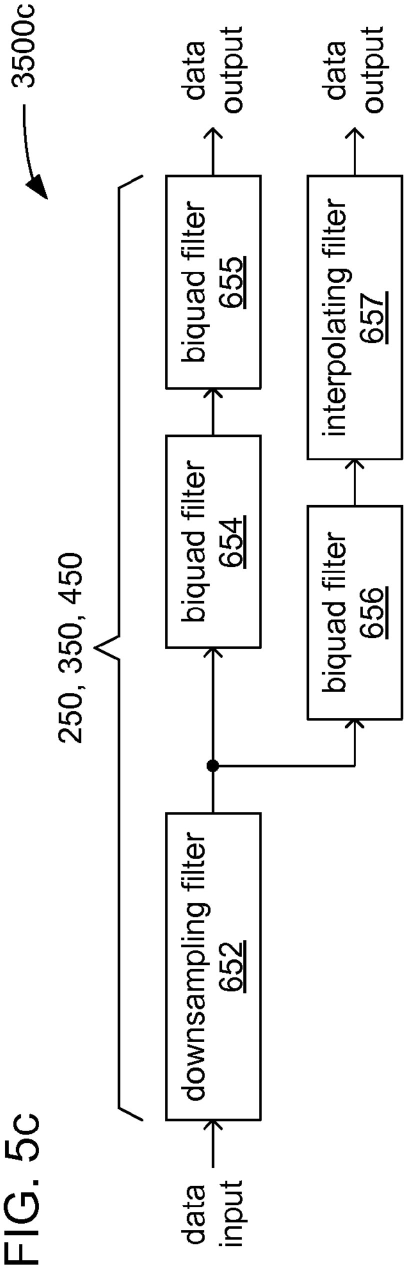

FIG. 5*c* depicts a possible filter block topology 3500*c* that is made up of the same digital filters as the filter block topology 3500*b*, but in which the interconnections between these digital filters have been reconfigured into a branching topology to provide two outputs, whereas the filter block topology 3500*b* had only one. Where the internal architecture 2200*a* is employed, such a change from the filter block topology 3500*b* to the filter block topology 3500*c* entails at least altering the configuration of the switch array 540 to disconnect the input to the biquad filter 656 from the output of the biquad filter 655, and to connect that input to the output of the downsampling filter 652, instead. Where the internal architecture 2200*b* is employed, such a change entails at least altering the instantiation of biquad filter routine 555 that provides the biquad filter 656 to receive its input from the instantiation of the downsampling filter routine 553 that provides the downsampling filter 652. The filter block topology 3500*c* may be employed where it is desired that a filter block be capable of providing two different outputs in which data representing audio provided at the input is altered in different ways to create two different modified versions of that data, such as in the case of the filter block 450 in each of the signal processing topologies 2500*b-f.*

Figure 5D:
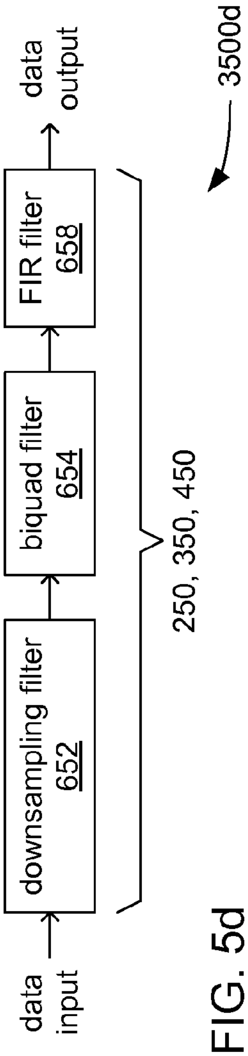

FIG. 5*d* depicts another possible filter block topology 3500*d* that is substantially similar to the filter block topology 3500*a*, but in which the biquad filters 655 and 656 have been removed to shorten the chain of digital filters from the quantity of five in the filter block topology 3500*a* to a quantity of three.

Figure 5E:
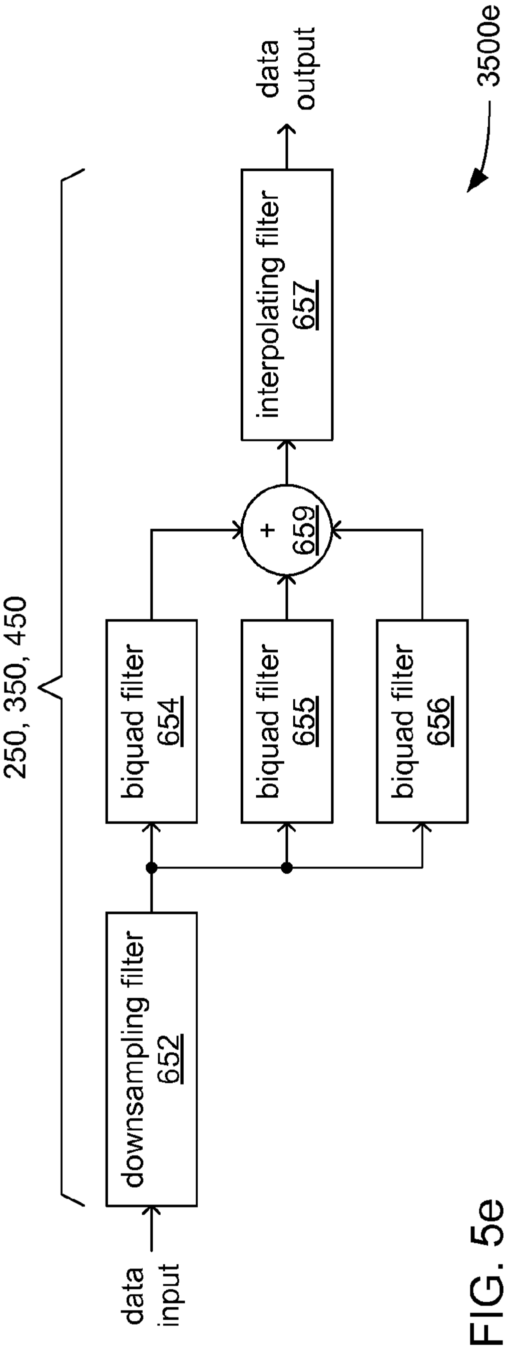

FIG. 5*e* depicts another possible filter block topology 3500*e* that is made up of the same digital filters as the filter block topology 3500*b*, but in which the interconnections between these digital filters have been reconfigured to put the biquad filters 654, 655 and 656 in a parallel configuration, whereas these same filters were in a serial chain configuration in the filter block topology 3500*b*. As depicted, the output of the downsampling filter 652 is coupled to the inputs of all three of the biquad filters 654, 655 and 656, and the outputs of all three of these biquad filters are coupled to the input of the interpolating filter 657 through an additionally incorporated summing node 659.

Taken together, the FIGS. 5*a* through 5*e* depict the manner in which a given filter block topology of a filter block is dynamically configurable to so as to allow the types of filters, quantities of filters and/or interconnections of digital filters to be altered during the operation of a filter block. However, as those skilled in the art will readily recognize, such changes in types, quantities and interconnections of digital filters are likely to require corresponding changes in filter coefficients and/or other settings to be made to achieve the higher-order filter function sought to be achieved with such changes. As will be discussed in greater detail, to avoid or at least mitigate the creation of audible distortions or other undesired audio artifacts arising from making such changes during the operation of the personal ANR device, such changes in interconnections, quantities of components (including digital filters), types of components, filter coefficients and/or VGA gain values are ideally buffered so as to enable their being made in a manner coordinated in time with one or more data transfer rates.

The dynamic configurability of both of the internal architectures 2200*a* and 2200*b*, as exemplified throughout the preceding discussion of dynamically configurable signal processing topologies and dynamically configurable filter block topologies, enables numerous approaches to conserving power and to reducing audible artifacts caused by the introduction of microphone self noise, quantization errors and other influences arising from components employed in the personal ANR device 1000. Indeed, there can be a synergy between achieving both goals, since at least some measures taken to reduce audible artifacts generated by the components of the personal ANR device 1000 can also result in reductions in power consumption. Reductions in power consumption can be of considerable importance given that the personal ANR device 1000 is preferably powered from a battery or other portable source of electric power that is likely to be somewhat limited in ability to provide electric power.

In either of the internal architectures 2200*a* and 2200*b*, the processing device 510 may be caused by execution of a sequence of instructions of the ANR routine 525 to monitor the availability of power from the power source 180. Alternatively and/or additionally, the processing device 510 may be caused to monitor characteristics of one or more sounds (e.g., feedback reference and/or anti-noise sounds, feedforward reference and/or anti-noise sounds, and/or pass-through audio sounds) and alter the degree of ANR provided in response to the characteristics observed. As those familiar with ANR will readily recognize, it is often the case that providing an increased degree of ANR often requires the implementation of a more complex transfer function, which often requires a greater number of filters and/or more complex types of filters to implement, and this in turn, often leads to greater power consumption. Analogously, a lesser degree of ANR often requires the implementation of a simpler transfer function, which often requires fewer and/or simpler filters, which in turn, often leads to less power consumption.

Further, there can arise situations, such as an environment with relatively low environmental noise levels or with environmental noise sounds occurring within a relatively narrow range of frequencies, where the provision of a greater degree of ANR can actually result in the components used in providing the ANR generating noise sounds greater than the attenuated environmental noise sounds. Still further, and as will be familiar to those skilled in the art of feedback-based ANR, under some circumstances, providing a considerable degree of feedback-based ANR can lead to instability as undesirable audible feedback noises are produced.

In response to either an indication of diminishing availability of electric power or an indication that a lesser degree of ANR is needed (or is possibly more desirable), the processing device 510 may disable one or more functions (including one or both of feedback-based and feedforward-based ANR), lower data transfer rates of one or more pathways, disable branches within pathways, lower data transfer rates between digital filters within a filter block, replace digital filters that consume more power with digital filters that consume less power, reduce the complexity of a transfer function employed in providing ANR, reduce the overall quantity of digital filters within a filter block, and/or reduce the gain to which one or more sounds are subjected by reducing VGA gain settings and/or altering filter coefficients. However, in taking one or more of these or other similar actions, the processing device 510 may be further caused by the ANR routine 525 to estimate a degree of reduction in the provision of ANR that balances one or both of the goals of reducing power consumption and avoiding the provision of too great a degree of ANR with one or both of the goals of maintaining a predetermined desired degree of quality of sound and quality of ANR provided to a user of the personal ANR device 1000. A minimum data transfer rate, a maximum signal-to-noise ratio or other measure may be used as the predetermined degree of quality or ANR and/or sound.

As an example, and referring back to the signal processing topology 2500*a* of FIG. 4*a* in which the pathways 200, 300 and 400 are explicitly depicted, a reduction in the degree of ANR provided and/or in the consumption of power may be realized through turning off one or more of the feedback-based ANR, feedforward-based ANR and pass-through audio functions. This would result in at least some of the components along one or more of the pathways 200, 300 and 400 either being operated to enter a low power state in which operations involving digital data would cease within those components, or being substantially disconnected from the power source 180. A reduction in power consumption and/or degree of ANR provided may also be realized through lowering the data transfer rate(s) of at least portions of one or more of the pathways 200, 300 and 400, as previously discussed in relation to FIG. 4*a*.

As another example, and referring back to the signal processing topology 2500*b* of FIG. 4*b* in which the pathways 200, 300 and 400 are also explicitly depicted, a reduction in power consumption and/or in the complexity of transfer functions employed may be realized through turning off the flow of data through one of the branches of the split in the pathway 400. More specifically, and as previously discussed in relation to FIG. 4*b*, the crossover frequency employed by the digital filters within the filter block 450 to separate the modified pass-through audio into higher frequency and lower frequency sounds may be selected to cause the entirety of the modified pass-through audio to be directed towards only one of the branches of the pathway 400. This would result in discontinuing of the transfer of modified pass-through audio data through one or the other of the summing nodes 230 and 370, thereby enabling a reduction in power consumption and/or in the introduction of noise sounds from components by allowing the combining function of one or the other of these summing nodes to be disabled or at least to not be utilized. Similarly, and referring back to the signal processing topology 2500*d* of FIG. 4*d* (despite the lack of explicit marking of its pathways), either the crossover frequency employed by the filter block 450 or the gain settings of the VGAs 445, 455 and 460 may be selected to direct the entirety of the modified pass-through audio data down a single one of the three possible pathway branches into which each of these VGAs lead. Thus, a reduction in power consumption and/or in the introduction of noise sounds would be enabled by allowing the combining function of one or the other of the summing nodes 230 and 290 to be disabled or at least not be utilized. Still further, one or more of the VGAs 445, 455 and 460 through which modified pass-through audio data is not being transferred may be disabled.

As still another example, and referring back to the filter block topology 3500*a* of FIG. 5*a* in which the allocation of three data transfer rates 672, 675 and 678 are explicitly depicted, a reduction in the degree of ANR provided and/or in power consumption may be realized through lowering one or more of these data transfer rates. More specifically, within a filter block adopting the filter block topology 3500*a*, the data transfer rate 675 at which digital data is transferred among the digital filters 652, 654-656 and 658 may be reduced. Such a change in a data transfer rate may also be accompanied by exchanging one or more of the digital filters for variations of the same type of digital filter that are better optimized for lower bandwidth calculations. As will be familiar to those skilled in the art of digital signal processing, the level of calculation precision required to maintain a desired predetermined degree of quality of sound and/or quality of ANR in digital processing changes as sampling rate changes. Therefore, as the data transfer rate 675 is reduced, one or more of the biquad filters 654-656 which may have been optimized to maintain a desired degree of quality of sound and/or desired degree of quality of ANR at the original data transfer rate may be replaced with other variants of biquad filter that are optimized to maintain substantially the same quality of sound and/or ANR at the new lower data transfer rate with a reduced level of calculation precision that also reduces power consumption. This may entail the provision of different variants of one or more of the different types of digital filter that employ coefficient values of differing bit widths and/or incorporate differing quantities of taps.

As still other examples, and referring back to the filter block topologies 3500*c* and 3500*d* of FIGS. 5*c* and 5*d*, respectively, as well as to the filter block topology 3500*a*, a reduction in the degree of ANR provided and/or in power consumption may be realized through reducing the overall quantity of digital filters employed in a filter block. More specifically, the overall quantity of five digital filters in the serial chain of the filter block topology 3500*a* may be reduced to the overall quantity of three digital filters in the shorter serial chain of the filter block topology 3500*d*. As those skilled in the art would readily recognize, such a change in the overall quantity of digital filters would likely need to be accompanied by a change in the coefficients provided to the one or more of the digital filters that remain, since it is likely that the transfer function(s) performed by the original five digital filters would have to be altered or replaced by transfer function(s) that are able to be performed with the three digital filters that remain. Also more specifically, the overall quantity of five digital filters in the branching topology of the filter block topology 3500*c* may be reduced to an overall quantity of three digital filters by removing or otherwise deactivating the filters of one of the branches (e.g., the biquad filter 656 and the interpolating filter 657 of one branch that provides one of the two outputs). This may be done in concert with selecting a crossover frequency for a filter block providing a crossover function to effectively direct all frequencies of a sound represented by digital data to only one of the two outputs, and/or in concert with operating one or more VGAs external to a filter block to remove or otherwise cease the transfer of digital data through a branch of a signal processing topology.

Reductions in data transfer rates may be carried out in various ways in either of the internal architectures 2200*a* and 2200*b*. By way of example in the internal architecture 2200*a*, various ones of the data transfer clocks provided by the clock bank 570 may be directed through the switch array 540 to differing ones of the digital filters, VGAs and summing nodes of a signal processing topology and/or filter block topology to enable the use of multiple data transfer rates and/or conversions between different data transfer rates by one or more of those components. By way of example in the internal architecture 2200*b*, the processing device 510 may be caused to execute the sequences of instructions of the various instantiations of digital filters, VGAs and summing nodes of a signal processing topology and/or filter block topology at intervals of differing lengths of time. Thus, the sequences of instructions for one instantiation of a given component are executed at more frequent intervals to support a higher data transfer rate than the sequences of instructions for another instantiation of the same component where a lower data transfer rate is supported.

As yet another example, and referring back to any of the earlier-depicted signal processing topologies and/or filter block topologies, a reduction in the degree of ANR provided and/or in power consumption may be realized through the reduction of the gain to which one or more sounds associated with the provision of ANR (e.g., feedback reference and/or anti-noise sounds, or feedforward reference and/or anti-noise sounds). Where a VGA is incorporated into at least one of a feedback-based ANR pathway and a feedforward-based ANR pathway, the gain setting of that VGA may be reduced. Alternatively and/or additionally, and depending on the transfer function implemented by a given digital filter, one or more coefficients of that digital filter may be altered to reduce the gain imparted to whatever sounds are represented by the digital data output by that digital filter. As will be familiar to those skilled in the art, reducing a gain in a pathway can reduce the perceptibility of noise sounds generated by components. In a situation where there is relatively little in the way of environmental noise sounds, noise sounds generated by components can become more prevalent, and thus, reducing the noise sounds generated by the components can become more important than generating anti-noise sounds to attenuate what little in the way of environmental noise sounds may be present. In some implementations, such reduction(s) in gain in response to relatively low environmental noise sound levels may enable the use of lower cost microphones.

In some implementations, performing such a reduction in gain at some point along a feedback-based ANR pathway may prove more useful than along a feedforward-based ANR pathway, since environmental noise sounds tend to be more attenuated by the PNR provided by the personal ANR device before ever reaching the feedback microphone 120. As a result of the feedback microphone 120 tending to be provided with weaker variants of environmental noise sounds than the feedforward microphone 130, the feedback-based ANR function may be more easily susceptible to a situation in which noise sounds introduced by components become more prevalent than environmental noise sounds at times when there is relatively little in the way of environmental noise sounds. A VGA may be incorporated into a feedback-based ANR pathway to perform this function by normally employing a gain value of 1 which would then be reduced to ½ or to some other preselected lower value in response to the processing device 510 and/or another processing device external to the ANR circuit 2000 and to which the ANR circuit 2000 is coupled determining that environmental noise levels are low enough that noise sounds generated by components in the feedback-based ANR pathway are likely to be significant enough that such a gain reduction is more advantageous than the production of feedback anti-noise sounds.

The monitoring of characteristics of environmental noise sounds as part of determining whether or not changes in ANR settings are to be made may entail any of a number of approaches to measuring the strength, frequencies and/or other characteristics of the environmental noise sounds. In some implementations, a simple sound pressure level (SPL) or other signal energy measurement without weighting may be taken of environmental noise sounds as detected by the feedback microphone 120 and/or the feedforward microphone 130 within a preselected range of frequencies. Alternatively, the frequencies within the preselected range of frequencies of a SPL or other signal energy measurement may subjected to the widely known and used "A-weighted" frequency weighting curve developed to reflect the relative sensitivities of the average human ear to different audible frequencies.

FIGS. 6*a* through 6*c* depict aspects and possible implementations of triple-buffering both to enable synchronized ANR setting changes and to enable a failsafe response to an occurrence and/or to indications of a likely upcoming occurrence of an out-of-bound condition, including and not limited to, clipping and/or excessive amplitude of acoustically output sounds, production of a sound within a specific range of frequencies that is associated with a malfunction, instability of at least feedback-based ANR, or other condition that may generate undesired or uncomfortable acoustic output. Each of these variations of triple-buffering incorporate at least a trio of buffers 620*a*, 620*b* and 620*c*. In each depicted variation of triple-buffering, two of the buffers 620*a* and 620*b* are alternately employed during normal operation of the ANR circuit 2000 to synchronously update desired ANR settings "on the fly," including and not limited to, topology interconnections, data clock settings, data width settings, VGA gain settings, and filter coefficient settings. Also, in each depicted variation of triple-buffering, the third buffer 620*c* maintains a set of ANR settings deemed to be "conservative" or "failsafe" settings that may be resorted to bring the ANR circuit 2000 back into stable operation and/or back to safe acoustic output levels in response to an out-of-bound condition being detected.

As will be familiar to those skilled in the art of controlling digital signal processing for audio signals, it is often necessary to coordinate the updating of various audio processing settings to occur during intervals between the processing of pieces of audio data, and it is often necessary to cause the updating of at least some of those settings to be made during the same interval. Failing to do so can result in the incomplete programming of filter coefficients, an incomplete or malformed definition of a transfer function, or other mismatched configuration issue that can result in undesirable sounds being created and ultimately acoustically output, including and not limited to, sudden popping or booming noises that can surprise or frighten a listener, sudden increases in volume that are unpleasant and can be harmful to a listener, or howling feedback sounds in the case of updating feedback-based ANR settings that can also be harmful.

In some implementations, the buffers 620*a-c* of any of FIGS. 6*a-c* are dedicated hardware-implemented registers, the contents of which are able to be clocked into registers within the VGAs, the digital filters, the summing nodes, the clocks of the clock bank 570 (if present), switch array 540 (if present), the DMA device 541 (if present) and/or other components. In other implementations, the buffers 620*a-c* of FIGS. 6*a-c* are assigned locations within the storage 520, the contents of which are able to be retrieved by the processing device 510 and written by the processing device 510 into other locations within the storage 520 associated with instantiations of the VGAs, digital filters, and summing nodes, and/or written by the processing device 510 into registers within the clocks of the clock bank 570 (if present), the switch array 540 (if present), the DMA device 541 (if present) and/or other components.

FIG. 6*a* depicts the triple-buffering of VGA settings, including gain values, employing variants of the buffers 620*a-c* that each store differing ones of VGA settings 626. An example of a use of such triple-buffering of VGA gain values may be the compression controller 950 operating one or more VGAs to reduce the amplitude of sounds represented by digital data in response to detecting occurrences and/or indications of impending occurrences of clipping and/or other audible artifacts in the acoustic output of the acoustic driver 190. In some implementations, the compression controller 950 stores new VGA settings into a selected one of the buffers 620*a* and 620*b*. At a subsequent time that is synchronized to the flow of pieces of digital data through one or more of the VGAs, the settings stored in the selected one of the buffers 620*a* and 620*b* are provided to those VGAs, thereby avoiding the generation of audible artifacts. As those skilled in the art will readily recognize, the compression controller 950 may repeatedly update the gain settings of VGAs over a period of time to "ramp down" the amplitude of one or more sounds to a desired level of amplitude, rather than to immediately reduce the amplitude to that desired level. In such a situation, the compression controller 950 would alternate between storing updated gain settings to the buffer 620*a* and storing updated gain settings to the buffer 620*b*, thereby enabling the decoupling of the times at which each of the buffers 620*a* and 620*b* are each written to by the compression controller 950 and the times at which each of the buffers provide their stored VGA settings to the VGAs. However, a set of more conservatively selected VGA settings is stored in the buffer 620*c*, and these failsafe settings may be provided to the VGAs in response to an out-of-bound condition being detected. Such provision of the VGA settings stored in the buffer 620*c* overrides the provision of any VGA settings stored in either of the buffers 620*a* and 620*b*.

FIG. 6*b* depicts the triple-buffering of filter settings, including filter coefficients, employing variants of the buffers 620*a-c* that each store differing ones of filter settings 625. An example of a use of such triple-buffering of filter coefficients may be adjusting the range of frequencies and/or the degree of attenuation of noise sounds that are reduced in the feedback-based ANR provided by the personal ANR device 1000. In some implementations, processing device 510 is caused by the ANR routine 525 to store new filter coefficients into a selected one of the buffers 620*a* and 620*b*. At a subsequent time that is synchronized to the flow of pieces of digital data through one or more of the digital filters, the settings stored in the selected one of the buffers 620*a* and 620*b* are provided to those digital filters, thereby avoiding the generation of audible artifacts. Another example of a use of such triple-buffering of filter coefficients may be adjusting the crossover frequency employed by the digital filters within the filter block 450 in some of the above signal processing topologies to divide the sounds of the modified pass-through audio into lower and higher frequency sounds. At a time synchronized to at least the flow of pieces of digital data associated with pass-through audio through the digital filters of the filter block 450, filter settings stored in one or the other of the buffers 620*a* and 620*b* are provided to at least some of the digital filters.

FIG. 6*c* depicts the triple-buffering of either all or a selectable subset of clock, VGA, filter and topology settings, employing variants of the buffers 620*a-c* that each store differing ones of topology settings 622, filter settings 625, VGA settings 626 and clock settings 627. An example of a use of triple-buffering of all of these settings may be changing from one signal processing topology to another in response to a user of the personal ANR device 1000 operating a control to activate a "talk-through" feature in which the ANR provided by the personal ANR device 1000 is altered to enable the user to more easily hear the voice of another person without having to remove the personal ANR device 1000 or completely turn off the ANR function. The processing device 510 may be caused to store the settings required to specify a new signal processing topology in which voice sounds are more readily able to pass to the acoustic driver 190 from the feedforward microphone 130, and the various settings of the VGAs, digital filters, data clocks and/or other components of the new signal processing topology within one or the other of the buffers 620*a* and 620*b*. Then, at a time synchronized to the flow of at least some pieces of digital data representing sounds through at least one component (e.g., an ADC, a VGA, a digital filter, a summing node, or a DAC), the settings are used to create the interconnections for the new signal processing topology (by being provided to the switch array 540, if present) and are provided to the components that are to be used in the new signal processing topology.

However, some variants of the triple-buffering depicted in FIG. 6*c* may further incorporate a mask 640 providing the ability to determine which settings are actually updated as either of the buffers 620*a* and 620*b* provide their stored contents to one or more components. In some embodiments, bit locations within the mask are selectively set to either 1 or 0 to selectively enable the contents of different ones of the settings corresponding to each of the bit locations to be provided to one or more components when the contents of one or the other of the buffers 620*a* and 620*b* are to provide updated settings to the components. The granularity of the mask 640 may be such that each individual setting may be selectively enabled for updating, or may be such that the entirety of each of the topology settings 622, the filter settings 625, the VGA setting 626 and the clock setting 627 are able to be selected for updating through the topology settings mask 642, the filter settings mask 645, the VGA settings mask 646 and the clock settings mask 647, respectively.

Figure 7A:
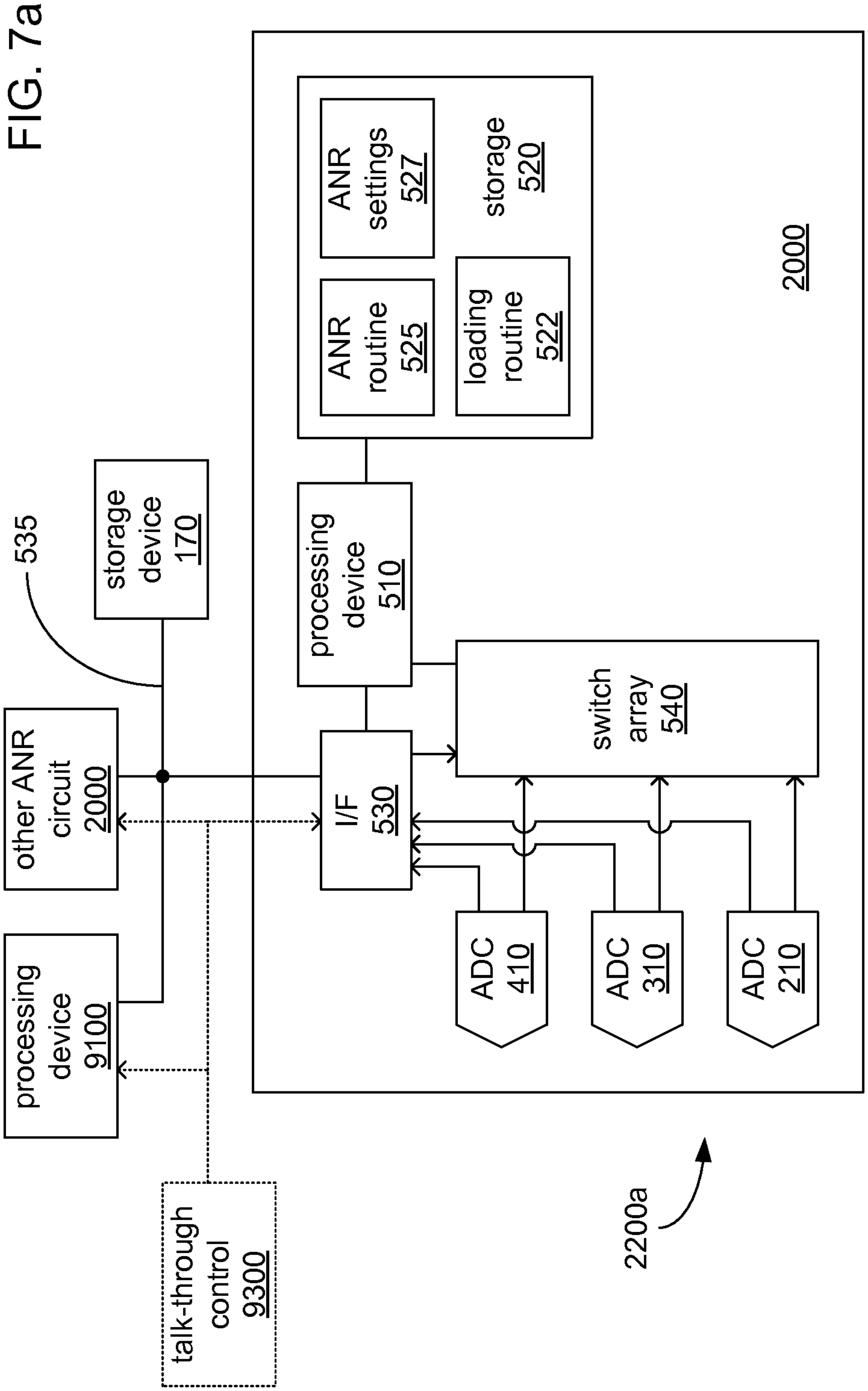
FIG. 7*a* depicts a possible additional portion of the internal architecture of FIG. 3*a*.
Figure 7B:
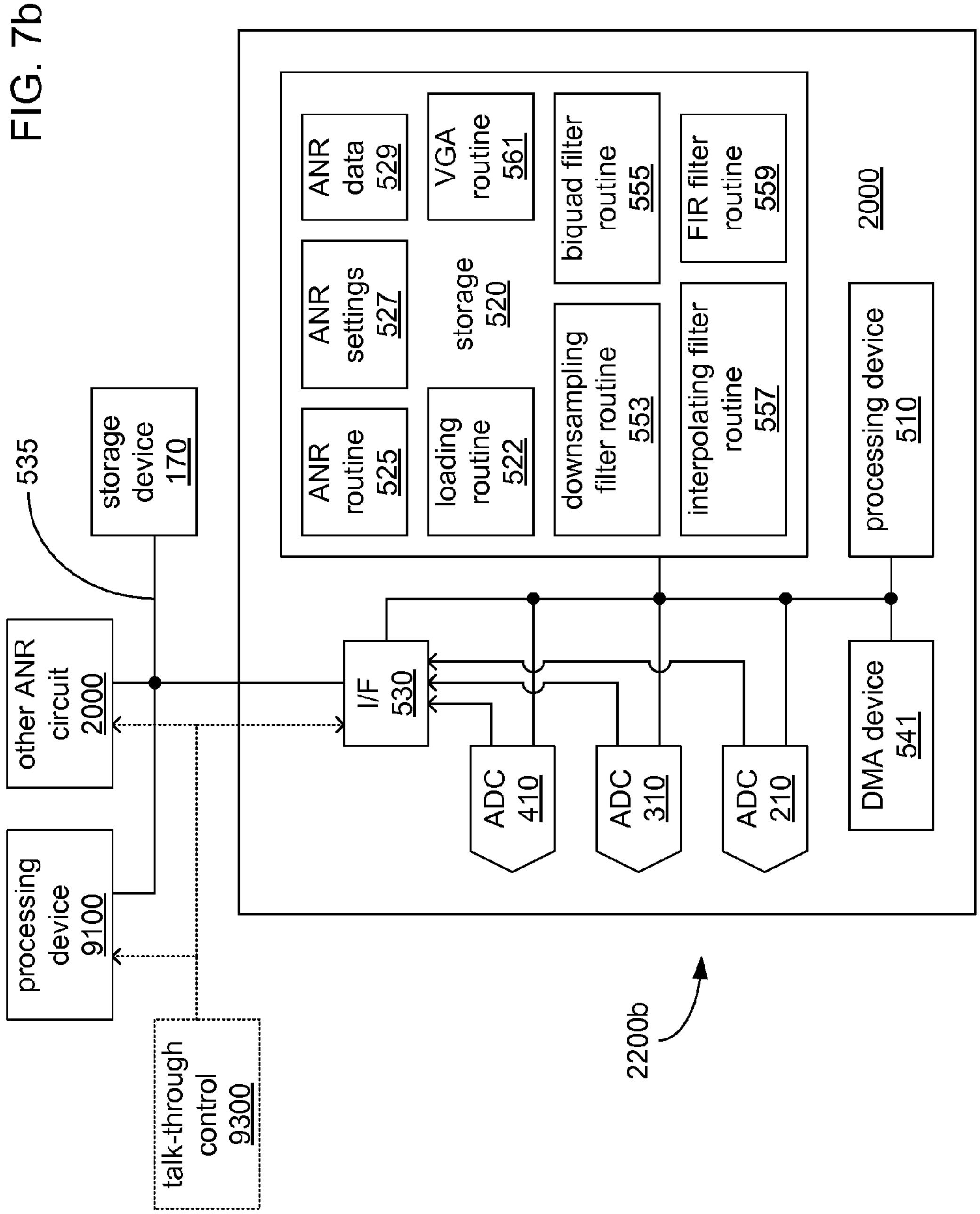
FIG. 7*b* depicts a possible additional portion of the internal architecture of FIG. 3*b*.

FIGS. 7*a* and 7*b* each depict variations of a number of possible additions to the internal architectures 2200*a* and 2200*b*, respectively, of the ANR circuit 2000. Therefore, it should be noted that for sake of simplicity of discussion, only portions of the internal architectures 2200*a* and 2200*b* associated with these possible additions are depicted. Some of these possible additions rely on the use of the interface 530 coupling the ANR circuit 2000 to other devices via at least one bus 535. Others of these possible additions rely on the use of the interface 530 to receive a signal from at least one manually-operable control.

More particularly, in executing a sequence of instructions of the loading routine 522 to possibly retrieve at least some of the contents of the ANR settings 527 from an external storage device (e.g., the storage device 170), the processing device 510 may be caused to configure the ANR circuit 2000 to accept those contents from an external processing device 9100, instead. Also, to better enable the use of adaptive algorithms in providing feedback-based and/or feedforward-based ANR functions, the external processing device 9100 may be coupled to the ANR circuit 2000 to augment the functionality of the ANR circuit 2000 with analysis of statistical information concerning feedback reference sounds, feedforward reference sounds and/or pass-through audio, where side-chain information is provided from downsampling and/or other filters either built into or otherwise connected to one or more of the ADCs 210, 310 and 410. Further, to enable cooperation between two of the ANR circuits 2000 to achieve a form of binaural feedforward-based ANR, each one of the ANR circuits 2000 may transmit copies of feedforward reference data to the other. Still further, one or more of the ANR circuit 2000 and/or the external processing device 9100 may monitor a manually-operable talk-through control 9300 for instances of being manually operated by a user to make use of a talk-through function.

The ANR circuit 2000 may accept an input from the talk-through control 9300 coupled to the ANR circuit 2000 directly, through another ANR circuit 2000 (if present), or through the external processing device 9100 (if present). Where the personal ANR device 1000 incorporates two of the ANR circuit 2000, the talk-through control 9300 may be directly coupled to the interface 530 of each one of the ANR circuit 2000, or may be coupled to a single one of the external processing device 9100 (if present) that is coupled to both of the ANR circuits 2000, or may be coupled to a pair of the external processing devices 9100 (if present) where each one of the processing devices 9100 is separately coupled to a separate one of each of the ANR circuits 2000.

Regardless of the exact manner in which the talk-through control 9300 is coupled to other component(s), upon the talk-through control 9300 being detected as having been manually operated, the provision of at least feedforward-based ANR is altered such that attenuation of sounds in the human speech band detected by the feedforward microphone 130 is reduced. In this way, sounds in the human speech band detected by the feedforward microphone 130 are actually conveyed through at least a pathway for digital data associated with feedforward-based ANR to be acoustically output by the acoustic driver 190, while other sounds detected by the feedforward microphone 130 continue to be attenuated through feedforward-based ANR. In this way, a user of the personal ANR device 1000 is still able to have the benefits of at least some degree of feedforward-based ANR to counter environmental noise sounds, while also being able to hear the voice of someone talking nearby.

As will be familiar to those skilled in the art, there is some variation in what range of frequencies is generally accepted as defining the human speech band from ranges as wide as 300 Hz to 4 KHz to ranges as narrow as 1 KHz to 3 KHz. In some implementations, the processing device 510 and/or the external processing device 9100 (if present) is caused to respond to the user operating the talk-through control 9300 by altering ANR settings for at least the filters in the pathway for feedforward-based ANR to reduce the range of frequencies of environmental noise sounds attenuated through feedforward-based ANR such that the feedforward-based ANR function is substantially restricted to attenuating frequencies below whatever range of frequencies is selected to define the human speech band for the personal ANR device 1000. Alternatively, the ANR settings for at least those filters are altered to create a "notch" for a form of the human speech band amidst the range of frequencies of environmental noise sounds attenuated by feedforward-based ANR, such that feedforward-based ANR attenuates environmental noise sounds occurring in frequencies below that human speech band and above that human speech band to a considerably greater degree than sounds detected by the feedforward microphone 130 that are within that human speech band. Either way, at least one or more filter coefficients are altered to reduce attenuation of sounds in the human speech band. Further, the quantity and/or types of filters employed in the pathway for feedforward-based ANR may be altered, and/or the pathway for feedforward-based ANR itself may be altered.

Although not specifically depicted, an alternative approach to providing a form of talk-through function that is more amenable to the use of analog filters would be to implement a pair of parallel sets of analog filters that are each able to support the provision of feedforward-based ANR functionality, and to provide a form of manually-operable talk-through control that causes one or more analog signals representing feedforward-based ANR to be routed to and/or from one or the other of the parallel sets of analog filters. One of the parallel sets of analog filters is configured to provide feedforward-based ANR without accommodating talk-through functionality, while the other of the parallel sets of filters is configured to provide feedforward-based ANR in which sounds within a form of the human speech band are attenuated to a lesser degree. Something of a similar approach could be implemented within the internal architecture 2200*a* as yet another alternative, in which a form of manually-operable talk-through control directly operates at least some of the switching devices within the switch array 540 to switch the flow of digital data between two parallel sets of digital filters.

Figure 8:
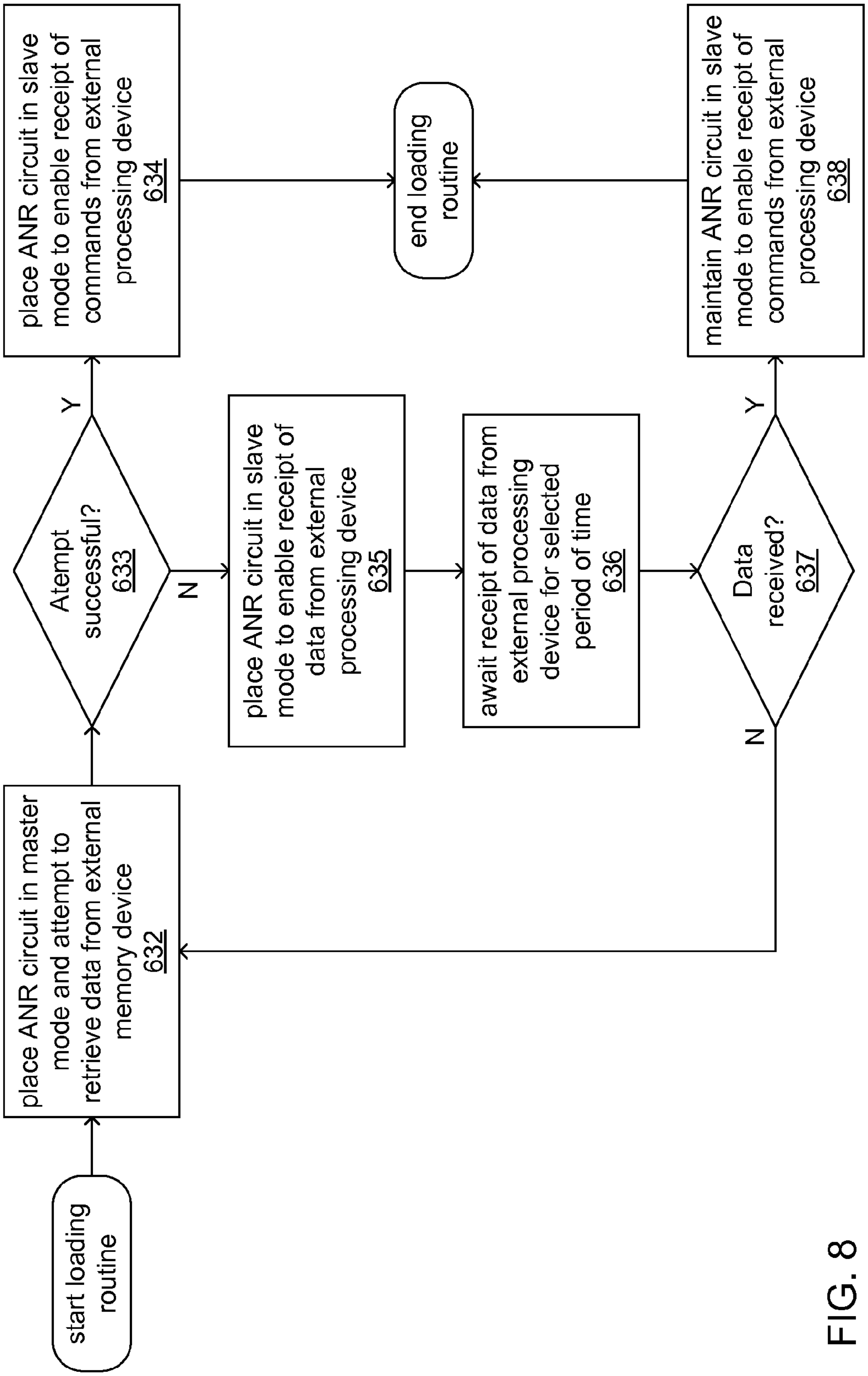
FIG. 8 is a flowchart of a possible boot loading sequence that may be adopted by the ANR circuit of the personal ANR device of FIG. 1.

FIG. 8 is a flowchart of an implementation of a possible loading sequence by which at least some of the contents of the ANR settings 527 to be stored in the storage 520 may be provided across the bus 535 from either the external storage device 170 or the processing device 9100. This loading sequence is intended to allow the ANR circuit 2000 to be flexible enough to accommodate any of a variety of scenarios without alteration, including and not limited to, only one of the storage device 170 and the processing device 9100 being present on the bus 535, and one or the other of the storage device 170 and the processing device 9100 not providing such contents despite both of them being present on the bus. The bus 535 may be either a serial or parallel digital electronic bus, and different devices coupled to the bus 535 may serve as a bus master at least coordinating data transfers.

Upon being powered up and/or reset, the processing device 510 accesses the storage 520 to retrieve and execute a sequence of instructions of the loading routine 522. Upon executing the sequence of instructions, at 632, the processing device 510 is caused to operate the interface 530 to cause the ANR circuit 2000 to enter master mode in which the ANR circuit 2000 becomes a bus master on the bus 535, and then the processing device 510 further operates the interface 530 to attempt to retrieve data (such as part of the contents of the ANR settings 527) from a storage device also coupled to the bus 535, such as the storage device 170. If, at 633, the attempt to retrieve data from a storage device succeeds, then the processing device 510 is caused to operate the interface 530 to cause the ANR circuit 2000 to enter a slave mode on the bus 535 to enable another processing device on the bus 535 (such as the processing device 9100) to transmit data to the ANR circuit 2000 (including at least part of the contents of the ANR settings 527) at 634.

However, if at 633, the attempt to retrieve data from a storage device fails, then the processing device 510 is caused to operate the interface 530 to cause the ANR circuit 2000 to enter a slave mode on the bus 535 to enable receipt of data from an external processing device (such as the external processing device 9100) at 635. At 636, the processing device 510 is further caused to await the receipt of such data from another processing device for a selected period of time. If, at 637, such data is received from another processing device, then the processing device 510 is caused to operate the interface 530 to cause the ANR circuit 2000 to remain in a slave mode on the bus 535 to enable the other processing device on the bus 535 to transmit further data to the ANR circuit 2000 at 638. However, if at 637, no such data is received from another processing device, then the processing device 510 is caused to operate the interface 530 to cause the ANR circuit 2000 to return to being a bus master on the bus 535 and to again attempt to retrieve such data from a storage device at 632.

Figure 9A:
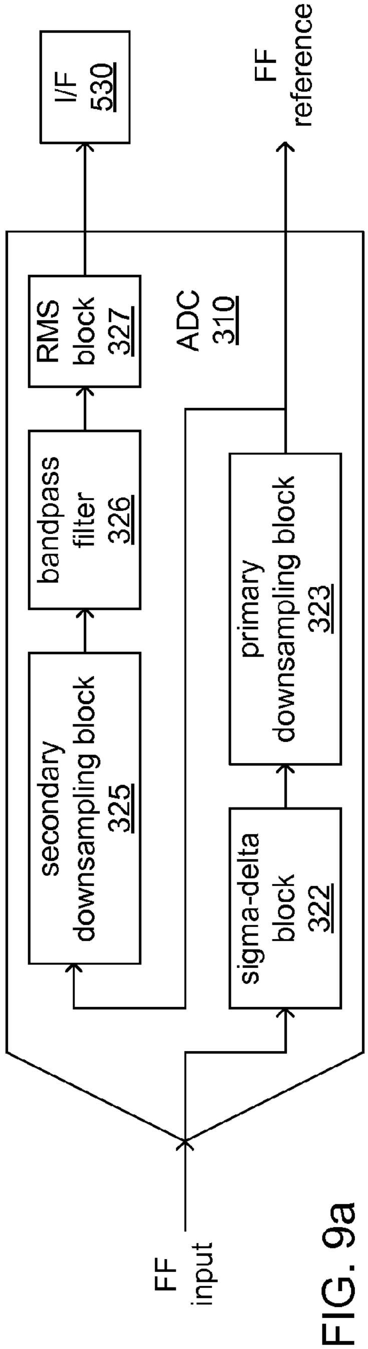
FIG. 9*a* depicts a possible internal architecture of an ADC of the ANR circuit of the personal ANR device of FIG. 1.
Figure 9B:
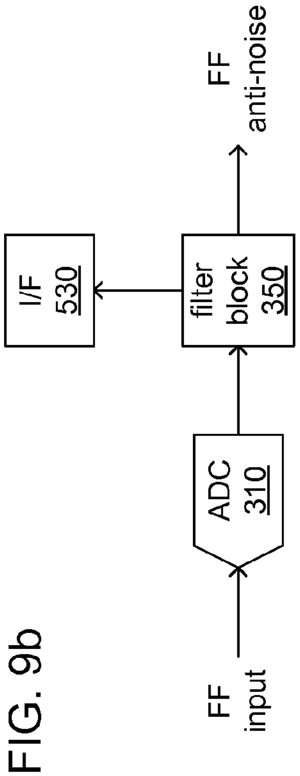
FIG. 9*b* depicts a possible additional portion of any of the signal processing topologies of FIGS. 4*a* through 4*g*.

FIGS. 9*a* and 9*b* each depict a manner in which either of the internal architectures 2200*a* and 2200*b* may support the provision of side-chain data to the external processing device 9100, possibly to enable the processing device 9100 to add adaptive features to feedback-based and/or feedforward-based ANR functions performed by the ANR circuit 2000. In essence, while the ANR circuit 2000 performs the filtering and other aspects of deriving feedback and feedforward anti-noise sounds, as well as combining those anti-noise sounds with pass-through audio, the processing device 9100 performs analyses of various characteristics of feedback and/or feedforward reference sounds detected by the microphones 120 and/or 130. Where the processing device 9100 determines that there is a need to alter the signal processing topology of the ANR circuit 2000 (including altering a filter block topology of one of the filter blocks 250, 350 and 450), alter VGA gain values, alter filter coefficients, alter clock timings by which data is transferred, etc., the processing device 9100 provides new ANR settings to the ANR circuit 2000 via the bus 535. As previously discussed, those new ANR settings may be stored in one or the other of the buffers 620*a* and 620*b* in preparation for those new ANR settings to be provided to components within the ANR circuit 2000 with a timing synchronized to one or more data transfer rates at which pieces of digital data representing sounds are conveyed between components within the ANR circuit 2000. Indeed, in this way, the provision of ANR by the ANR circuit 2000 can also be made adaptive.

In supporting such cooperation between the ANR circuit 2000 and the external processing device 9100, it may be deemed desirable to provide copies of the feedback reference data, the feedforward reference data and/or the pass-through audio data to the processing device 9100 without modification. However, it is contemplated that such data may be sampled at high clock frequencies, possibly on the order of 1 MHz for each of the feedback reference data, the feedforward reference data and the pass-through audio data. Thus, providing copies of all of such data at such high sampling rates through the bus 535 to the processing device 9100 may place undesirably high burdens on the ANR circuit 2000, as well as undesirably increase the power consumption requirements of the ANR circuit 2000. Further, at least some of the processing that may be performed by the processing device 9100 as part of such cooperation with the ANR circuit 2000 may not require access to such complete copies of such data. Therefore, implementations of the ANR circuit 2000 employing either of the internal architectures 2200*a* and 2200*b* may support the provision of lower speed side-chain data made up of such data at lower sampling rates and/or various metrics concerning such data to the processing device 9100.

FIG. 9*a* depicts an example variant of the ADC 310 having the ability to output both feedforward reference data representative of the feedforward reference analog signal received by the ADC 310 from the feedforward microphone 130 and corresponding side-chain data. This variant of the ADC 310 incorporates a sigma-delta block 322, a primary downsampling block 323, a secondary downsampling block 325, a bandpass filter 326 and a RMS block 327. The sigma-delta block 322 performs at least a portion of a typical sigma-delta analog-to-digital conversion of the analog signal received by the ADC 310, and provides the feedforward reference data at a relatively high sampling rate to the primary downsampling block 323. The primary downsampling block 323 employs any of a variety of possible downsampling (and/or decimation) algorithms to derive a variant of the feedforward reference data at a more desirable sampling rate to whatever combination of VGAs, digital filters and/or summing nodes is employed in deriving feedforward anti-noise data representing anti-noise sounds to be acoustically output by the acoustic driver 190. However, the primary downsampling block 323 also provides a copy of the feedforward reference data to the secondary downsampling block 325 to derive a further downsampled (and/or decimated) variant of the feedforward reference data. The secondary downsampling block 325 then provides the further downsampled variant of the feedforward reference data to the bandpass filter 326 where a subset of the sounds represented by the further downsampled feedforward reference data that are within a selected range of frequencies are allowed to be passed on to the RMS block 327. The RMS block 327 calculates RMS values of the further downsampled feedforward reference data within the selected range of frequencies of the bandpass filter 326, and then provides those RMS values to the interface 530 for transmission via the bus 535 to the processing device 9100.

It should be noted that although the above example involved the ADC 310 and digital data associated with the provision of feedforward-based ANR, similar variations of either of the ADCs 210 and 410 involving either of the feedback-based ANR and pass-through audio, respectively, are possible. Also possible are alternate variations of the ADC 310 (or of either of the ADCs 210 and 410) that do not incorporate the secondary downsampling block 325 such that further downsampling (and/or decimating) is not performed before data is provided to the bandpass filter 326, alternate variations that employ an A-weighted or B-weighted filter in place of or in addition to the bandpass filter 326, alternate variations that replace the RMS block 327 with another block performing a different form of signal strength calculation (e.g., an absolute value calculation), and alternate variations not incorporating the bandpass filter 326 and/or the RMS block 327 such that the downsampled (and/or decimated) output of the secondary downsampling block 325 is more conveyed to the interface with less or substantially no modification.

FIG. 9*b* depicts an example variant of the filter block 350 having the ability to output both feedforward anti-noise data and side-chain data corresponding to the feedforward reference data received by the filter block 350. As has been previously discussed at length, the quantity, type and interconnections of filters within the filter blocks 250, 350 and 450 (i.e., their filter block topologies) are each able to be dynamically selected as part of the dynamic configuration capabilities of either of the internal architectures 2200*a* and 2200*b*. Therefore, this variant of the filter block 350 may be configured with any of a variety of possible filter block topologies in which both of the functions of deriving feedforward anti-noise data and side-chain data are performed.

Figure 10A:
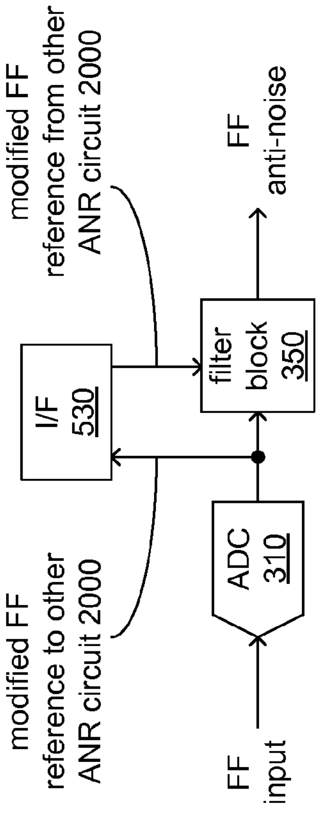
FIGS. 10*a* and 10*b* depict possible additional portions of any of the signal processing topologies of FIGS. 4*a* through 4*g*.
Figure 10B:
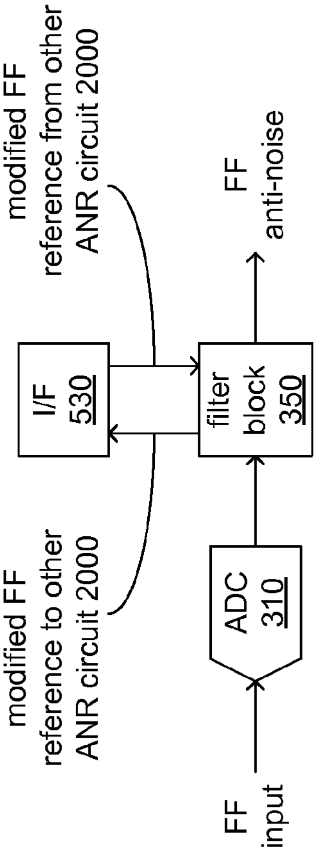

FIGS. 10*a* and 10*b* each depict a manner in which either of the internal architectures 2200*a* and 2200*b* may support binaural feedforward-based ANR in which feedforward reference data is shared between a pair of the ANR circuits 2000 (with each incarnation of the ANR circuit 2000 providing feedforward-based ANR to a separate one of a pair of the earpieces 100). In some implementations of the personal ANR device 1000 having a pair of the earpieces 100, feedforward reference data representing sounds detected by separate feedforward microphones 130 associated with each of the earpieces 100 is provided to both of the separate ANR circuits 2000 associated with each of the earpieces. This is accomplished through an exchange of feedforward reference data across a bus connecting the pair of ANR circuits 2000.

FIG. 10*a* depicts an example addition to a signal processing topology (perhaps, any one of the signal processing topologies previously presented in detail) that includes a variant of the filter block 350 having the ability to accept the input of feedforward reference data from two different feedforward microphones 130. More specifically, the filter block 350 is coupled to the ADC 310 to more directly receive feedforward reference data from the feedforward microphone 130 that is associated with the same one of the earpieces to which the one of the ANR circuits 2000 in which the filter block 350 resides is also associated. This coupling between the ADC 310 and the filter block 350 is made in one of the ways previously discussed with regard to the internal architectures 2200*a* and 2200*b*. However, the filter block 350 is also coupled to the interface 530 to receive other feedforward reference data from the feedforward microphone 130 that is associated with the other of the earpieces 100 through the interface 530 from the ANR circuit 2000 that is also associated with the other of the earpieces 100. Correspondingly, the output of the ADC 310 by which feedforward reference data is provided to the filter block 350 is also coupled to the interface 530 to transmit its feedforward reference data to the ANR circuit 2000 associated with the other one of the earpieces 100 through the interface 530. The ANR circuit 2000 associated with the other one of the earpieces 100 employs this same addition to its signal processing topology with the same variant of its filter block 350, and these two incarnations of the ANR circuit 2000 exchange feedforward reference data through their respective ones of the interface 530 across the bus 535 to which both incarnations of the ANR circuit 2000 are coupled.

FIG. **10*b* depicts another example addition to a signal processing topology that includes a variant of the filter block 350. However, this variant of the filter block 350 is involved in the transmission of feedforward reference data to the ANR circuit 2000 associated with the other one of the earpieces 100, in addition to being involved in the reception of feedforward reference data from that other incarnation of the ANR circuit 2000. Such additional functionality may be incorporated into the filter block 350 in implementations in which it is desired to in some way filter or otherwise process feedforward reference data before it is transmitted to the other incarnation of the ANR circuit 2000**.

Figure 11:
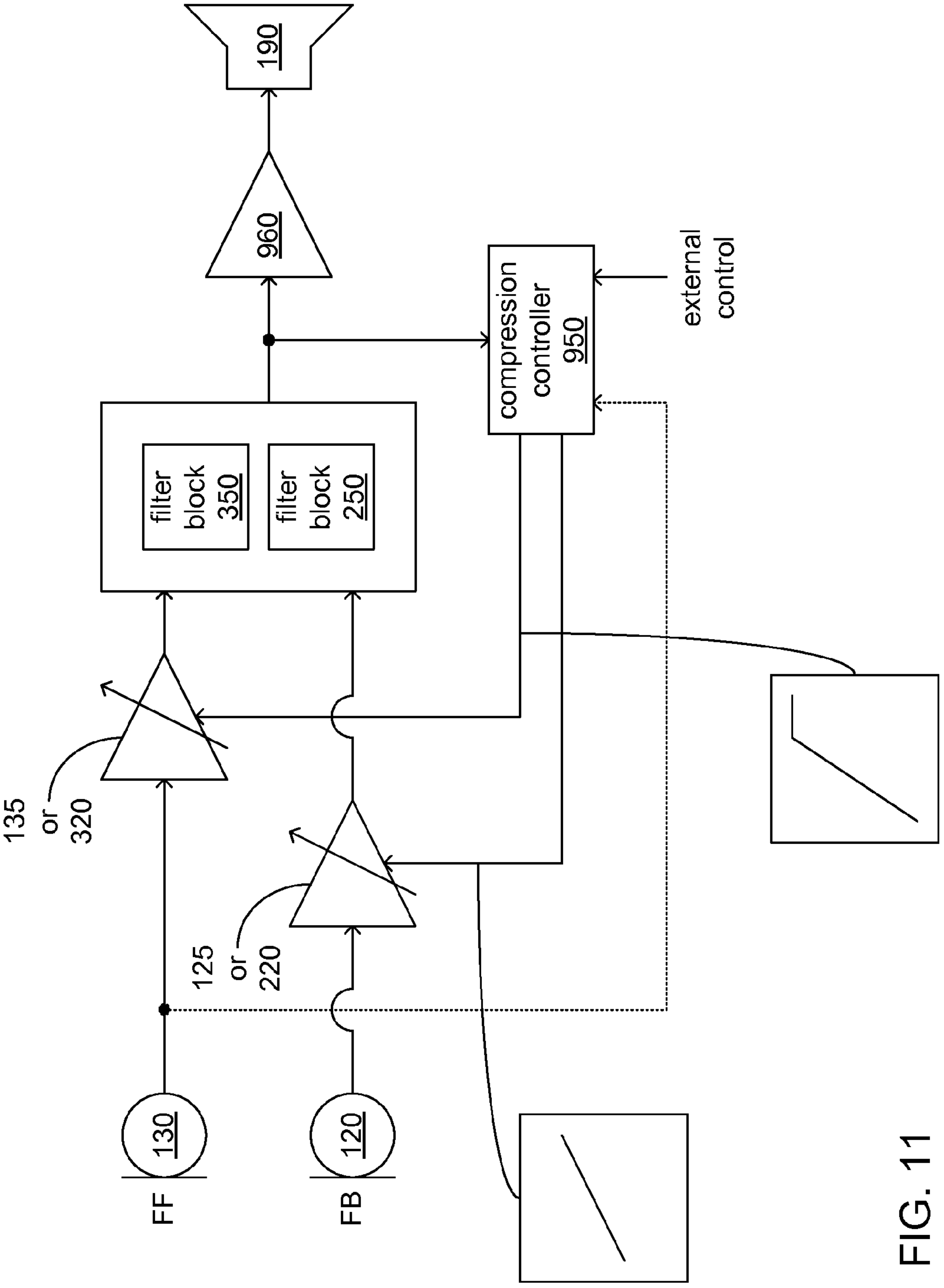
FIG. 11 depicts possible additional aspects of any of the signal processing topologies of FIGS. 4*a* through 4*g*

FIG. 11 depicts signal processing topology aspects of a coordinated compression of feedback and feedforward reference sounds in response to occurrences of excessively high environmental noise sound levels. In situations where environmental noise sounds reach sufficiently high levels of acoustic energy, one or both of feedback-based and feedforward-based ANR may be overloaded to the extent that the provision of ANR is compromised, and possibly to the extent that acoustic noise is actually generated. FIG. 11 presents a simplified depiction of additions and/or modifications that may be made to some signal processing topologies (such as the signal processing topologies **2500*a* through 2500*g* of FIGS. 4*a* through 4*g***, respectively) to perform such coordinated compression in such situations.

Regarding feedforward-based ANR, the diaphragm of the feedforward microphone 130 may be vibrated by such high environmental noise sound levels to such an extent that the voltage levels of the electrical signal output by the feedforward microphone 130 that is meant to represent the feedforward reference sounds may cease to have a linear relationship with the physical movement of its diaphragm, possibly to the extent that clipping occurs in that electrical signal. If such a clipped non-linear electrical signal is then used as a representation of feedforward reference sounds, then a clipped form of feedforward anti-noise sounds will be created that will be incapable of providing effective feedforward-based ANR. Further, the result may also be the generation of feedforward anti-noise sounds that actually include additional noise that effectively bring about a resulting amplification of environmental noise sounds as those clipped feedforward anti-noise sounds are acoustically output by the acoustic driver 190.

Further, regardless of whether or not feedforward anti-noise sounds are generated from a distorted electrical signal that is meant to represent feedforward reference noise sounds, such high environmental noise levels can cause the generation of feedforward and/or feedback anti-noise sounds having an amplitude sufficient that clipping occurs in the acoustic output of one or both of those anti-noise sounds as a result of limitations in the audio amplifier 960 and/or the acoustic driver 190 being reached. As those skilled in the art will readily recognize, occurrences of clipping (or other acoustic artifacts) in the acoustic output of sounds can cause those output sounds to be distorted. Where this happens to anti-noise sounds, the result can be a reduction in the degree of ANR provided, and possibly the generation of additional noise sounds.

Figure 4F:
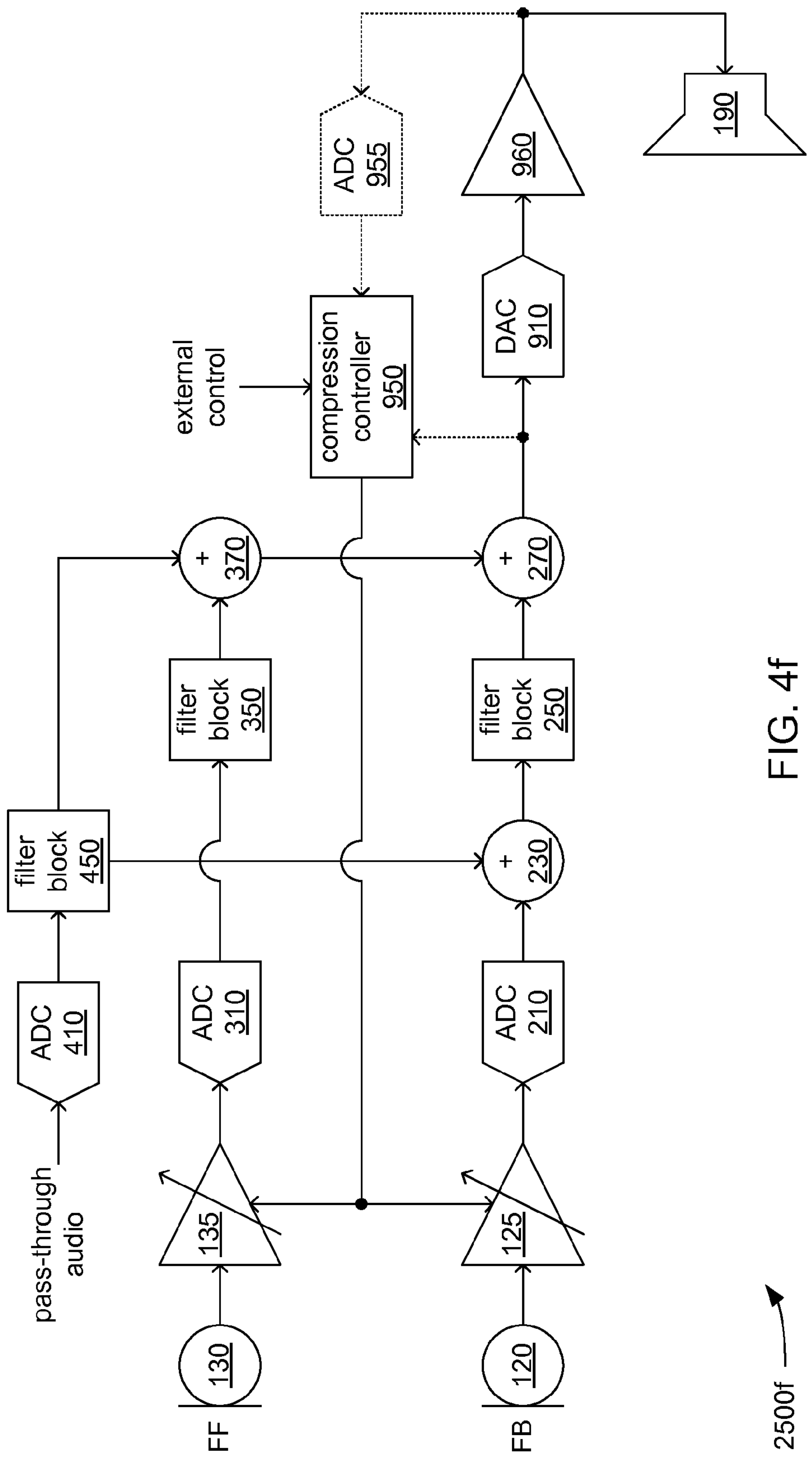
Figure 4G:
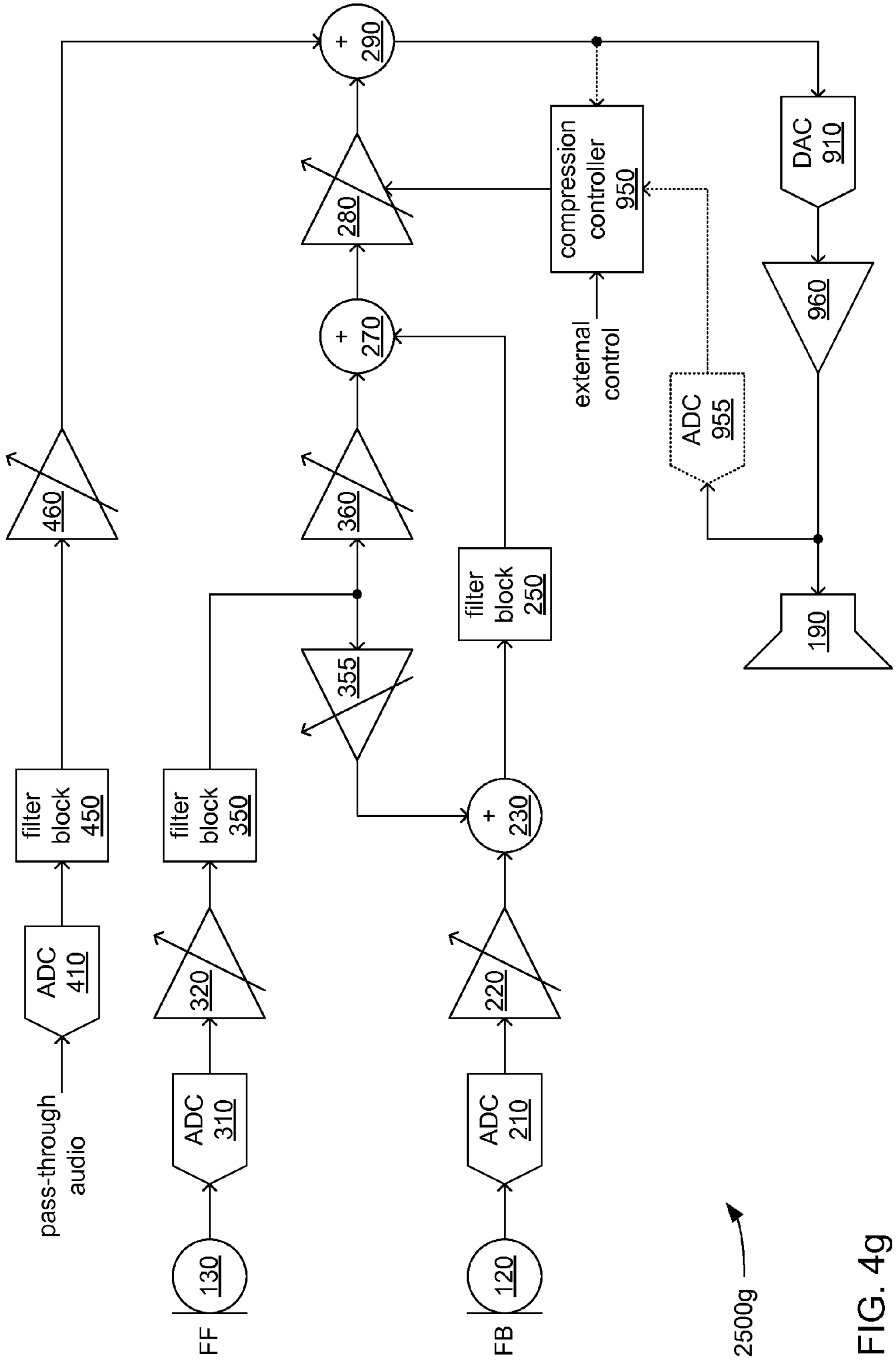

As has been previously discussed, both generally and more specifically in reference to the signal processing topologies **2500*f-g* depicted in FIGS. 4*f-g*, respectively, the compression controller 950 may respond to any of a number of events by operating the VGAs 125 and 135 (if present), the VGAs 220 and 320 (if present) and/or other VGAs that may be present to reduce the gain to which the feedback reference sounds and feedforward reference sounds, respectively, are subjected prior to being provided to various filters for the generation of anti-noise sounds (e.g., filter blocks 250 and 350). As has also been previously discussed, a pair of VGAs, such as the pair of analog VGAs 125 and 135 or the pair of digital VGAs 220 and 320, may be controlled in a coordinated manner, possibly to balance the relative amplitudes of analog signals representing the feedback and feedforward reference sounds, and/or possibly to limit the numeric values of digital data conveyed with digital signals representing the feedback and feedforward reference sounds. In other words, a pair of VGAs, such as the pair of analog VGAs 125 and 135 or the pair of digital VGAs 220 and 320**, may be controlled in a coordinated manner balance the relative amplitudes of feedback and feedforward reference sounds (whether represented in analog or digital form).

More specifically and as is depicted in FIG. 11, the compression controller 950 may operate either the pair of VGAs 125 and 135 or the pair of VGAs 220 and 320 to reduce the gains to which signals representing feedback reference sounds and feedforward reference sounds are subjected in a coordinated manner in response to receiving an indication that environmental noise sounds (such as those emanating from the acoustic noise source 9900) have reached at least one predetermined level of acoustic energy (e.g., a predetermined sound pressure level). This may be done by directly monitoring the amplitude of feedforward reference sounds as detected by the feedforward microphone 130 (as specifically depicted in FIG. 11). In some embodiments, that indication may be an occurrence of an acoustic artifact or an amplitude exceeding a predetermined level detected in signals conveying feedforward reference sounds from the feedforward microphone 130. In other embodiments, that indication may be an occurrence of an acoustic artifact (e.g., clipping) or an amplitude of a sound exceeding a predetermined level detected by the compression controller 950 in a signal conveying at least an anti-noise sound to be acoustically output by the acoustic driver 190 (as specifically depicted in FIG. 11). In still other embodiments, that indication may be an occurrence of an acoustic artifact or an amplitude of a sound exceeding a predetermined level detected by the compression controller 950 anywhere along the feedback-based ANR pathway 200 and/or the feedforward-based ANR pathway 300. In yet other embodiments, that indication may be an external control signal received from another device (not shown), where that other device may have in some way determined that the acoustic level of an environmental noise sound has reached a predetermined level.

Attenuating both the feedforward and feedback reference sounds in a coordinated manner serves to avoid situations in which relative differences in strengths of the resulting feedforward and feedback anti-noise sounds are allowed to differ too greatly. For example, if feedforward reference sounds are not attenuated as feedback reference sounds are attenuated such that the strength of the feedforward reference sounds is allowed to far exceed that of the feedback reference sounds, saturation of the compression of the feedback reference sounds may occur. As those skilled in the art of combining feedforward-based and feedback-based ANR will readily recognize, where the feedforward ANR anti-noise sound is summed towards the feedback loop output, the strength of feedforward anti-noise sounds is reduced by the desensitivity of the loop that is formed in implementing feedback-based ANR, and the strength of feedforward anti-noise sounds will then increase as gain in the loop of the feedback-based ANR is decreased by compressor action. In some embodiments, this increase in the strength of the feedforward anti-noise sounds can, if allowed to become too great relative to the strength of the feedback anti-noise sounds, actually induce further compression in the feedback-based ANR loop to the point of compression saturation such that the strength of feedback anti-noise sounds is actually reduced to a degree that the provision of feedback-based ANR is fully lost. Further, the resulting absence of feedback-based ANR can induce still further increases in the strength of the feedforward anti-noise sounds in an effort to compensate for the absence of feedback-based ANR. Under these conditions, the feedforward anti-noise sounds could be supplied to the audio amplifier 960 and/or the acoustic driver 190 with such strength that clipping of the feedforward anti-noise sounds occurs as a result of limitations in the audio amplifier 960 to amplify audio and/or in the acoustic driver 190 to acoustically output audio being reached or exceeded, thereby further compromising the provision of ANR.

As is also more specifically depicted in FIG. 11, the compression controller 950 may operate a pair of VGAs to compress signals representing feedforward reference sounds with a steeper slope of attenuation than signals representing feedback reference sounds. In other words, the compression controller 950 may operate the pair of VGAs to compress the amplitude of the feedforward reference sounds to a greater degree than the feedback reference sounds. This may be done in an effort to avoid occurrences of the aforedescribed scenario of saturation of compression in the loop of the feedback-based ANR. It may also be deemed desirable to do this in recognition of the more direct and greater effect that environmental noise sounds are likely to have on the feedforward microphone 130 than on the feedback microphone 120.

Variable degrees of compression may be employed in embodiments in which the compression controller 950 is provided with indications of amplitudes, voltage levels and/or magnitudes of data values of signals conveying either feedforward reference sounds or anti-noise sounds for acoustic output, wherein the variable degrees of attenuation of the feedforward and feedback reference noise sounds are derived in relation to such amplitudes, voltage levels and/or magnitudes. It should be noted that although FIG. 11 depicts substantially linear slopes of attenuation as being employed by the compression controller in operating a pair of VGAs, non-linear curves representing any of a variety of linear and/or non-linear relations between the degrees of attenuation that may be employed and one or more of amplitudes, voltage levels, magnitudes and/or signal time histories.

As if further more specifically depicted in FIG. 11, the compression of at least the feedforward reference sound may level off after reaching a certain degree of compression. Given that the degree of compression of the feedforward reference sound may, in some embodiments, be increased at a greater rate than the degree of compression of the feedback reference sound (again, as indicated by the depicted steeper slope), it may be that this leveling off of the compression of the feedforward reference sound is a result of the maximum possible compression of the feedforward reference sound being reached before the maximum possible compression of the feedback reference sound is reached. In other words, whatever VGA is employed in compressing the feedforward reference sound may be operated such that the feedforward reference sound is compressed to the extent that its amplitude is reduced to close to zero (possibly reduced fully to zero) while the feedback reference sound is not. Alternatively, limitations in whatever VGA or other component is involved in compressing the feedforward reference sound may set a maximum degree of compression of the feedforward reference sound that cannot be exceed. Alternatively and/or additionally, other design considerations may result in it being deemed in some way desirable that the degree of compression of the feedforward reference sound never be allowed to reach the extent that its amplitude is reduced close to zero (or reduced fully to zero).

Figure 12A:
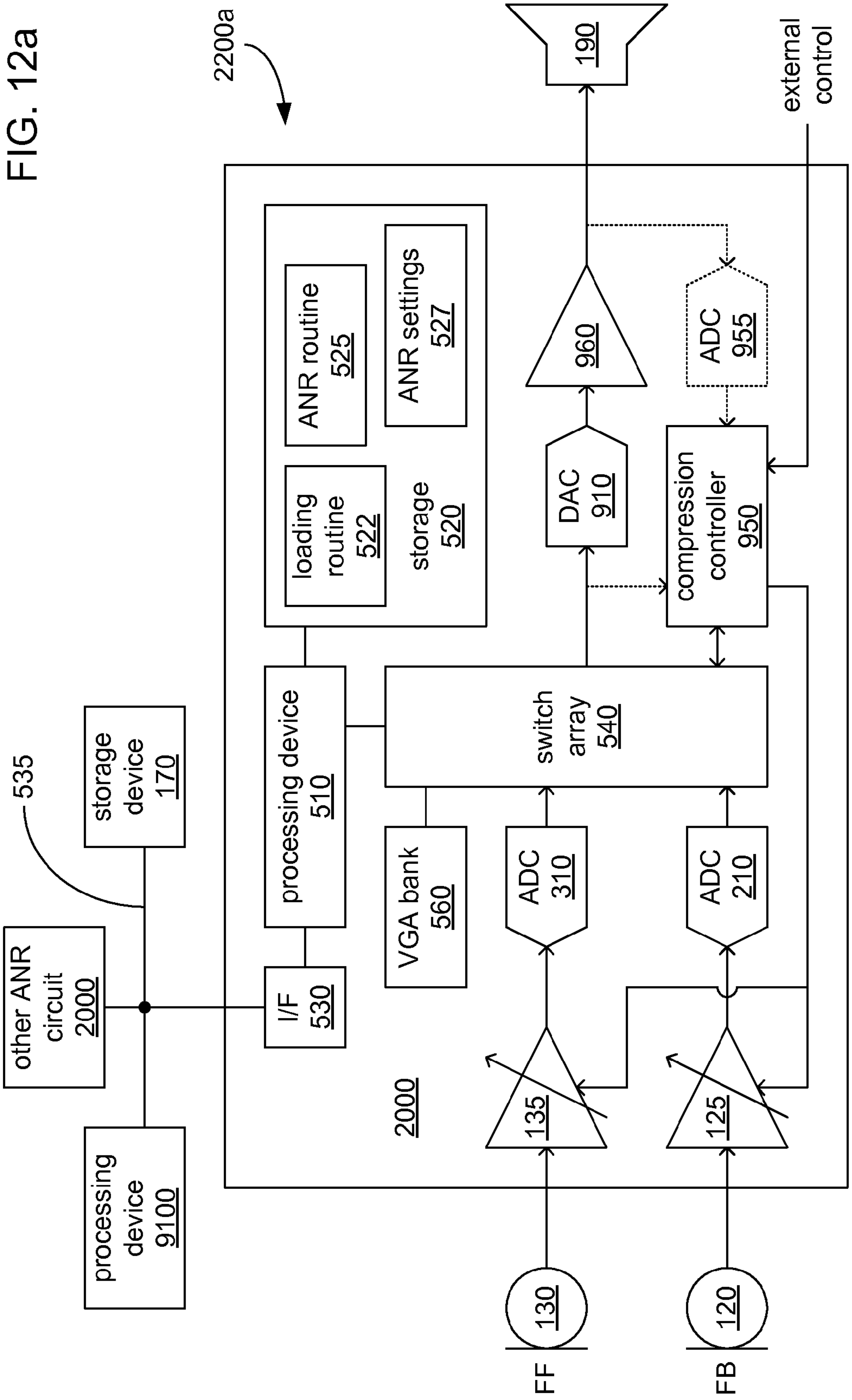
FIG. 12*a* depicts a possible additional portion of the internal architecture of FIG. 3*a*.
Figure 12B:
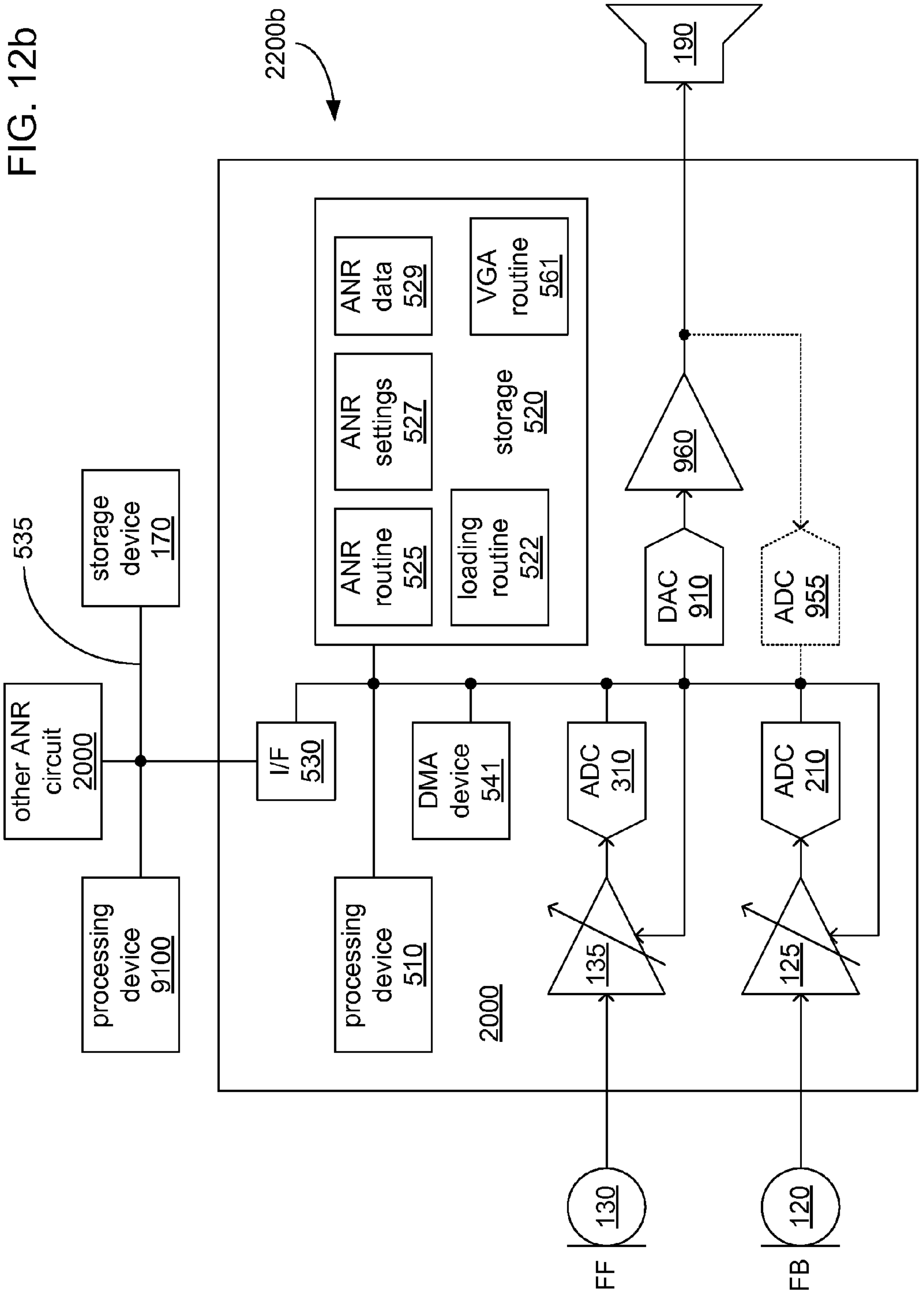
FIG. 12*b* depicts a possible additional portion of the internal architecture of FIG. 3*b*.

FIGS. 12*a* and 12*b* each depict variations of a number of possible additions to the internal architectures 2200*a* and 2200*b*, respectively, of the ANR circuit 2000. Therefore, it should be noted that for sake of simplicity of discussion, only portions of the internal architectures 2200*a* and 2200*b* associated with these possible additions are depicted, while other portions (e.g., portions related to pass-through audio that may be present) are omitted. Some of these possible additions rely on the use of the interface 530 coupling the ANR circuit 2000 to other devices via at least one bus 535.

More particularly, in preparation for operating either the pair of VGAs 125 and 135 (if present) or the pair of VGAs 220 and 320 (wherein the VGAs 220 and 320 are either selected from the VGA bank 560 or instantiated from the VGA routine 561), the processing device 510 may be caused (perhaps by the loading routine 522) to configure the ANR circuit 2000 to accept data specifying coordinated gain values from the storage device 170, another ANR circuit 2000 and/or a processing device 9100. In some embodiments, the data specifying coordinated gain values may be made up of one or more pairs of gain values to be provided to either the pair of VGAs 125 and 135 or the pair of VGAs 220 and 320 in response to an occurrence of the acoustic energy (e.g., sound pressure level) of environmental noise sounds reaching at least one predetermined level. In such embodiments, the one or more pairs of gain values may be stored in the storage 520 as part of the ANR settings 527, and/or may be provided in real time from one or both of the other ANR circuit 2000 and the processing device 9100 during normal operation of the personal ANR device 1000. In other embodiments, the data specifying coordinated gain values may be data specifying mathematic or other relationships by which coordinated gain values may be mathematically (or in some other way) derived from an amplitude, voltage level, magnitude or signal time history by the processing device 510 as part of executing the ANR routine 525.

Where coordinated gain values are received by the ANR circuit 2000 through the interface 530 from another device, and where that other device is the other ANR circuit 2000, the coordinated gain values may be provided in response to a feedforward microphone (not shown) of the other ANR circuit 2000 encountering environmental noise sounds having an energy level that reached at least one predetermined level. This may occur where a feedforward microphone of the other ANR circuit 2000 encounters such environmental noise sounds in a situation where the feedforward microphone 130 does not, or where the feedforward microphone of the other ANR circuit 2000 encounters such environmental noise sounds sooner than the feedforward microphone 130. Such conveyance of coordinated gain values between the ANR circuit 2000 and the other ANR circuit 2000 may occur as part of the provision of binaural feedforward-based ANR as previously described.

Where coordinated gain values are received by the ANR circuit 2000 through the interface 530 from another device, and where that other device is the processing device 9100, the coordinated gain values may be provided in response to one or both of the feedforward microphone 130 and another feedforward microphone (not shown) of the other ANR circuit 2000 encountering environmental noise sounds having an energy level that reaches a predetermined level. The processing device 9100 may normally be employed to execute a sequence of instructions that causes the processing device 9100 to perform one or more forms of analysis on at least feedforward reference sounds detected by the feedforward microphone 130 and/or the other feedforward microphone, but may also be further employed to function as a form of compression controller to provide the coordinated gain values to the ANR circuit 2000.

Regardless of the manner in which the coordinated gain values for a pair of VGAs are either received or derived, the manner in which they are provided to a pair of VGAs may entail the use of triple-buffering as previously described. In some embodiments, the buffers 620*a* and 620*b* (see FIGS. 6*a* through 6*c*) are employed in making timing-coordinated changes of at least the gain settings of at least the pair of VGAs 125 and 135 (if present) or the VGAs 220 and 320 (if present), while the buffer 620*c* holds coordinated gain values deemed to be conservative enough to be a "failsafe" pair of gain values to be used in instances where instability in the provision of ANR is detected.

Turning to FIG. 12*a* and as has been previously described, in the internal architecture 2200*a*, the compression controller 950 may be implemented as distinct circuitry within the ANR circuit 2000. Turning to FIG. 12*b* and has also been previously described, in the internal architecture 2200*b*, the compression controller 950 may be caused to be implemented by the processing device 510 as a result of executing a sequence of instructions of the ANR routine 525. Either implementation of the compression controller 950 may monitor characteristics of anti-noise sounds to be acoustically output by the acoustic driver 190 either by receiving the digital data provided to the DAC 910 or by receiving digital data generated by the ADC 955 (if present) from the analog signal output by the audio amplifier 960. This may be done in addition to monitoring characteristics of feedforward reference noise sounds detected by the feedforward microphone 130, as has been described at length. Again, despite such specific depictions of the manner in which the compression controller 950 (whether implemented with distinct circuitry or as a sequence of instructions executed by a processing device) monitors sounds being acoustically output, as previously discussed, the compression controller 950 may more directly monitor feedforward reference sounds as detected by the feedforward microphone 130 and/or may monitor sounds at other locations along one or both of the feedback-based ANR pathway 200 and the feedforward-based ANR pathway 300.

It should be noted again that although implementations of the ANR circuit 2000 employing at least some digital circuitry have been depicted and discussed at length herein, those skilled in the art will readily recognize that each of the many embodiments of signal processing topologies and portions of signal processing topologies depicted and discussed herein may be implemented, either partially or entirely, using analog circuitry. Thus and more specifically, the modifications and/or portions of signal processing topologies depicted in FIG. 11 to implement the coordinated compression of feedforward and feedback reference sounds may be implemented entirely using analog circuitry.

Figure 13:
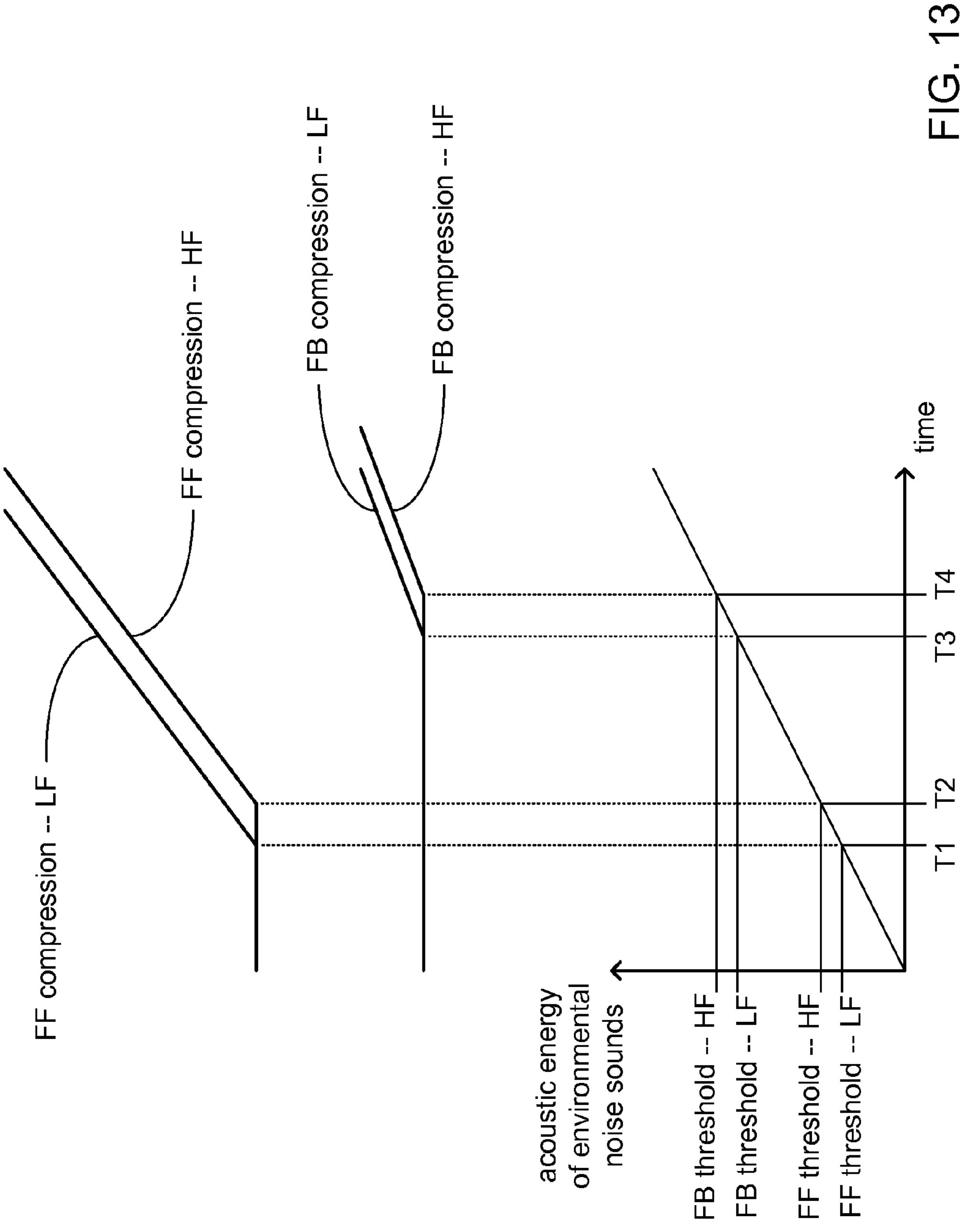
FIG. 13 depicts possible coordinated compression responses to various acoustic energy levels of noise sounds at various frequencies of noise sounds.

FIG. 13 more clearly depicts an example of coordinated compression of both feedforward and feedback reference sounds with differing slopes, as previously discussed. FIG. 13 also depicts an example of using different predetermined threshold levels of acoustic energy in triggering the start of compression of feedforward reference sounds versus the start of compression of feedback reference sounds, and further depicts an example of using threshold levels that are dependent on frequency characteristics of the environmental noise sounds detected by the feedforward microphone 130.

It should be noted that although a linear rise in the acoustic energy of environmental noise sounds over a period of time is depicted, such a depiction should not be taken as limiting the scope of what is described or what is claimed herein to responding only to such an orderly and steady change in acoustic energy of environmental noise sounds, and should not be taken as reflecting a belief that such behavior of environmental noise sounds is in any way expected in real world conditions. It is to be understood that this very simplistic depiction of such an orderly and steady change in acoustic energy of environmental noise sounds is presented only to enable a greater understanding of the manner in which different levels of acoustic energy of environmental noise sounds may be responded to by what is described and what is claimed herein.

As depicted, as the level of acoustic energy of the environmental noise sounds (such as those emanating from the acoustic noise source 9900) increases, a predetermined threshold level of acoustic energy is reached at either T1 or T2 that serves as a trigger for causing the compression of feedforward reference sounds to begin. As the level of acoustic energy of the environmental noise sounds continues to increase, the degree of compression of feedforward reference sounds increases. As the level of acoustic energy of the environmental noise sounds still continues to increase, another predetermined threshold level of acoustic energy is reached at either T3 or T4 that serves as a trigger for causing the compression of feedback reference sounds to begin. As the level of acoustic energy of the environmental noise sounds yet continues to increase, the degree of compression of feedback reference sounds increases, as does also the degree of compression of feedforward reference sounds, although as is also depicted, the increases in compression of feedforward reference sounds occur at a greater rate following a steeper slope than the increases in compression of feedback reference sounds.

As also depicted, in some embodiments, the threshold levels of acoustic energy of environmental noise sounds may change depending on frequency characteristics of the environmental noise sounds. By way of example, the threshold level of acoustic energy at which compression of feedforward reference sounds is triggered may be changed such that it's reached either at T1 or T2, depending on whether the predominant frequencies of the environmental noise sounds are lower frequencies (such that the threshold is reached at T1) or higher frequencies (such that the threshold is reached at T2). Similarly, the threshold level of acoustic energy at which compression of feedback reference sounds is triggered may be changed between being reached at T3 or T4, depending on whether the predominant frequencies of the environmental noise sounds are lower frequencies (such that the threshold is reached at T3) or higher frequencies (such that the threshold is reached at T4).

This dependency of thresholds on frequency characteristics of environmental noise sounds may be employed in recognition of the different ranges of frequencies at which each form of noise reduction typically functions. Typically, the PNR provided by casing 110, ear coupling 115 and/or other physical features of the personal ANR device 1000 reduces environmental noise sounds to a greater degree at higher frequencies, the feedforward-based ANR acts to reduce environmental sounds at lower frequencies, and the feedback-based ANR acts to reduce environmental sounds at still lower frequencies. Thus, the feedforward-based and feedback-based ANR are more likely to be adversely affected by environmental noise sounds having very high acoustic energy levels at lower frequencies such that compression of feedforward and/or feedback reference sounds may provide greater benefits at lower frequencies. Therefore, where environmental noise sounds are made up of predominantly lower frequency sounds, the threshold(s) at which compression of feedforward and/or feedback reference sounds may be lowered such that compression of feedforward reference sounds is triggered at T1 (instead of at T2) and/or compression of feedback reference sounds is triggered at T3 (instead of T4).

Alternatively and/or additionally, this dependency of thresholds on frequency characteristics of environmental noise sounds may be employed in recognition of possible limitations of the acoustic driver 190 in acoustically outputting sounds of certain audible frequencies and/or ranges of audible frequencies. As will be familiar to those skilled in the art, it is common for acoustic drivers to acoustically output a sound of one audible frequency with greater acoustic energy than another sound of a different audible frequency despite such acoustic drivers being driven by an audio amplifier with equal electrical energy to acoustically output both sounds. Given that the earlier-described feedback-based ANR loop includes the acoustic driver 190, which may be subject to such limitations, it may be deemed desirable to select the thresholds by which the compression of feedforward reference sounds and the compression of feedback reference sounds are each triggered by environmental noise sounds of predominantly higher frequencies and of predominantly lower frequencies at least partly in recognition of those limitations.

The compression controller 950 may incorporate one or more filters to separate the feedforward reference sounds represented by signals provided to the compression controller 950 from the feedforward microphone 130 into sounds within two or more ranges of frequencies, and/or to determine the relative acoustic energies of the sounds within those two or more ranges of frequencies. Alternatively and/or additionally, filters of one or more of the filter blocks 250, 350 and 450 may be employed, perhaps in a manner in which the compression controller 950 receives the feedforward reference sounds in a form that is already separated into those two or more ranges of frequencies In the internal architecture 2200*a*, those filters may be provided from the filter bank 550. In the internal architecture 2200*b*, those filters may be instantiated and implemented by the processing device 510 through execution of one or more of the filter routines 553, 555, 557 and 559.

Figure 14:
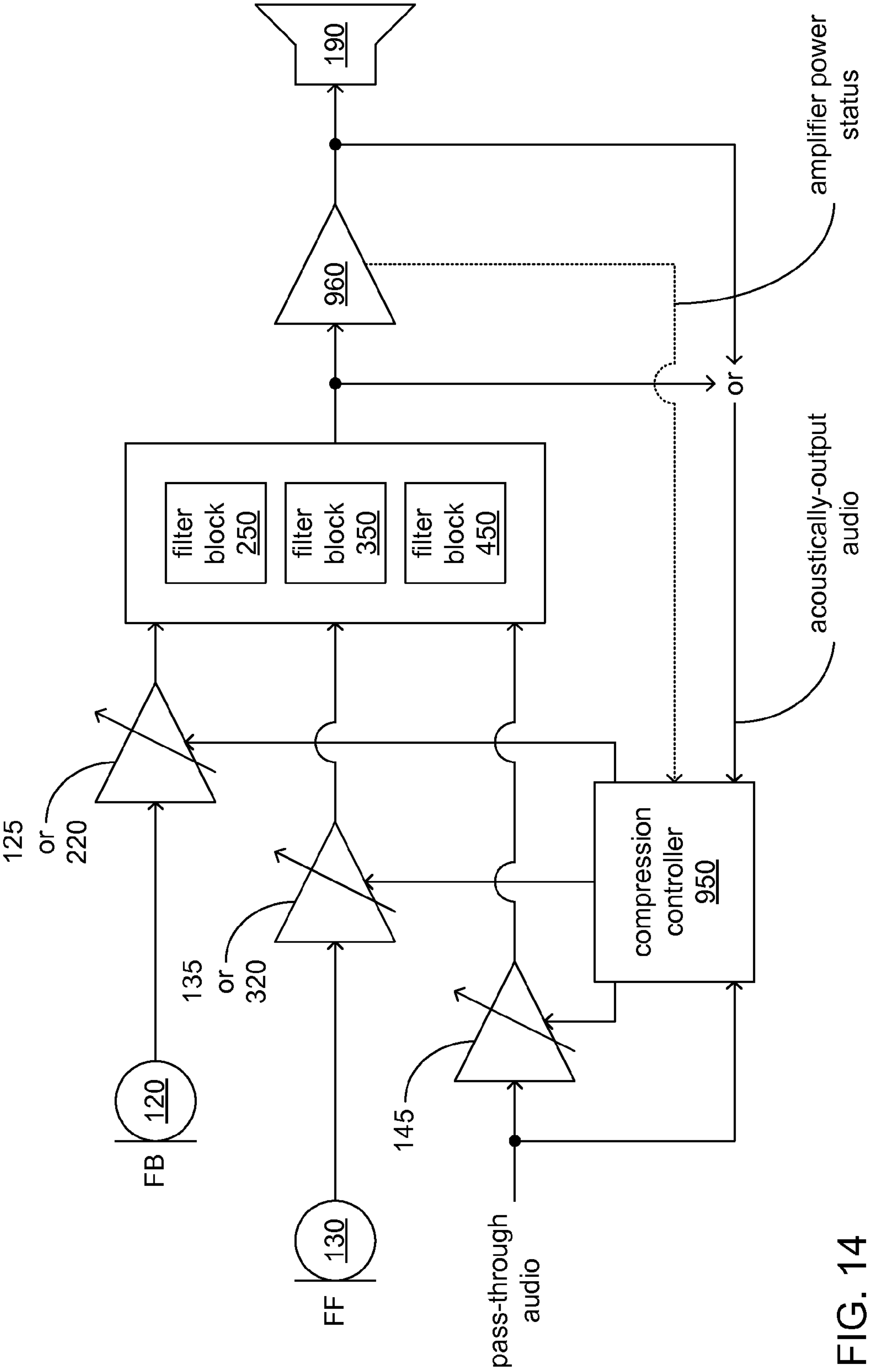
FIG. 14 depicts possible additional aspects of any of the signal processing topologies of FIGS. 4*a* through 4*g*.

FIG. 14 depicts signal processing topology aspects of an embodiment of instability detection. More specifically, FIG. 14 presents a simplified depiction of additions and/or modifications that may be made to a signal processing topology (such as the signal processing topologies 2500*a* through 2500*g* of FIGS. 4*a* through 4*g*, respectively) to detect instances of instability in the provision of feedback-based ANR. As will be explained in greater detail, a phase-locked loop (PLL) of the compression controller 950 is employed in analyzing the sounds to be acoustically output by the acoustic driver 190 for an instance of instability. This acoustically-output audio includes at least the feedback anti-noise sounds derived by filters of at least the filter block 250 from feedback reference noise sounds detected by the feedback microphone 120. However, embodiments are also possible in which the acoustically-output audio also includes one or both of feedforward anti-noise sounds derived by filters of at least the filter block 350, and/or pass-through audio that may be modified in any of a variety of ways (as has been previously discussed) by filters of at least the filter block 450. Where one or the other of the filter blocks 350 and 450 are present, there output may be combined with that of the filter block 250 in any of a variety of ways, as has already been presented and discussed.

The compression controller 950 is coupled to the output of at least the filter block 250, which may be summed with the outputs of one or both of the filter blocks 350 and 450, depending on which ones of the feedforward-based ANR and pass-through audio functions are also provided. As has been earlier depicted and discussed, where the compression controller 950 is implemented at least partially with analog circuitry, the compression controller 950 may be capable of directly accepting an analog signal that represents the acoustically-output audio, either before or after that analog signal is amplified by the audio amplifier 960. Alternatively and/or additionally, where the compression controller 950 is at least partially implemented with digital circuitry (either as a distinct digital circuit or as a sequence of instructions executed by a processing device), the compression controller 950 may receive digital data representing the acoustically-output audio directly from the filter block 250, directly from a summing node in an instance where digital data output by the filter block 250 is summed with other digital data, or from the ADC 955 converting an analog signal representing the acoustically-output audio into digital data either before or after that analog signal is amplified by the audio amplifier 960.

It should be noted that despite the depiction in FIG. 14 of there being pass-through audio and of the VGA 145 and the filter block 450 being present to support the reception, possible modification, and acoustic output of pass-through audio, embodiments of the ANR circuit 2000 and/or of the personal ANR device 1000 are possible in which the acoustic output of a pass-through audio of some form is not supported. Where there is no support for pass-through audio, the compression controller 950 employs a PLL to analyze the acoustically-output audio for the presence of a sound that has a frequency within a predetermined range of frequencies and that has a predetermined minimum amplitude that is indicative of growing instability in the provision of feedback-based ANR, as well as having a sinusoidal waveform that is usually also indicative of instability. Where there is support for pass-through audio, the compression controller employs the pass-through audio (received from whatever source of pass-through audio) to distinguish what may be a sound indicative of growing instability from the pass-through audio that is also present within the acoustically-output audio.

In embodiments in which the acoustic output of pass-through audio is supported, the compression controller 950 receives the pass-through audio from whatever source from which a user of the personal ANR device 1000 chooses to provide pass-through audio to be acoustically output by the acoustic driver 190 along with anti-noise sounds. In some embodiments of the personal ANR device 1000, the source of the pass-through audio may be a device separate from, but in some way coupled to, the personal ANR device 1000 (e.g., a radio, a disc player, etc., coupled via a cable or wirelessly to the personal ANR device 1000). In other embodiments, the source of the pass-through audio may be an audio storage device incorporated into the personal ANR device 1000 (e.g., a solid-state storage device, a tuner, etc.). Again, where the compression controller 950 is implemented at least partially with analog circuitry, the compression controller 950 may be capable of directly accepting an analog signal that represents the pass-through audio. Alternatively and/or additionally, where the compression controller 950 is at least partially implemented with digital circuitry, the compression controller 950 may receive digital data representing the pass-through audio (perhaps through the ADC 410, where an analog signal from the source is converted into the digital data).

Figure 15:
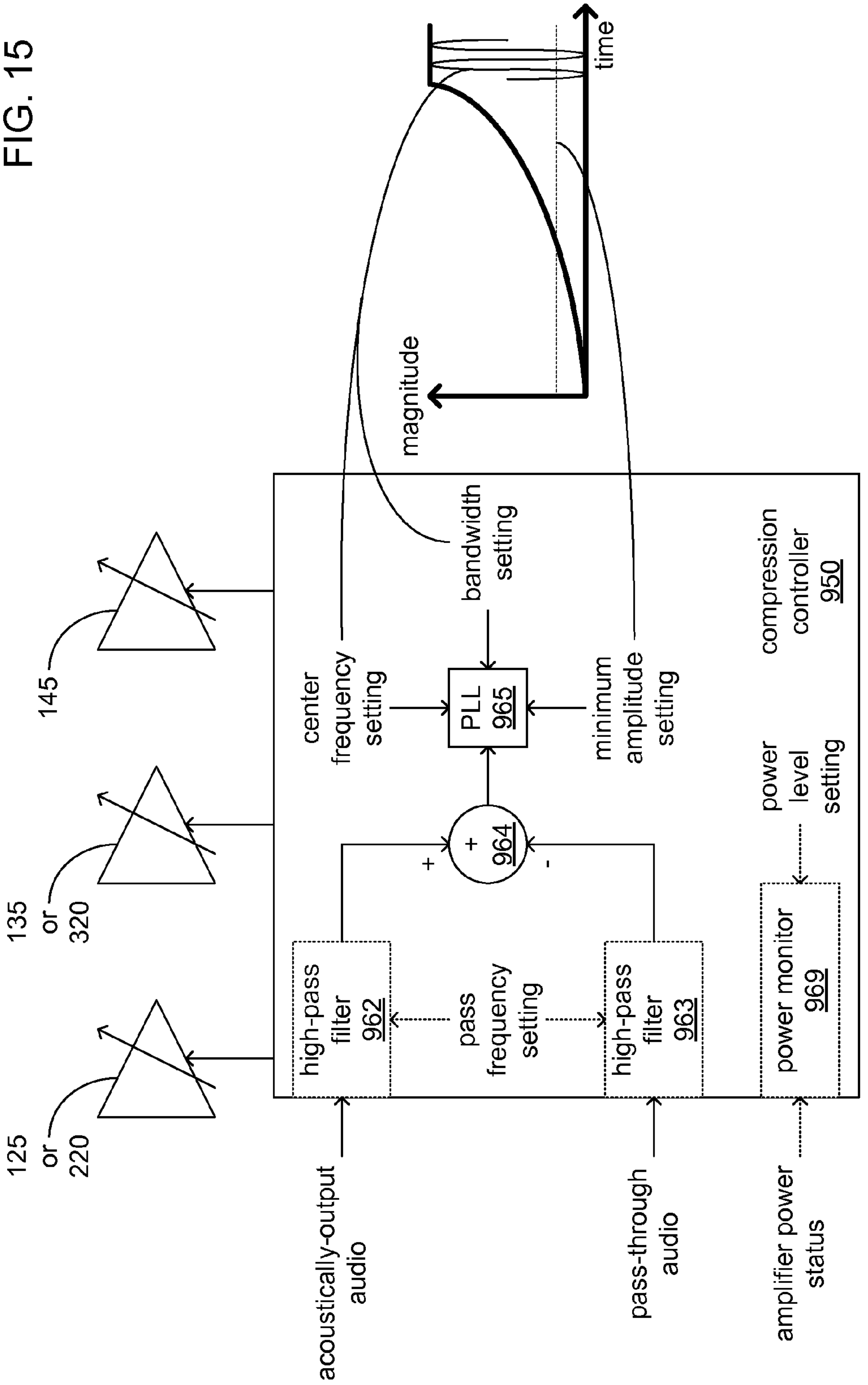
FIGS. 15 and 16 depict a possible additional portion of either of the internal architectures of FIGS. 3*a* and 3*b*.

FIG. 15 depicts aspects of an internal architecture that may be employed by embodiments of the compression controller 950 in which the compression controller 950 incorporates at least a PLL 965. Where the acoustic outputting of pass-through audio is not supported, the PLL 965 is a portion of the compression controller 950 that more directly receives the acoustically-output audio, and analyzes the acoustically-output audio for the presence of a sound having a frequency within a predetermined range of frequencies and that has a minimum amplitude indicative of instability in the provision of feedback-based ANR, as well as possibly also having a sinusoidal waveform that is usually also indicative of instability. As those familiar with the operation of a PLL will readily recognize, the PLL 965 is provided with a center frequency setting, a bandwidth setting, and a minimum amplitude setting. The center frequency setting and bandwidth setting are employed to configure the PLL 965 to lock onto only sounds within the acoustically-output audio that have a frequency within the limits of the range of frequencies specified by the bandwidth setting, where the range of frequencies is centered on the frequency specified by the center frequency setting. Further, as those skilled in the art of the use of PLLs will readily recognize, the PLL 965 may be configured to lock onto only sounds of such frequencies if those sounds have a sinusoidal waveform. Still further, the minimum amplitude setting is employed to configure the PLL 965 to lock onto sounds of such frequencies only if those sounds have at least the amplitude specified by the minimum amplitude setting.

Where the acoustic outputting of pass-through audio is supported, the compression controller further incorporates at least a summing node 964 that is interposed between the PLL 965 and the acoustically-output audio, and which also receives the pass-through audio. The summing node 964 is a subtractive summing node that subtracts the pass-through audio from the acoustically-output audio in an effort to provide a modified form of the acoustically-output audio that is stripped of the pass-through audio. This is done in an effort to prevent occurrences of false indications of there being a sound having a frequency and both of the sinusoidal waveform and minimum amplitude that are indicative of instability as a result of the pass-through audio coincidentally having such a sound within it. Thus, the PLL 965 analyzes this modified form of the acoustically-output audio for sounds having a frequency within the limits of the range of frequencies specified by the bandwidth setting, where the range of frequencies is centered on the frequency specified by the center frequency setting, where those sounds have at least the amplitude specified by the minimum amplitude setting, and perhaps where those sounds have a sinusoidal waveform.

As indicated with dotted lines in FIG. 15, one or both of the acoustically-output audio and the pass-through audio may additionally be routed through high-pass filters 962 and 963, respectively, that may also be incorporated into the compression controller 950. The high-pass filter 962 may be interposed between the acoustically-output audio received by the compression controller 950 and one or the other of the PLL 965 or the summing node 964. Alternatively and/or additionally, the high-pass filter 963 may be interposed between the pass-through audio received by the compression controller 950 and the summing node 964. The high-pass filters 962 and 963 serve to filter out signals having a frequency lower then the pass frequency setting provided to the high-pass filters 962 and 963, where the pass frequency setting preferably specifies a frequency similar to the frequency at the lower limit of the range of frequencies specified for the PLL 965 by the combination of the center frequency and bandwidth settings. This filtering out of lower frequency signals enables the minimum amplitude setting provided to the PLL 965 to be set to specify lower amplitude levels. Without the high-pass filters 962 and 963, lower frequency sounds within either of the acoustically-output audio or the pass-through audio may cause false positive indications of there being a sound having a frequency and minimum amplitude that is indicative of instability. More specifically, a sound having a frequency within the range of frequencies specified by the bandwidth and center frequency settings, but having an amplitude that is less than the minimum amplitude, may be caused by the addition of an amplitude of a lower frequency sound to appear to have at least the requisite minimum amplitude specified by the minimum amplitude setting such that the PLL 965 is caused to falsely detect the presence of a sound having a frequency and minimum amplitude indicative of instability (and possibly also having a sinusoidal waveform that is also usually indicative of instability).

Although not specifically depicted in FIG. 15, it should be noted that where the compression controller 950 employs both of the acoustically-output audio and the pass-through audio in detecting instability, one or more VGAs (or other devices able to be employed to alter audio amplitudes) may be incorporated into the compression controller 950 to adjust relative amplitudes of one or both of the acoustically-output audio and the pass-through audio. This may be necessary, especially where the acoustically-output audio is received at a point following its amplification by the audio amplifier 960, and/or where the pass-through audio is received from a source at a level of amplification that differs greatly from that of the acoustically-output audio so as to balance their relative amplitudes and thereby enable proper results from the subtraction of one from the other by the subtraction node 964. Such VGA(s) (or other components) may be positioned to adjust amplitudes either before or after each of these pieces of audio is routed through one of the high-pass filters 962 and 963, where one or both of the high-pass filters 962 and 963 are present.

FIG. 15 further depicts the manner in which a sound associated with instability in the provision of feedback-based ANR starts and then increases exponentially in amplitude over time. The minimum amplitude setting is selected to be high enough to avoid false detections of such sounds due to acoustic and/or electrical noise, but low enough to detect the onset of instability relatively quickly so as to enable action to be taken quickly enough to try to avoid instances of a user of the personal ANR device 1000 hearing the characteristic "squealing" or "howling" sound that is so often associated with instability. Preferably, such a sound is detected while its amplitude is still low enough that it is sufficiently masked by electrical and/or acoustic noise that the user never notices it before action is taken to remove such a sound by counteracting the instability causing it.

The range of frequencies specified by the center frequency and bandwidth settings provided to the PLL 965 (and the corresponding pass frequency specified by the pass frequency setting provided to one or both of the high-pass filters 962 and 963, if present) is chosen based on the known electrical and acoustic characteristics of at least some of the components making up one of the earpieces 100 of the personal ANR device 1000. Factors such as sampling rates of digital circuits, propagation delays and phase shifts, microphone and acoustic driver characteristics in converting between mechanical and electrical energy, and frequency limitations of components due to both mechanical and electrical characteristics can interact to predispose a system (such as the components involved in providing feedback-based ANR in one of the earpieces 100 of the personal acoustic device 100) to developing a positively reinforcing feedback loop within a narrow range of frequencies as part of becoming unstable. This narrow range can generally be predicted through an analysis of these various characteristics of these components, thus enabling the PLL 965 to be configured with these settings to analyze the acoustically-output audio for the presence of a sound having such a frequency, as has been described. Further, as those skilled in the art will readily recognize, a sound associated with such instability typically has a sinusoidal waveform, and PLLs may be configured to lock onto only sinusoidal waveforms. Thus, the PLL 965 may be configured to aid in distinguishing a sound associated with instability from other sounds that are not so associated by inherently ignoring sounds that do not have a sinusoidal waveform. In analyzing audio for an indication of instability, the PLL 965 detects a sound having these characteristics that are indicative of instability by locking onto that sound, if that sound is present. If the PLL 965 does lock onto such a sound, then the compression controller 950 determines that there is an instance of instability and takes any of the variety of actions that have been previously described in response, including and not limited to, compressing one or both of feedback and feedforward reference noise sounds. Where the PLL 965 does not lock onto such a sound, then the compression controller 950 determines that there is no instability.

Further, as those skilled in the art will also recognize, as a system (such as the components of one of the earpieces 100 employed in providing feedback-based ANR) becomes unstable and a positive reinforcing feedback loop with a sound within that narrow range of frequencies develops, a greater than normal amount of electrical power may be drawn by at least such components as the audio amplifier 960 as the positive reinforcing nature of the feedback loop tends to drive that sound to ever increasing levels of amplitude. Further, unlike increases in the acoustic energy of environmental noises or other event that may cause a sudden increase in the amplitude of anti-noise acoustic output that tends to be of short duration, and unlike an increase in the amplitude of music provided as the pass-through audio that also tends to be of short duration, an instance of instability tends to continue until action is taken to counteract the continuation of that instance of instability. Therefore, as also depicted with dotted lines in both FIGS. 14 and 15, the compression controller 950 may further incorporate a power monitor 969 by which the compression controller 950 is coupled to the audio amplifier 960 (or to a power component, not shown, supplying power to the audio amplifier 960) to receive and monitor a signal from the power amplifier 960 (or that power component) indicating an amount of electrical power being drawn by the audio amplifier 960 to drive the acoustic driver 190 with an amplified form of an analog signal representing the acoustically-output audio. The power monitor 969 is provided with a power level setting indicating a level of consumption of electrical power by the audio amplifier 960 (and/or other components that may be monitored for electrical power consumption). Where a level of electrical power consumption is detected that is above what is specified by the power level setting and that continues beyond a predetermined period of time, it may be presumed that the cause is the provision of feedback-based ANR having ceased to function normally as a result of an occurrence of instability such that a sound associated with instability (e.g., a "howling" or "squealing" sound) is currently being acoustically output at a high amplitude. Where the compression controller 950 incorporates such an ability to monitor the electrical power consumed by the audio amplifier 960 and/or another component associated with the provision of at least feedback-based ANR, such monitoring of power consumption may be used alongside the analysis of the acoustically-output audio performed by the PLL 965, either to provide some degree of confirmation of there being an instance of instability, or as a secondary detector that an instance of instability is continuing despite an initial action taken that had already been taken by the compression controller 950 to counteract the instability in response to the detection of the instability by the analysis performed by the PLL 965.

Figure 16:
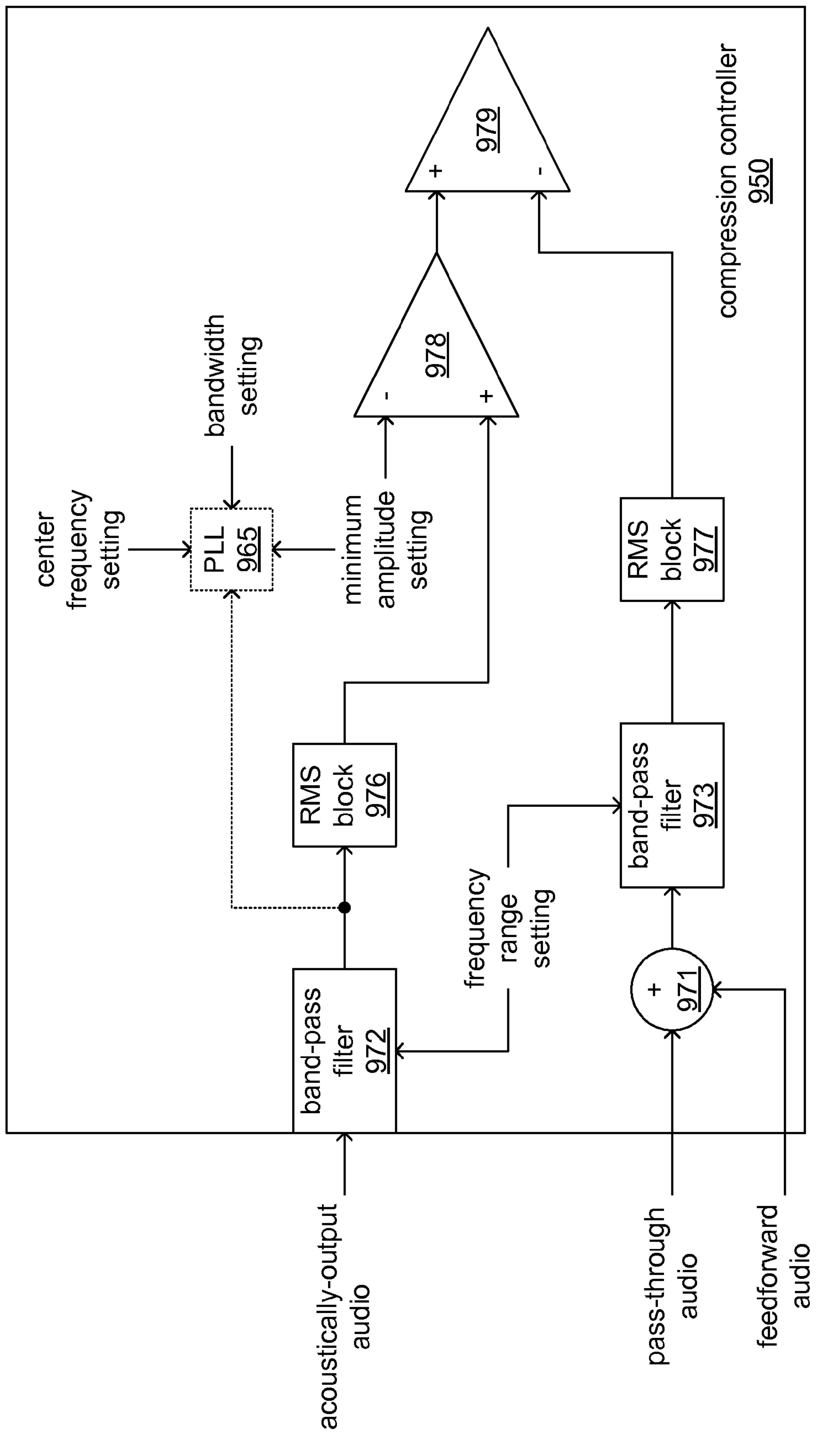

FIG. 16 depicts aspects of an internal architecture that may be employed by embodiments of the compression controller 950 where pass-through audio is supported in which the compression controller 950 incorporates at least a summing node 971, a pair of bandpass filters 972 and 973, a pair of RMS blocks 976 and 977, and a pair of comparators 978 and 979. As will be explained, the compression controller 950 may further incorporate the PLL 965, as indicated through the depiction of the PLL 965 in FIG. 16 with dotted lines.

The summing node 971 is a portion of the compression controller 950 that more directly receives both the pass-through audio and a feedforward audio (the feedforward audio could be either a feedforward reference noise sound or a feedforward anti-noise sound), sums these two pieces of audio, and provides the summed audio to the band-pass filter 973 to which the summing node 971 is coupled. The band-pass filter 972 is a portion of the compression controller 950 that more directly receives the acoustically-output audio. The band-pass filter 972 filters out sounds in the acoustically-output audio having frequencies outside of the range specified in a frequency range setting provided to the band-pass filter 972, and the band-pass filter 973 filters out sounds in the summed audio received from the summing node 971 having frequencies outside the same range. The band-pass filters 972 and 973 are coupled to the RMS blocks 976 and 977, respectively, and output their respective filtered forms of audio to the RMS blocks 976 and 977. The RMS blocks 976 and 977 calculate RMS values for the filtered forms of audio received from the band-pass filters 972 and 973, respectively. The output of the RMS block 976 is coupled to the non-inverting input of the comparator 978, and the output of the RMS block 977 is coupled to the inverting input of the comparator 979, thereby enabling the RMS blocks 976 and 977 to provide the results of their RMS calculations to the comparators 978 and 979, respectively. The comparator 978 is provided with a minimum amplitude setting at its inverting input to enable the comparator 978 to distinguish between sounds that have an amplitude at least as great as the amplitude specified by the minimum amplitude setting and sounds that do not. The output of the comparator 978 is coupled to the inverting input of the comparator 979 to enable the comparator 979 to compare the amplitudes of the outputs of the RMS block 976 (as gated through the comparator 978) and the RMS block 977. Where the electrical energy is detected by the comparator 979 as being greater in the acoustically-output audio than in the summation of the pass-through audio and the feedforward audio, the compression controller 950 determines that an instance of instability is occurring. Where the electrical energy is detected by the comparator 979 as being greater in the summation of the pass-through audio and the feedforward audio, the compression controller 950 determines that there is no instability.

It may be deemed desirable to further enhance the accuracy of the determinations made by the compression controller 950 as to whether or not instability is occurring by additionally incorporating the PLL 965. As depicted, in this case, the input of the PLL 965 is coupled to the output of the band-pass filter 972. Further, the PLL 965 is provided with the minimum amplitude setting, along with a center frequency setting and a bandwidth setting. As before, the center frequency setting and the bandwidth setting specify a range of frequencies of sounds onto which the PLL 965 may lock. This range of frequencies specified in this way to the PLL 965 may be the same range of frequencies specified to the band-pass filters 972 and 973 via the frequency range setting. The addition of the PLL 965 enables the distinguishing between sounds having a sinusoidal waveform that is usually indicative of instability and sounds that do not. Thus, the results of whether the PLL 965 locks onto a sound, or not, may be used alongside the results of the comparison in energy levels made by the comparator 979. With the addition of the PLL 965, the compression controller 950 determines that there is an instance of instability if the comparator 979 detects that the electrical energy in the acoustically-output audio is greater than in the summation of the pass-through audio and the feedforward audio, and the PLL 965 locks onto a sound.

Although not specifically depicted in FIG. 16, one or more VGAs (or other devices able to be employed to alter audio amplitudes) may be incorporated into the compression controller 950 to adjust relative amplitudes of one or more of the acoustically-output audio, the pass-through audio and the feedforward audio. This may be necessary, especially where the acoustically-output audio is received at a point following its amplification by the audio amplifier 960, where the pass-through audio is received from a source at a level of amplification that differs greatly from that of the acoustically-output audio, and/or where feedforward reference noise sounds detected by the feedforward microphone 130 are employed as the feedforward audio, so as to balance their relative amplitudes and thereby enable proper results from the subtraction performed by the subtraction node 971 and the comparison made by the comparator 979. Such VGA(s) (or other components) may be positioned to adjust amplitudes either before or after each of these pieces of audio is routed through one of the band-pass filters 972 and 973, and/or before or after the summing node 971.

Upon detection of a sound indicative of instability (i.e., having a combination of at least a frequency and minimum amplitude deemed to be associated with instability, and possibly also a sinusoidal waveform that may also be associated with instability) and/or a level of electrical power consumption indicative of instability, any of a variety of actions may be taken in response to counteract the instability, as has been previously discussed. Such actions may include compressing the amplitude of one or the other of the feedback and feedforward reference noise sounds detected by the feedback microphone 120 and the feedforward microphone 130 (where feedforward-based ANR is provided such that the feedforward microphone 130 is present). As has also been discussed, actions in response to the detection of instability may include the coordinated compression of both of the feedback and feedforward reference noise sounds. Still further, it may be deemed desirable to perform some degree of compression of the amplitude of any pass-through audio selected by a user of the personal ANR device 1000 to be acoustically output by the acoustic driver 190 as another response to the detection of instability. Thus, as depicted in FIG. 14, the compression controller 950 is coupled to one or more of the VGAs 125, 135, 145, 220 and/or 320.

Again, it is important to note that the compression controller 950 may be implemented with analog or digital circuitry, or a combination thereof. More specifically, where one or more of the acoustically-output audio, the pass-through audio and the feedforward audio are received by the compression controller 950 as analog signals representing those pieces of audio, one or more of the high-pass filters 962 and 963, the summing node 971, and the band-pass filters 972 and 973 may be implemented with analog circuitry, as well as possibly still other components of the compression controller 950, such as the PLL 965. Alternatively, where one or more of these pieces of audio are received by the compression controller 950 as digital data representing those pieces of audio, one or more of these components of the compression controller 950 may be implemented with digital circuitry. Further, where digital circuitry is used in implementing one or more of these components, such a digital circuit implementation may entail the use of a processing device (e.g., the processing device 510) executing one or more sequences of instructions to instantiate and perform the functions of one or more of these components. Still further, the high-pass filters 962 and 963 and/or the band-pass filters 972 and 973 may be drawn from a bank of filters (as in the case of the filter bank 550 of the internal architecture 2200*a*) or may be instantiations of routines for implementing filters stored in a storage (as in the case of the storage 520 of the internal architecture 2200*b*).

Other implementations are within the scope of the following claims and other claims to which the applicant may be entitled.

The invention claimed is:

1. A method of detecting instability in providing feedback-based active noise reduction (ANR) comprising monitoring audio that comprises feedback anti-noise sounds employed in providing the feedback-based ANR for a sound having a frequency within a predetermined range of frequencies and having an amplitude that at least meets a predetermined minimum amplitude, wherein the combination of the range of predetermined frequencies and the predetermined amplitude is associated with sounds indicative of instability, and monitoring audio that comprises feedback anti-noise sounds comprises:

configuring a phase-locked loop (PLL) to lock onto a sound having a frequency within the predetermined range of frequencies and an amplitude at least meeting the predetermined minimum amplitude;

monitoring audio to be acoustically output by an acoustic driver that comprises the feedback anti-noise sounds with the PLL; and awaiting an instance of the PLL locking onto a sound, further comprising routing the audio monitored by the PLL through a first high-pass filter, and routing the audio from the first high-pass filter through a summing node configured to subtract pass-through audio that has been routed through a second high-pass filter before providing the audio to the PLL.

2. The method of claim 1, further comprising monitoring the audio that comprises feedback anti-noise sounds employed in providing the feedback-based ANR for a sound having a sinusoidal waveform in addition to having a frequency within the predetermined range of frequencies and having an amplitude that at least meets the predetermined minimum amplitude.

3. The method of claim 1, wherein monitoring audio that comprises feedback anti-noise sounds comprises monitoring audio to be acoustically output by an acoustic driver to employ the feedback anti-noise sounds in providing the feedback-based ANR.

4. The method of claim 1, further comprising deriving the predetermined range of frequencies from an electrical characteristic of at least one component employed in providing the feedback-based ANR and from an acoustic characteristic of at least one other component employed in providing the feedback-based ANR.

5. A method of detecting instability in providing feedback-based active noise reduction (ANR) comprising monitoring audio that comprises feedback anti-noise sounds employed in providing the feedback-based ANR for a sound having a frequency within a predetermined range of frequencies and having an amplitude that at least meets a predetermined minimum amplitude, wherein the combination of the range of predetermined frequencies and the predetermined amplitude is associated with sounds indicative of instability, wherein monitoring audio that comprises feedback anti-noise sounds comprises:

configuring a first band-pass filter to pass sounds of the audio that comprises feedback anti-noise sounds having a frequency within the predetermined range of frequencies;

calculating a root mean square of the sounds that pass through the first band-pass filter; and comparing the root mean square of the sounds that pass through the first band-pass filter to the predetermined minimum amplitude.

6. The method of claim 5, wherein monitoring audio that comprises feedback anti-noise sounds further comprises:

configuring a phase-locked loop PLL to lock onto a sound having a frequency within the predetermined range of frequencies and an amplitude at least meeting the predetermined minimum amplitude;

monitoring the sounds that pass through the first band-pass filter with the PLL; and awaiting an instance of the PLL locking onto a sound.

7. The method of claim 5, wherein monitoring audio that comprises feedback anti-noise sounds further comprises:

configuring a second band-pass filter to pass sounds of audio comprising at least one of pass-through audio and feedforward anti-noise sounds having a frequency within the predetermined range of frequencies;

calculating a root mean square of the sounds that pass through the second band-pass filter; and comparing the root mean square of the sounds that pass through the second band-pass filter to results of comparing the root mean square of the sounds that pass through the first band-pass filter to the predetermined minimum amplitude.

8. A method of detecting instability in providing feedback-based active noise reduction ANR comprising monitoring audio that comprises feedback anti-noise sounds employed in providing the feedback-based ANR for a sound having a frequency within a predetermined range of frequencies and having an amplitude that at least meets a predetermined minimum amplitude, wherein the combination of the range of predetermined frequencies and the predetermined amplitude is associated with sounds indicative of instability, further comprising monitoring an amount of electric power drawn by an audio amplifier employed in amplifying the audio that comprises feedback anti-noise sounds for an instance of the amount of electric power drawn by the audio amplifier at least meeting a predetermined minimum level of electric power; wherein the combination of the range of predetermined frequencies, the predetermined amplitude is associated with sounds indicative of instability, and the predetermined minimum level of electric power is associated with sounds indicative of instability.

9. A personal active noise reduction (ANR) device providing at least feedback-based ANR to attenuate environmental noise sounds at a location adjacent and ear of a user of the personal ANR device, the personal ANR device comprising:

an ANR circuit to derive at least feedback anti-noise sounds in providing the feedback-based ANR;

an acoustic driver coupled to the ANR circuit to acoustically output audio that comprises the feedback anti-noise sounds; and a compression controller incorporated into the ANR circuit to monitor the audio acoustically output by the acoustic driver for a sound having a frequency within a predetermined range of frequencies and having an amplitude that at least meets a predetermined minimum amplitude, wherein the combination of the range of predetermined frequencies and the predetermined amplitude is associated with sounds indicative of instability;

wherein the compression controller comprises:

a phase-locked loop (PLL) configurable to monitor the audio acoustically output by the acoustic driver and to lock onto a sound within the audio acoustically output by the acoustic driver having a frequency within the predetermined range of frequencies and an amplitude at least meeting the predetermined minimum amplitude, a first high-pass filter through which the audio to be acoustically output by the acoustic driver is routed before being monitored by the PLL, a second high-pass filter through which pass-through audio received by the ANR circuit is routed; and a summing node through which the audio to be acoustically output by the acoustic driver is routed after being routed through the first high-pass filter, and from which the pass-through audio routed through the second high-pass filter is subtracted before being monitored by the PLL.

10. The personal ANR device of claim 9, wherein the compression controller further monitors the audio acoustically output by the acoustic driver for a sound having a sinusoidal waveform in addition to having a frequency within the predetermined range of frequencies and having an amplitude that at least meets the predetermined minimum amplitude.

11. A personal active noise reduction (ANR) device providing at least feedback-based ANR to attenuate environmental noise sounds at a location adjacent and ear of a user of the personal ANR device, the personal ANR device comprising:

an ANR circuit to derive at least feedback anti-noise sounds in providing the feedback-based ANR;

an acoustic driver coupled to the ANR circuit to acoustically output audio that comprises the feedback anti-noise sounds; and a compression controller incorporated into the ANR circuit to monitor the audio acoustically output by the acoustic driver for a sound having a frequency within a predetermined range of frequencies and having an amplitude that at least meets a predetermined minimum amplitude, wherein the combination of the range of predetermined frequencies and the predetermined amplitude is associated with sounds indicative of instability;

wherein the compression controller comprises:

a first band-pass filter configurable to pass sounds of the audio acoustically output by the acoustic driver having a frequency within the predetermined range of frequencies;

a first RMS block to calculate a root mean square of the sounds that pass through the first band-pass filter; and a first comparator to compare the root mean square calculated by the RMS block to the predetermined minimum amplitude.

12. The personal ANR device of claim 11, wherein the compression controller further comprises a phase-locked loop PLL to monitor the sounds that pass through the first band-pass filter and to lock onto a sound having a frequency within the predetermined range of frequencies and an amplitude at least meeting the predetermined minimum amplitude.

13. The personal ANR device of claim 11, wherein the compression controller further comprises:

a second band-pass filter configurable to pass sounds of audio comprising at least one of pass-through audio and feedforward anti-noise sounds having a frequency within the predetermined range of frequencies;

a second RMS block to calculate a root mean square of the sounds that pass through the second band-pass filter; and a second comparator to compare the root mean square calculated by the second RMS block to results of comparing the root mean square calculated by the first RMS block to the predetermined minimum amplitude.

* * * * *